(12) United States Patent
Beck

(10) Patent No.: US 10,905,579 B2
(45) Date of Patent: Feb. 2, 2021

(54) METHODS OF USING NASAL INSERTS FOR TREATMENTS

(71) Applicant: Beck Medical, Ltd., Giva'at Ada (IL)

(72) Inventor: Adva Beck, Giva'at Ada (IL)

(73) Assignee: Beck Medical, Ltd.

( * ) Notice: Subject to any disclaimer, the term of this patent is extended or adjusted under 35 U.S.C. 154(b) by 239 days.

(21) Appl. No.: 16/014,354

(22) Filed: Jun. 21, 2018

(65) Prior Publication Data

US 2018/0369007 A1   Dec. 27, 2018

Related U.S. Application Data

(60) Provisional application No. 62/623,687, filed on Jan. 30, 2018, provisional application No. 62/579,611, filed on Oct. 31, 2017, provisional application No. 62/540,907, filed on Aug. 3, 2017, provisional application No. 62/533,222, filed on Jul. 17, 2017, provisional application No. 62/523,040, filed on Jun. 21, 2017.

(51) Int. Cl.
| | |
|---|---|
| *A61F 5/00* | (2006.01) |
| *A61M 21/00* | (2006.01) |
| *A61M 15/08* | (2006.01) |
| *A61F 5/56* | (2006.01) |

(52) U.S. Cl.
CPC .......... *A61F 5/0013* (2013.01); *A61M 15/08* (2013.01); *A61M 21/00* (2013.01); *A61F 5/56* (2013.01); *A61M 2021/0016* (2013.01); *A61M 2021/0077* (2013.01); *A61M 2202/0208* (2013.01); *A61M 2210/0618* (2013.01); *A61M 2210/0681* (2013.01)

(58) Field of Classification Search
CPC ......... A61F 5/0013; A61F 5/56; A61M 21/00; A61M 2021/0016; A61M 15/08; A61M 2210/0618; A61M 2202/0208; A61M 2021/0077; A61M 2210/0681
See application file for complete search history.

(56) References Cited

U.S. PATENT DOCUMENTS

| | | |
|---|---|---|
| 5,601,594 A | 2/1997 | Best |
| 8,025,635 B2 | 9/2011 | Eaton et al. |
| 8,517,026 B2 | 8/2013 | Amon |

(Continued)

FOREIGN PATENT DOCUMENTS

CN   204709586 U   10/2015

OTHER PUBLICATIONS

Aschenbrenner et al., "The Influence of Olfactory Loss on Dietary Behaviors", Laryngoscope, 2008, pp. 135-144, vol. 118.

(Continued)

*Primary Examiner* — Christine H Matthews
*Assistant Examiner* — Joshua Daryl D Lannu
(74) *Attorney, Agent, or Firm* — The Webb Law Firm

(57) ABSTRACT

Herein disclosed are methods of using nasal inserts for various different ailments. Easy modification of the insert allows for treatment of various ailments that can readily be treated via the nose, such as ailments triggered by smell. Specifically, the insert can direct air into or out of the nasal cavity and/or delivers medicinal substances to the appropriate regions, thereby providing the appropriate therapeutic effect, depending on the ailment being treated.

25 Claims, 12 Drawing Sheets

(56) References Cited

U.S. PATENT DOCUMENTS

| | | |
|---|---|---|
| 8,839,790 B2 | 9/2014 | Beck |
| 2004/0020492 A1 | 2/2004 | Dubrul et al. |
| 2005/0240147 A1 | 10/2005 | Makower et al. |
| 2015/0068537 A1* | 3/2015 | Beck ..................... A24F 47/00 128/848 |
| 2018/0369007 A1 | 12/2018 | Beck |

OTHER PUBLICATIONS

Beck Medical, Design U.S. Appl. No. 29/616,909, filed Nov. 21, 2017.

* cited by examiner

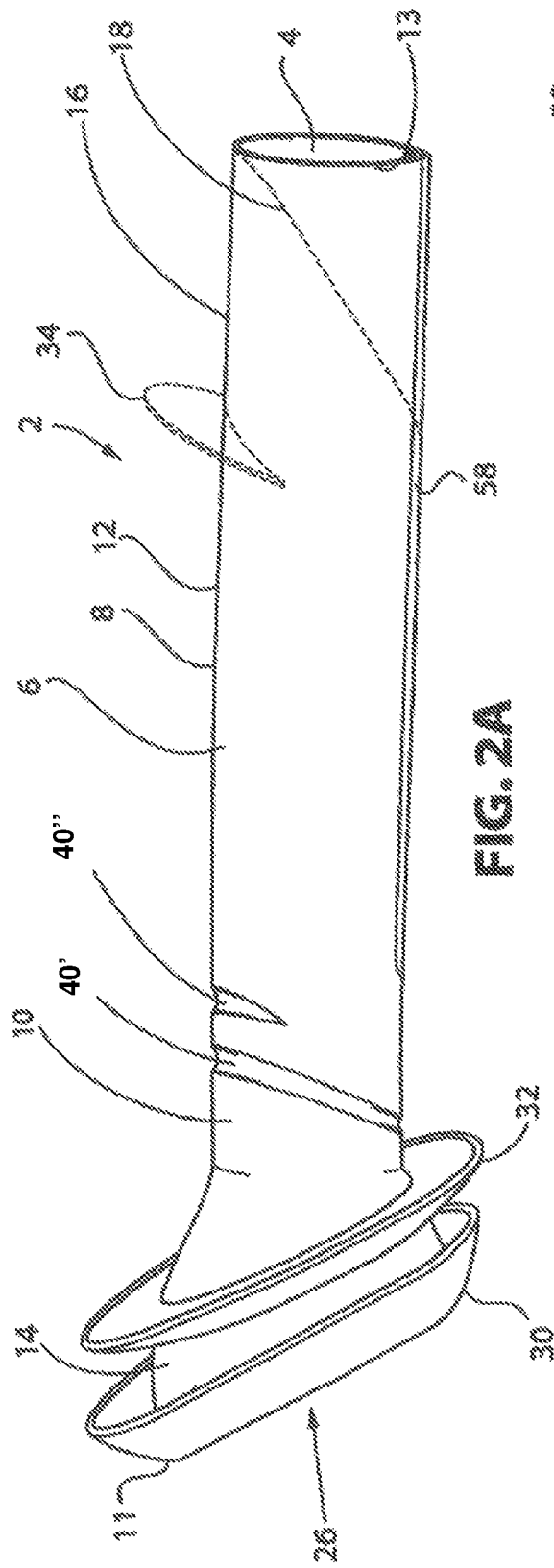
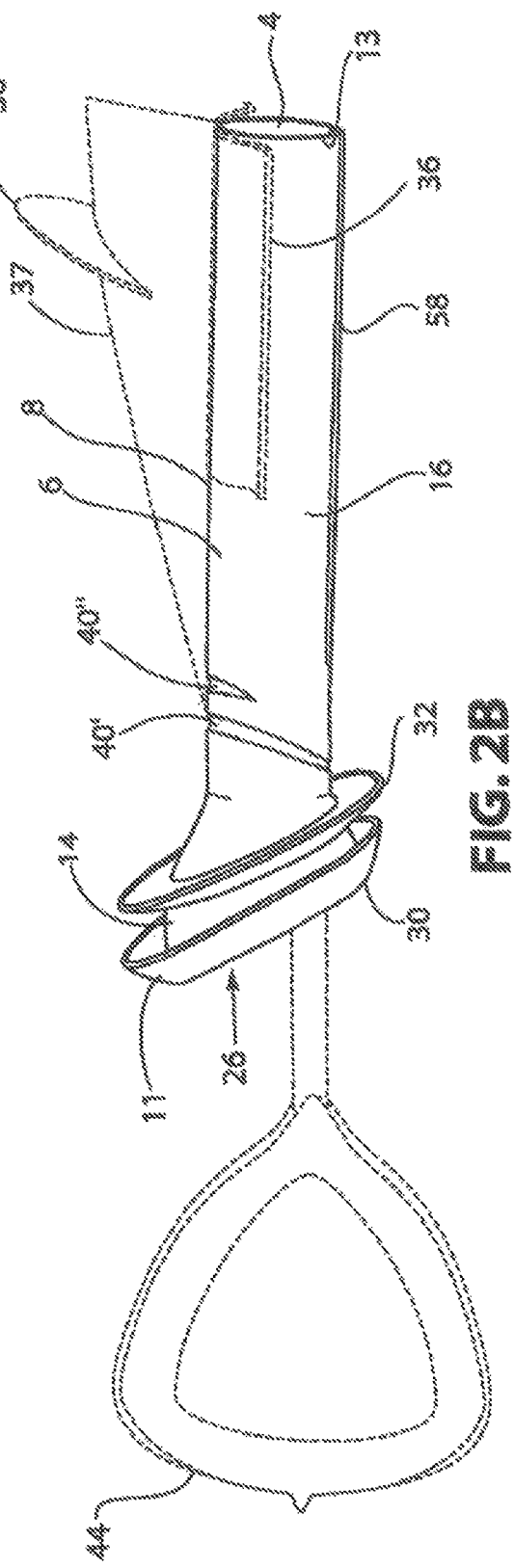
FIG. 2A
FIG. 2B

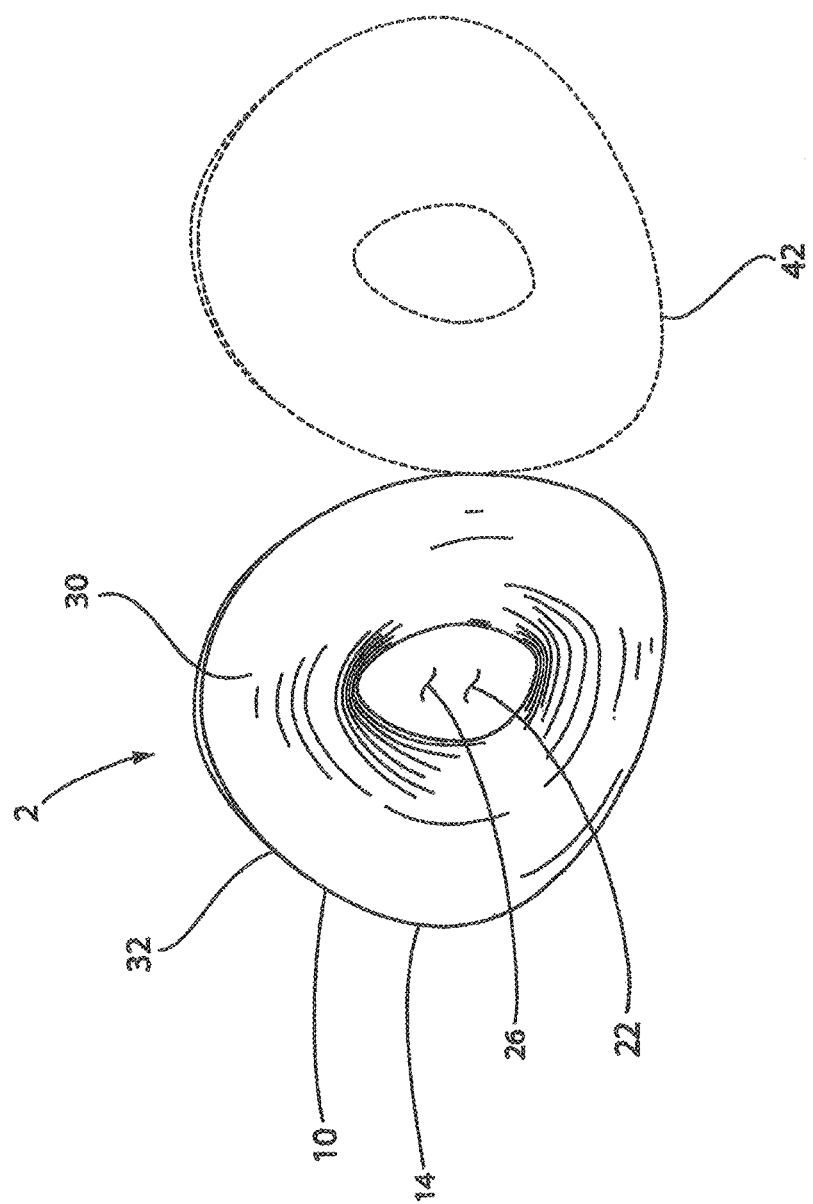

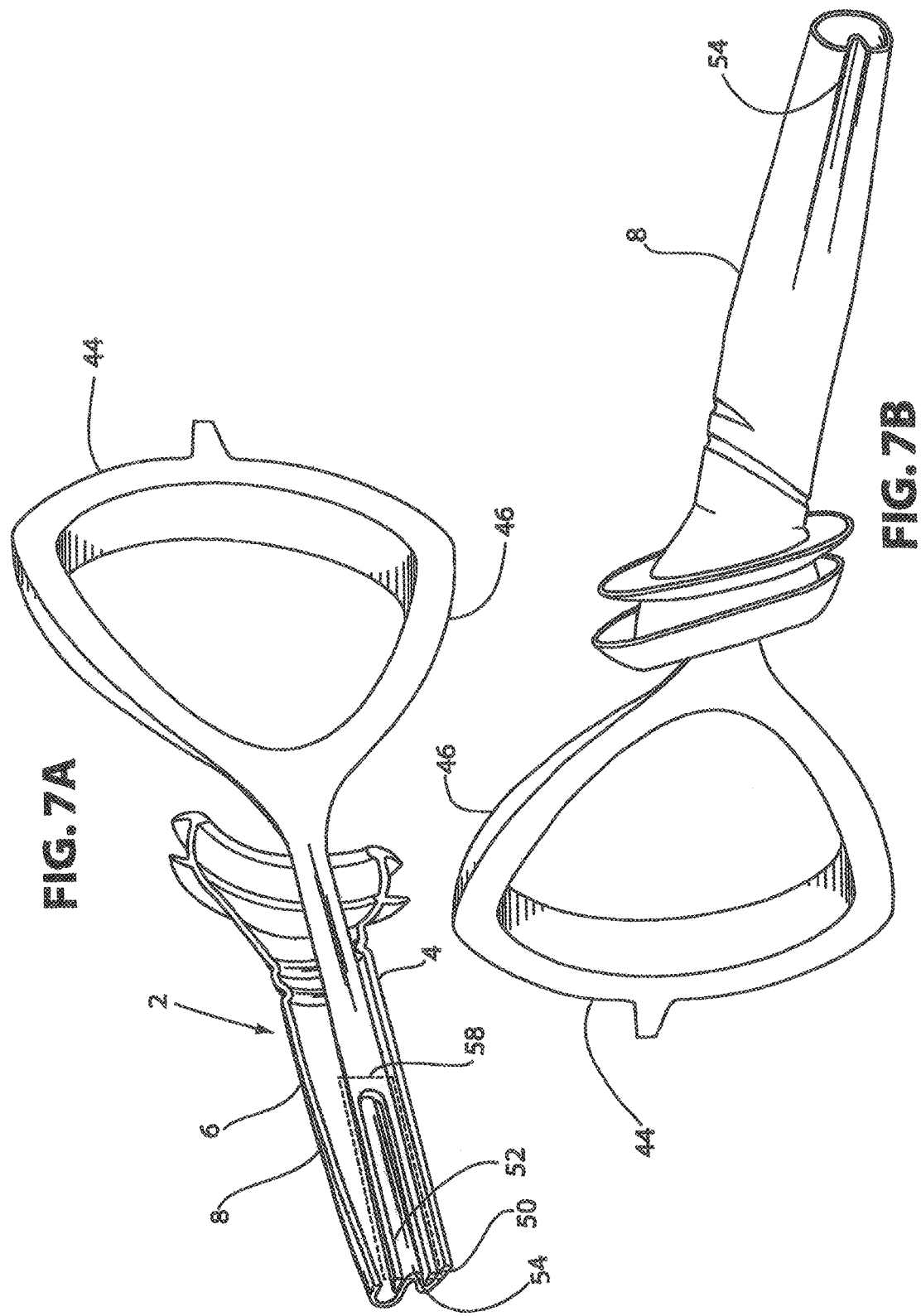

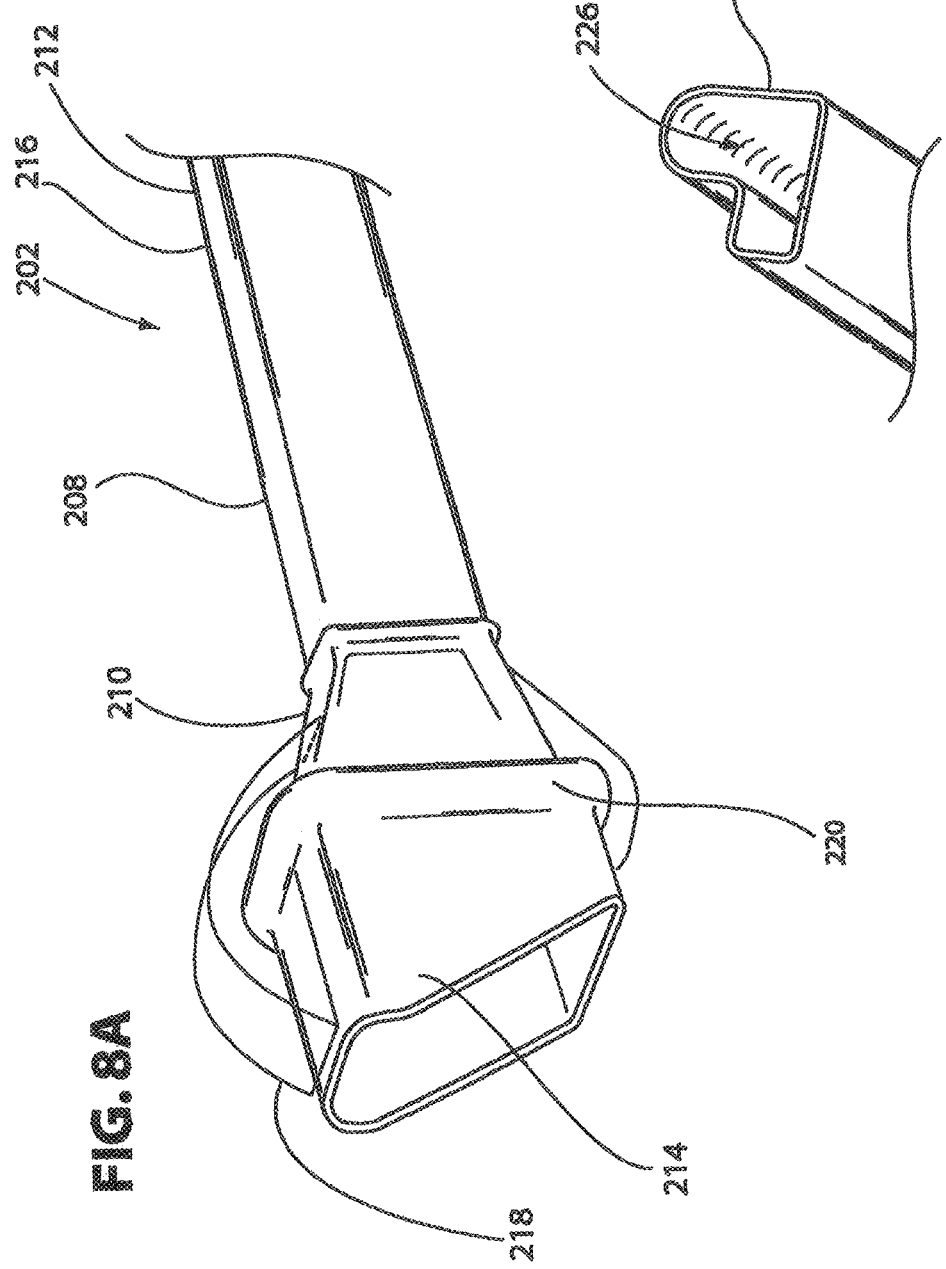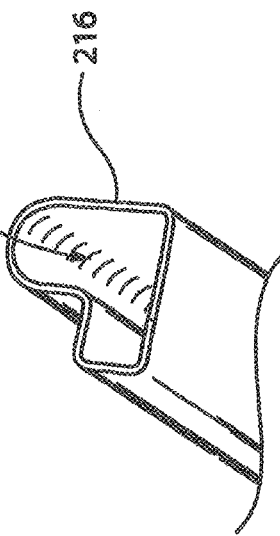

METHODS OF USING NASAL INSERTS FOR TREATMENTS

CROSS-REFERENCE TO RELATED APPLICATION

This application claims the benefit of U.S. Provisional Patent Application No. 62/523,040 entitled "Methods of Using Nostril Inserts to Treat/Prevent Diabetes, Weight Gaining, Overweight/Obesity/Morbid Obesity, Allergies, Addiction Rehabilitation, and Methods for Alteration of Food Choices" filed Jun. 21, 2017, U.S. Provisional Patent Application No. 62/533,222, entitled "Methods of Using Nostril Inserts to Block Receptors in the Nose or Accessible via the Nose" filed Jul. 17, 2017, U.S. Provisional Patent Application No. 62/540,907, entitled "Alteration of Serum Insulin and Preference for Sweets in Humans by a Device That Inhibits Smell" filed Aug. 3, 2017, U.S. Provisional Patent Application No. 62/579,611, entitled "Methods of Using Nostril Inserts to Treat/Prevent Diabetes, Weight Gaining, Overweight/Obesity/Morbid Obesity, Allergies, Addiction Rehabilitation, and Methods for Alteration of Food Choices" filed Oct. 31, 2017, and U.S. Provisional Patent Application No. 62/623,687, entitled "Weight Loss and Alterations in Dietary Preferences Due to Reduction of Smell by a Novel Nasal Device" filed Jan. 30, 2018.

BACKGROUND OF THE INVENTION

The present invention relates generally to nasal inserts and, more particularly, to apparatuses and methods for: treating and/or preventing diabetes, addiction rehabilitation, alteration of food preferences, treating overweight/obesity/morbid obesity, reducing fat mass, reducing fat mass without reducing fat free mass and/or muscle mass and/or essential tissue, increasing bodily fat burn, affecting fat deposition and/or fat handling and/or promote lipolysis, increase thermogenesis, increasing and/or changing body energy expenditure, treating children and teenagers that are overweight/obesity/morbid obesity, improvement of blood parameters and metabolic parameters and other bodily parameters, reducing fat percentage, reducing the risk for cardiovascular issues, and/or treatment of cardiovascular issues, reducing/treating/affecting blood pressure, hypertension and other metabolic disorder issues, and additionally methods for treating/managing/preventing or otherwise affecting allergies. Another aspect of this invention would be to provide variety of methods to manipulate smelling and/or olfactory, in order to leverage them for medical and non-medical purposes.

The present invention relates generally to nasal inserts and, more particularly, to apparatuses and methods for treating and/or preventing diabetes (type 2 diabetes mellitus, type 1 diabetes, other types of diabetes, diabetes in general), addiction rehabilitation, alteration of food preferences, treating overweight/obesity/morbid obesity, treating children and teenagers that are overweight/obesity/morbid obesity, for weight management, improvement of blood parameters, and bodily metabolic related, parameters and other bodily parameters and act, affect bodily fat tissues (brown, white, location etc.) management, lipid management, glucose management, hepatic related act etc. not limited), reducing the risk for and/or treatment of cardiovascular issues, hypertension and other metabolic disorder issues, and additionally methods for treating/managing allergies. Another aspect of this invention would be to provide variety of methods to manipulate smelling/olfactory/nasal and related mechanisms and organs, in order to leverage them for medical and non-medical purposes.

The treatments or uses may include a use of odor prevention nasal insert, smelling/olfactory manipulation apparatus, treatment/component/drug delivery apparatus, a nasal device or other device, and may also be related to the application or use of other things with or without specific apparatus, such as drugs, gels, odors and a like via the nasal cavity for different applications.

The medical and non-medical treatments conducted by using such apparatuses and methods, may affect a person's, or other mammal's, physical-, medical-, cognitive-, emotional- and/or other aspects of well-being or other, by preventing/decreasing/manipulating smelling or olfactory and related aspects or by delivering drug(s), odor(s), or other material(s)/signal(s), and/or by preventing/decreasing/manipulating such substances which may be added may or may not be environmental, or by using different embodiments of the device and/or by positioning the device to support the required result and in general by using the herein described nasal insert. Such affect is achieved by preventing/blocking/decreasing/delaying/manipulating/affecting/leveraging/acting over/changing etc in any manner, one or more of the following: (1) smelling/olfactory related/nasal related inputs, for example: (not limited) air, odor(s), material(s), molecule(s), particle(s), substance(s), hormone(s), neural signal(s), other signals, flow, etc. Where such inputs can be original by environment, and/or bodily/by bodily act/response etc., and/or can be added (for example—not limited—they can be incorporated in the device/method or provided in any other connection to it, or they can be given to the person/mammal in other manner via nasal or differently intravenous/via mouth etc.), or otherwise exist/created, and where such added things can be of any relevant type, for example (not limited): drug(s), hormone(s), odor(s), peptide(s), signal(s), cell(s), gen(s), bacteria(s), neuron(s), radiation(s), act(s) etc. and/or otherwise can enable the required act etc.; and/or (2) smelling/olfactory related/nasal related organ(s)/element(s) and/or their act/response/behavior/or any other characteristics etc., for example: (not limited): sensors, receptors, hormones, neurons, nerves, cells, signals, mucosa, mucus, brain in general and/or specific, blood stream, CNS, the autonomic nervous system, sympathetic/para-sympathetic nerve activity, activation of b-adrenergic receptors/cells, affecting white and/or brown adipose, promote/affect lipolysis, excitation, blockage, secretion, synthesization, signaling transmission, division, etc. And also by using different embodiments of the device and/or by positioning the device to support the required result and in general by using the herein described nasal insert and the described methods. As clarified, the methods of use of nasal apparatuses that provided herein may also function by preventing/decreasing/manipulating etc. particular material(s)/signal(s) etc. in regards of the olfactory and/or other relevant parts within the nasal cavity or organs/elements that are connected to nasal cavity/olfactory, and not only odors particles and manipulating them and/or the olfactory organ itself and related organs for achieving the required effect. The apparatuses and methods provided herein may also function by preventing particular material(s) from reaching the olfactory and other relevant parts within the nasal cavity or beyond it and not only odors particles.

The nasal structure is unique and complex. It starts with the nostril opening. The forward section, within and above each nostril, is called the vestibule. Behind the vestibule there is the nasal valve and following it deeper and along each lateral wall are three elevations, running generally from front to rear. Each elevation, called a nasal concha or turbinate, hangs over an air passage. These air passages are also known as the inferior meatus—the largest, the middle meatus, the posterior meatus and the superior meatus which is the smallest, upper most passage. The superior meatus provides access to several elements such as, part of the sinuses, as well as the olfactory area which has been proven to contain receptors for many hormones, and for directly linking the nose and the senses of the nose to the brain, for example: functions such as (non-limiting) memory, amygdala and limbic structure, hypothalamus, and branches of the trigeminal nerve and CNS (Central Nervous System), and to other elements. The olfactory area enables the transfer of molecules and signals to the brain that are blocked in the brain blood barrier (bbb).

The middle meatus, provides access to part of the sinuses opening as well as to other elements. The conches are not connected to the septum, and there exists a passage from the nasal floor to the nasal roof. The majority of the inhaled air naturally flows through the inferior meatus. Another portion of the air goes through the middle one and only minority of the air reaches the upper and superior meatuses. The nasal cavity mucosa and cilia are rich in blood vessels and enable quick absorption of materials directly to the blood system. Nasal based treatments also serve as an alternative for needle injection based therapies and vaccinations, especially for therapies where adverse events in the gastrointestinal tract and first-pass metabolism in the liver are to be avoided.

In summary, the nasal cavity due to its physical characteristics, serves as a perfect drug delivery and treatment vehicle. It is connected to the endocrine system and brain, branches of the trigeminal nerve, blood vessels and through other elements, which allows for direct Nose to Brain (N2B) treatments CNS treatments, via blood stream treatments, and other treatments via specific drug and/or substance delivery, as well as via other manipulations.

Accordingly, there is a need in the art and in actual current reality to provide a set of methods that may answer such needs and will enhance possibilities for medical and non-medical treatment via the nasal cavity.

SUMMARY OF THE INVENTION

Provided herein is a method for treating and/or preventing diabetes according to a therapeutic regimen, comprising the steps of: providing a nasal insert, said nasal insert including a body for insertion into a nasal cavity, said nasal insert body defining an air passageway, and having an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body is configured to create a bypass of the olfactory region or directs the air and/or other substance/signals to bypass the olfactory region thereby delaying, blocking, or reducing the amount of odors and/or other particles/signals reaching the olfactory region and/or redirecting air to other regions of the nasal cavity or is configured to direct air/substances/signals towards the olfactory region; and wherein the redirecting of the air and the blocking or reducing of odors alters metabolic processes thereby producing a therapeutic effect.

Additionally, provided herein is a method for addiction rehabilitation according to a therapeutic regimen, comprising the steps of: providing a nasal insert, said nasal insert including a body for insertion into a nasal cavity, said nasal insert body comprising an inner surface defining an air passageway, and an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body is configured to create a bypass of the olfactory region or directs the air and/or other substance to bypass the olfactory region thereby delaying, blocking, or reducing the amount of odors and/or other particles/odor(s)/substance(s)/signal(s) reaching the olfactory region and/or redirecting air/odor(s)/substance(s)/signal(s) to other regions of the nasal cavity or is configured to direct air/odor(s)/substance(s)/signal(s) towards the olfactory region; and wherein the redirecting of the air/substances/signals and the blocking or reducing of odor(s)/air/substance(s)/signal(s) produces a therapeutic effect.

In another aspect, provided herein is a method for alteration of food preferences according to a therapeutic regimen, comprising the steps of: providing a nasal insert, said nasal insert including a body for insertion into a nasal cavity, said nasal insert body comprising an inner surface defining an air passageway, and an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body is configured to create a bypass of the olfactory region or directs the air and/or other substance to bypass the olfactory region thereby delaying, blocking, or reducing the amount of odors and/or other particles/substance(s)/signal(s) reaching the olfactory region and/or redirecting air/odor(s)/substance(s)/signal(s) to other regions of the nasal cavity or is configured to direct air towards the olfactory region; and wherein the redirecting of the air/odor(s)/substance(s)/signal(s) and the blocking or reducing of odors alters metabolic processes thereby promoting healthier food choices and producing a therapeutic effect.

Also provided herein is a method for treating overweight/obesity/morbid obesity according to a therapeutic regimen, comprising the steps of: providing a nasal insert, said nasal insert including a body for insertion into a nasal cavity, said nasal insert body comprising an inner surface defining an air passageway, and an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body is configured to create a bypass of the olfactory region or directs the air and/or other substance to bypass the olfactory region thereby delaying, blocking, or reducing the amount of odors and/or other particles reaching the olfactory region and/or redirecting air to other regions of the nasal cavity or is configured to direct air towards the olfactory region; and wherein the redirecting of the air and the blocking or reducing of odors alters metabolic processes thereby reducing the urge to eat and producing a therapeutic effect.

Also provided is a method for preventing or treating allergies, comprising the steps of: providing a nasal insert, said nasal insert including a body for insertion into a nasal cavity, said nasal insert body comprising an inner surface defining an air passageway, and an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body is configured to create a bypass of the olfactory region or directs the air and/or other substance to bypass the olfactory region thereby delaying, blocking, or reducing the amount of odors and/or other particles reaching the olfactory region and/or redirecting air to other regions of the nasal cavity or is configured to direct air towards the olfactory region; and wherein the nasal insert body prevents particles causing allergic reaction from reaching unwanted areas in the nasal cavity.

Further provided herein is a method for treating and/or preventing over-weight/obesity/morbid obesity according to a therapeutic regimen, comprising the steps of: providing a nasal insert, said nasal insert including a body for insertion into a nasal cavity, said nasal insert body defining an air passageway, and having an outer surface, said outer surface configured to form a seal between said nasal insert body and the nasal cavity; inserting said nasal insert body into the nasal cavity such that the nasal insert body rests against a portion of the nasal cavity wherein the nasal insert body is configured to create a bypass of the olfactory region or directs the air and/or other substance to bypass the olfactory region thereby delaying, blocking, or reducing the amount of odors and/or other particles reaching the olfactory region and/or redirecting air to other regions of the nasal cavity or is configured to direct air towards the olfactory region; and wherein the redirecting of the air and/or other substances alters food choices, and/or reduces eating, and/or increases bodily energy expenditure, and/or enhances or changes an effect on bodily metabolic pathways, and/or directs specific odors/particles to olfactory/brain, and/or enhances an effect of specific particles or odors over the olfactory and brain, and/or alters metabolic processes thereby producing a therapeutic effect.

Also provided herein is a method for preventing weight gain or for supporting weight loss according to a therapeutic regimen, comprising the steps of: providing a nasal insert, said nasal insert including a body for insertion into a nasal cavity, said nasal insert body comprising an inner surface defining an air passageway, and an outer surface, said outer surface configured to form a seal between said nasal insert body and the nasal cavity; inserting said nasal insert body into the nasal cavity such that the nasal insert body rests against a portion of the nasal cavity wherein the nasal insert body is configured to create a bypass of the olfactory region or directs the air and/or other substance to bypass the olfactory region thereby delaying, blocking, or reducing the amount of odors and/or other particles reaching the olfactory region and/or redirecting air to other regions of the nasal cavity or is configured to direct air towards the olfactory region; and wherein the redirecting of the air and the blocking or reducing of odors alters metabolic processes thereby reducing the urge to eat and producing a therapeutic effect.

Also provided is a method for addiction rehabilitation comprising the steps of: providing a nasal insert, said nasal insert including a nasal insert body for insertion into a nasal cavity, said nasal insert body comprising an inner surface or material, and an outer surface or material, said nasal insert body being adapted to fit inside a nasal cavity; inserting said nasal insert body into the nasal cavity such that the nasal insert body rests against a portion of the nasal cavity, creating a partial or full blockage of the nasal cavity; and wearing the nasal insert body for an amount of time, wherein the wearing of the nasal insert body creates a feeling of a mild cold and/or light runny nose, and/or a feeling of sickness or a feeling of disgust and/or less enjoyable or less comfortable experience while attempting to consume an addictive substance, resulting in a reduction or elimination of a user's craving to consume the addictive substance and/or in reduction or elimination of the amount of consumption of the addictive substance.

Also provided herein is a method for treating diabetes, for alteration of food preferences, for treating allergies, for treating overweight/obesity/morbid obesity according to a therapeutic regimen, comprising the steps of: providing a nasal insert, said nasal insert including a nasal insert body for insertion into a nasal cavity, said nasal insert body comprising an inner surface or material, and an outer surface or material, said nasal insert body being adapted to fit inside a nasal cavity; inserting said nasal insert body into the nasal cavity such that the nasal insert body rests against a portion of the nasal cavity, creating a partial or full blockage of the nasal cavity; and wearing the nasal insert body for an amount of time wherein wearing of the nasal insert body creates a feeling of a mild cold and/or light runny nose, and/or a feeling of sickness or a feeling of disgust and/or less enjoyable or less comfortable experience resulting in a the relevant improvement.

Provided herein is a method of using a nasal insert as described herein for treating of diabetes, prevention of diabetes, reducing the risk for developing diabetes, help living well with diabetes, preventing weight gaining, treating allergies, alteration of food choices, addiction rehabilitation, reducing consumption of and/or craving to sweet foods, reducing consumption of and/or craving to sugar, reducing consumption of and/or craving to artificial sweeteners, reducing consumption of and/or craving to sweet beverages, reducing consumption of and/or craving to fatty foods, reducing consumption of and/or craving to carbohydrate foods, reducing consumption of and/or craving to backed and pastry based foods, enhancing consumption of and/or craving to healthy foods, altering eating habits towards a healthier diet, treating blood pressure and/or hypertension, reducing the risk for developing blood pressure/hypertension problems, help living well with blood pressure problems/hypertension.

Also provided is a method for treating weight loss, comprising: providing a nasal insert, said nasal insert including a body for insertion into a nasal cavity, said nasal insert body defining an air passageway, and having an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body creates a partial or full bypass of the olfactory region or directs the inhaled air and/or other substance to bypass the olfactory region thereby delaying, blocking, or reducing the amount of odors and/or other particles and/or any substance reaching the olfactory region by inhalation, and wherein said nasal insert body configured to enable the reach of food or other odors or particles coming from the throat area and/or from inside the body to the olfactory area and wherein the combination prevention/decrease of environmental odors/particles/signals while enabling the reach of odors/particles/signals of eaten foods/ingredients/other particles coming from the area of the throat and/or from other internal organs leads to weight loss and/or prevents weight gain.

Additionally, provided herein is a method for treating and/or preventing diabetes, and/or reducing the risk for developing diabetes and/or help living well with diabetes comprising the steps of: providing a nasal insert, said nasal insert including a body for insertion into a nasal cavity, said nasal insert body defining an air passageway, and having an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body is configured to create a bypass of the olfactory region or directs the air and/or odors, and/or other substance/particles/signals/elements/any substance/ etc. to bypass the olfactory region thereby delaying, blocking, manipulating or reducing the amount of air and/or odors, and/or other any substance/particles/signals/elements/etc. from reaching to, or in relation of the olfactory region and/or redirecting air and/or odors, and/or other substance/particles/signals/elements/any substance/etc. to other regions of the nasal cavity or beyond it, or is configured to direct air and/or odors, and/or other substance/ particles/signals/elements/etc. towards the olfactory region; and wherein the redirecting of air and/or odors, and/or other substance/particles/signals/elements/any substance/etc. and/ or the blocking or reducing or manipulation of air and/or odors, and/or other substance/particles/signals/elements/etc. alters metabolic processes thereby producing a therapeutic or wellness effect.

Additionally, provided herein is a method for treating and/or preventing blood pressure problems/hypertension, and/or reducing the risk for developing blood pressure problems/hypertension and/or help living well with blood pressure problems/hypertension comprising the steps of: providing a nasal insert, said nasal insert including a body for insertion into a nasal cavity, said nasal insert body defining an air passageway, and having an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body is configured to create a bypass of the olfactory region or directs the air and/or odors, and/or other substance/particles/signals/elements/etc. to bypass the olfactory region thereby delaying, blocking, manipulating or reducing the amount of air and/or odors, and/or other substance/particles/signals/elements/etc. from reaching to, or in relation of the olfactory region and/or redirecting air and/or odors, and/or other substance/particles/signals/elements/any substance etc. to other regions of the nasal cavity or beyond it, or is configured to direct air and/or odors, and/or other any substance/particles/signals/elements/etc. towards the olfactory region; and wherein the redirecting of air and/or odors, and/or other substance/particles/signals/ elements/etc. and/or the blocking or reducing or manipulation of air and/or odors, and/or other any substance/particles/ signals/elements/etc. alters bodily processes thereby producing a therapeutic or wellness effect.

Also provided herein is a method for addiction rehabilitation, comprising the steps of: providing a nasal insert, said nasal insert including a body for insertion into a nasal cavity, said nasal insert body comprising an inner surface defining an air passageway, and an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body is configured to create a bypass of the olfactory region or directs the air and/or odor(s), and/or other substance(s)/particle(s)/signal(s)/element(s)/etc. to bypass the olfactory region thereby delaying, blocking, manipulating, or reducing the amount air and/or odor(s), and/or other substance(s)/particle(s)/signal(s)/element(s)/etc. from reaching to or in relation of the olfactory region and/or redirecting air and/or odor(s), and/or other substance(s)/ particle(s)/signal(s)/element(s)/etc. to other regions of the nasal cavity or is configured to direct air and/or odor(s), and/or other substance(s)/particle(s)/signal(s)/element(s)/ etc. towards the olfactory region; and wherein the redirecting of air and/or odor(s), and/or other substance(s)/ particle(s)/signal(s)/element(s)/etc. and/or the blocking or reducing or manipulation of air and/or odor(s), and/or other substance(s)/particle(s)/signal(s)/element(s)/etc. produces a therapeutic effect.

Also provided herein is a method for alteration of food preferences according to a therapeutic regimen, comprising the steps of: providing a nasal insert, said nasal insert including a body for insertion into a nasal cavity, said nasal insert body comprising an inner surface defining an air passageway, and an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body is configured to create a bypass of the olfactory region or directs the air, and/or odor(s), and/or other substance/ particle(s)/signal(s)/element(s)/any substance/etc. to bypass the olfactory region thereby delaying, blocking, manipulating, or reducing the amount of air and/or odor(s), and/or other substance(s)/particle(s)/signal(s)/element(s)/etc. reaching to or in relation of the olfactory region and/or redirecting air and/or odor(s), and/or other substance(s)/ particle(s)/signal(s)/element(s)/etc. to other regions of the nasal cavity or is configured to direct air and/or odor(s), and/or other substance(s)/particle(s)/signal(s)/element(s)/ etc. towards the olfactory region; and wherein the redirecting of air and/or odor(s), and/or other substance(s)/ particle(s)/signal(s)/element(s)/etc. and/or the blocking or reducing or manipulation of air and/or odor(s), and/or other substance(s)/particle(s)/signal(s)/element(s)/etc. alters metabolic processes thereby promoting healthier food choices and producing a therapeutic or wellness or required effect.

Further provided herein is a method for treating overweight/obesity/morbid obesity according to a therapeutic regimen, comprising the steps of: providing a nasal insert, said nasal insert including a body for insertion into a nasal cavity, said nasal insert body comprising an inner surface defining an air passageway, and an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body is configured to create a bypass of the olfactory region or directs the air and/or odor(s), and/or other substance(s)/particle(s)/signal(s)/element(s)/etc. to bypass the olfactory region thereby delaying, blocking, or reducing the amount of odors and/or other particles reaching the olfactory region and/or redirecting air to other regions of the nasal cavity or is configured to direct air towards the olfactory region; and wherein the redirecting of air and/or odor(s), and/or other substance(s)/particle(s)/signal(s)/element(s)/etc. and/or the blocking or reducing or manipulation of air and/or odor(s), and/or other substance(s)/particle(s)/signal(s)/element(s)/etc. alters metabolic processes thereby reducing the urge to eat and producing a therapeutic effect.

Also provided herein is a method for preventing or treating allergies, comprising the steps of: providing a nasal insert, said nasal insert including a body for insertion into a nasal cavity, said nasal insert body comprising an inner surface defining an air passageway, and an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body is delaying, blocking, or reducing the amount of odors and/or antigen(s), and/or other particles(s)/substance(s)/signal(s)/any substance/etc. being in contact with nasal mucosa, and/or redirecting air to other regions of the nasal cavity or beyond the nasal cavity; and wherein the nasal insert body prevents particles causing allergic reaction from reaching unwanted areas in the nasal cavity or beyond it.

Additionally provided herein is a method for treating and/or preventing over-weight/obesity/morbid obesity according to a therapeutic regimen, comprising the steps of: providing a nasal insert, said nasal insert including a body for insertion into a nasal cavity, said nasal insert body defining an air passageway, and having an outer surface, said outer surface configured to form a seal between said nasal insert body and the nasal cavity; inserting said nasal insert body into the nasal cavity such that the nasal insert body rests against a portion of the nasal cavity wherein the nasal insert body is configured to create a bypass of the olfactory region or directs the air and/or other substance to bypass the olfactory region thereby delaying, blocking, or reducing the amount of odors and/or other particles reaching the olfactory region and/or redirecting air to other regions of the nasal cavity or is configured to direct air towards the olfactory region; and wherein the redirecting of the air and/or other substances alters food choices, and/or reduces eating, and/or increases bodily energy expenditure, and/or enhances or changes an effect on bodily metabolic pathways, and/or directs specific odors/particles to olfactory/brain, and/or enhances an effect of specific particles or odors over the olfactory and brain, and/or alters metabolic processes thereby producing a therapeutic effect.

Further provided herein is a method for preventing weight gain or for supporting weight management and/or weight loss according to a therapeutic regimen, comprising the steps of: providing a nasal insert, said nasal insert including a body for insertion into a nasal cavity, said nasal insert body comprising an inner surface defining an air passageway, and an outer surface, said outer surface configured to form a seal between said nasal insert body and the nasal cavity; inserting said nasal insert body into the nasal cavity such that the nasal insert body rests against a portion of the nasal cavity wherein the nasal insert body is configured to create a bypass of the olfactory region or directs the air and/or other substance to bypass the olfactory region thereby delaying, blocking, or reducing the amount of odors and/or other particles/any substance reaching the olfactory region and/or redirecting air/any substance to other regions of the nasal cavity or is configured to direct air towards the olfactory region; and wherein the redirecting of the air/any substance and the blocking or reducing of odors/any substance alters metabolic processes thereby reducing the urge to eat and/or increasing energy expenditure, and/or otherwise affecting and producing a therapeutic or a wellness effect.

Additionally provided herein is a method for addiction rehabilitation comprising the steps of: providing a nasal insert, said nasal insert including a nasal insert body for insertion into a nasal cavity, said nasal insert body comprising an inner surface or material, and an outer surface or material, said nasal insert body being adapted to fit inside a nasal cavity; inserting said nasal insert body into the nasal cavity such that the nasal insert body rests against a portion of the nasal cavity, creating a partial or full blockage of the nasal cavity; and wearing the nasal insert body for an amount of time, wherein the wearing of the nasal insert body creates a feeling of a mild cold and/or light runny nose, and/or a feeling of sickness or a feeling of disgust and/or less enjoyable or less comfortable experience while attempting to consume an addictive substance, resulting in a reduction or elimination of a user's craving to consume the addictive substance and/or in reduction or elimination of the amount of consumption of the addictive substance.

Also provided is a method for treating diabetes, for alteration of food preferences, for treating allergies, for treating overweight/obesity/morbid obesity for weight management according to a therapeutic regimen, comprising the steps of: providing a nasal insert, said nasal insert including a nasal insert body for insertion into a nasal cavity, said nasal insert body comprising an inner surface or material, and an outer surface or material, said nasal insert body being adapted to fit inside a nasal cavity; inserting said nasal insert body into the nasal cavity such that the nasal insert body rests against a portion of the nasal cavity, creating a partial or full blockage of the nasal cavity; and wearing the nasal insert body for an amount of time wherein wearing of the nasal insert body creates a feeling of a mild cold and/or light runny nose, and/or a feeling of sickness or a feeling of disgust and/or less enjoyable or less comfortable experience resulting in a the relevant improvement.

Further provided is a method of using a nasal insert as described herein for treating of diabetes, prevention of diabetes, preventing weight gaining, treating allergies, alteration of food choices, addiction rehabilitation, reducing consumption of and/or craving to sweet foods, reducing consumption of and/or craving to sugar, reducing consumption of and/or craving to artificial sweeteners, reducing consumption of and/or craving to sweet beverages, reducing consumption of and/or craving to fatty foods, reducing consumption of and/or craving to carbohydrate foods, reducing consumption of and/or craving to backed and pastry based foods, enhancing consumption of and/or craving to healthy foods, altering eating habits towards a healthier diet.

Additionally provided herein is a method for treating weight loss, comprising: providing a nasal insert, said nasal insert including a body for insertion into a nasal cavity, said nasal insert body defining an air passageway, and having an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body creates a partial or full bypass of the olfactory region or directs the inhaled air and/or other substance to bypass the olfactory region thereby delaying, blocking, or reducing the amount of odors and/or other particles reaching the olfactory region by inhalation, and wherein said nasal insert body configured to enable the reach of food or other odors or particles coming from the throat area and/or from inside the body to the olfactory area and wherein the combination prevention/decrease of environmental odors/particles/signals while enabling the reach of odors/particles/signals of eaten foods/ingredients/other particles coming from the area of the throat and/or from other internal organs leads to weight loss and/or prevents weight gain.

Using any of the above mentioned methods, wherein insertion of the nasal insert into the nasal cavity blocks, prevents, reduces, or delays smelling.

Using any of the above mentioned methods, wherein insertion of the nasal insert into the nasal cavity distorts smelling and/or leads to unpleasant flavors and smells.

Using any of the above mentioned methods, wherein the nasal insert contains or comprises a medicine and/or a hormone and/or oxygen.

Using any of the above mentioned methods, wherein the nasal insert contains or comprises an odor and/or a substance affecting the perception of odor(s) and/or flavors.

Using any of the above mentioned methods, wherein insertion of the nasal insert into the nasal cavity changes the perception of existing environmental smells, thereby interfering with flavors and smells, alteration of food choices, and/or improvement of metabolic parameters leading to weight loss.

Using any of the above mentioned methods, wherein the nasal insert is configured to create a pass and/or to block/prevent/reduce access to the olfactory region and/or to other region and directing air and/or other substances towards the olfactory and/or to another region.

Using any of the above mentioned methods, wherein the nasal insert is configured to be positioned in any of the nasal meatuses.

Using any of the above mentioned methods, wherein use of the nasal insert gives a user a sensation of satiation.

Using any of the above mentioned methods, wherein the nasal insert is worn during meal time.

Using any of the above mentioned methods, wherein the nasal insert is worn during sleeping hours.

Using any of the above mentioned methods, wherein the nasal insert is worn during the day.

Using any of the above mentioned methods, wherein the nasal insert is not worn during meal time.

Using any of the above mentioned methods, wherein the nasal insert is worn for providing a therapeutic substance to a target destination.

Using any of the above mentioned methods, wherein the therapeutic effect includes alteration of food choices.

Using any of the above mentioned methods, wherein the therapeutic effect include reduced consumption of and/or reduction of the craving for: sweet foods, and/or carbohydrate foods, fat foods, sugar, and/or artificial sweeteners, and or sweet foods and beverages, and/or fatty foods, and/or, alcohol.

Using any of the above mentioned methods, wherein the method further includes manipulation of smells that leads to mimicking a situation similar to smell distortion.

Using any of the above mentioned methods, wherein the method is modified to treat, instead of or in addition to weight loss, one or more of the following: treating or preventing diabetes, alteration of food choices, treating or preventing allergies, addiction rehabilitation, affecting metabolic related processes, improving metabolic parameters, addiction rehabilitation, smelling prevention, smelling decreasing, decreasing or preventing the effect of environmental bio-chemical signals through the nose while enabling and/or enhancing the reach of internal bodily/foods/particles signals reach through the nose and/or through other channels.

Using any of the above mentioned methods, wherein the method comprises blocking or preventing or reducing or inhibiting or manipulating a molecule, and/or a hormone, and/or a signal and/or any other substance from reaching and/or activating functions related to the olfactory organ or located near the olfactory region or connected to the olfactory region or to other bodily organs which are connected to olfactory.

Using any of the above mentioned methods, wherein the method is modified to treat, instead of or in addition to weight loss, one or more of the following: treating or preventing diabetes, alteration of food choices, treating or preventing allergies, addiction rehabilitation, affecting metabolic related processes, improving metabolic parameters, addiction rehabilitation, smelling prevention, smelling decreasing, decreasing or preventing the effect of environmental and internal bio-chemical and other signals through the nose while enabling and/or enhancing the effect of other internal bodily inputs.

Using any of the above mentioned methods, wherein the nasal insert in use does not comprise a sealing member and does not create a seal.

Using any of the above mentioned methods, wherein the nasal insert in use does not direct/redirect.

Using any of the above mentioned methods, wherein the nasal insert is configured to create a pass and/or to block/prevent/reduce access to the olfactory region and/or to other region and directing air and/or other substances towards the olfactory and/or to another region.

Using any of the above mentioned methods, wherein the therapeutic effect is one or more of the following: a. reducing fat mass, b. reducing fat mass without reducing muscle mass, c. reducing fat mass without reducing fat free mass, d. increasing bodily fat burn, e. increasing bodily energy expenditure, f. reducing insulin resistance, g. reducing blood lipids, h. improving glucose parameters, and i. altering food choices towards healthier diet.

Further, provided herein is a method for treating or preventing diabetes, comprising the steps of: providing a nasal insert, said nasal insert including a body for insertion into a nasal cavity, said nasal insert body defining an air passageway, and having an outer surface; inserting said nasal insert body into the nasal cavity; wherein the nasal insert body is configured to either (1) create a bypass of the olfactory region or direct any substance away from the olfactory region thereby delaying, blocking, manipulating or reducing the amount of the any substance from reaching the olfactory, or being in close proximity to the olfactory region, or to other regions of the nasal cavity or beyond, or (2) wherein the nasal insert is configured to direct the any substance towards the olfactory region, or towards other regions of the nasal cavity or beyond; and wherein the redirection of the any substance, and/or the blocking or reducing or manipulation of the any substance or the olfactory region alters metabolic processes thereby producing a therapeutic effect.

Additionally provided herein, is a method for treating an overweight, obese, or morbidly obese individual according to a therapeutic regimen, comprising the steps of: providing a nasal insert, said nasal insert including a body for insertion into a nasal cavity, said nasal insert body comprising an inner surface defining an air passageway, and an outer surface; inserting said nasal insert body into the nasal cavity; wherein the nasal insert body is configured to either (1)

create a bypass of the olfactory region or direct any substance away from the olfactory region thereby delaying, blocking, manipulating, or reducing the amount of the any substance from reaching the olfactory region, or being in close proximity to the olfactory region, and/or redirecting the any substance to other regions of the nasal cavity or beyond it, or (2) wherein the nasal insert is configured to direct the any substance towards the olfactory region, or towards other regions of the nasal cavity or beyond; and wherein the redirection of the any substance, and/or the blocking or reducing or manipulation of the any substance or the olfactory region alters metabolic processes thereby reducing the urge to eat and producing a therapeutic effect.

Using any of the above methods, wherein insertion of the nasal insert into the nasal cavity blocks, prevents, reduces, or delays smelling.

Using any of the above methods, wherein insertion of the nasal insert into the nasal cavity blocks, prevents, reduces, or delays smelling.

Using any of the above methods, wherein insertion of the nasal insert into the nasal cavity distorts smelling and/or leads to unpleasant flavors and smells, or wherein the nasal insert contains or comprises an odor and/or a substance affecting the perception of odor(s) and/or flavors.

Using any of the above methods, wherein insertion of the nasal insert into the nasal cavity distorts smelling and/or leads to unpleasant flavors and smells, or wherein the nasal insert contains or comprises an odor and/or a substance affecting the perception of odor(s) and/or flavors.

Using any of the above methods, wherein the nasal insert contains or comprises a medicine and/or a hormone and/or oxygen.

Using any of the above methods, wherein the nasal insert contains or comprises a medicine and/or a hormone and/or oxygen.

Using any of the above methods, wherein the nasal insert is configured to be positioned in any of the nasal meatuses.

Using any of the above methods, wherein the nasal insert is configured to be positioned in any of the nasal meatuses.

Using any of the above methods, wherein use of the nasal insert gives a user a sensation of satiation.

Using any of the above methods, wherein use of the nasal insert gives a user a sensation of satiation.

Using any of the above methods, wherein the nasal insert is worn during meal time.

Using any of the above methods, wherein the nasal insert is worn during meal time.

Using any of the above methods, wherein the nasal insert is worn for providing a therapeutic substance, and wherein the nasal insert is positioned in a user such that the therapeutic substance reaches a target destination, thereby providing a therapeutic effect.

Using any of the above methods, wherein the nasal insert is worn for providing a therapeutic substance, and wherein the nasal insert is positioned in a user such that the therapeutic substance reaches a target destination, thereby providing the therapeutic effect.

Using any of the above methods, wherein the wearing of the nasal insert body creates a feeling of a mild cold and/or light runny nose, and/or a feeling of sickness or a feeling of disgust and/or less enjoyable or less comfortable experience resulting in the therapeutic effect.

Using any of the above methods, wherein the wearing of the nasal insert body creates a feeling of a mild cold and/or light runny nose, and/or a feeling of sickness or a feeling of disgust and/or less enjoyable or less comfortable experience resulting in the therapeutic effect.

Using any of the above methods, wherein the therapeutic effect includes alteration of food choices.

Using any of the above methods, wherein the therapeutic effect includes alteration of food choices.

Additionally provided herein is a method for treating or preventing diabetes; or overweight, obese, or morbidly obese individuals; or treatment of addiction, or alteration of food choices; or treating allergies, comprising the steps of: providing a nasal insert, said nasal insert including a body for insertion into a nasal cavity, said nasal insert body defining an air passageway, and having an outer surface; inserting said nasal insert body into the nasal cavity such that the nasal insert body rests against a portion of the nasal cavity; wherein the nasal insert body is configured to either (1) create a bypass of the olfactory region or direct any substance away from the olfactory region thereby delaying, blocking, manipulating or reducing the amount of the any substance from reaching the olfactory, or being in close proximity to the olfactory region, and/or redirecting the any substance to other regions of the nasal cavity or beyond, or (2) wherein the nasal insert is configured to direct the any substance towards the olfactory region, or towards other regions of the nasal cavity or beyond; and wherein the redirection of the any substance, and/or the blocking or reducing or manipulation of the any substance or the olfactory region alters metabolic processes thereby producing a therapeutic effect.

Using any of the above methods, wherein the method treats allergies and the redirection prevents particles causing the allergies from reaching unwanted areas of the nasal cavity.

Using any of the above methods, wherein said outer surface is configured to form an outer surface to form a seal with the nasal cavity when the nasal insert is inserted into the nasal cavity.

Using any of the above methods, wherein the nasal insert body is configured to either (1) create a bypass of the olfactory region or direct any substance away from the olfactory region thereby delaying, blocking, or reducing the amount of or manipulating the any substance from reaching the olfactory, or being in close proximity to the olfactory region, and/or to other regions of the nasal cavity or beyond, and/or (2) wherein the nasal insert is configured to direct the any substance towards the olfactory region, and/or towards other regions of the nasal cavity or beyond and/or to manipulate the any substance in relation to these regions, and/or (3) wherein the nasal insert is configured to manipulating the olfactory, and/or other region in the nasal cavity or beyond.

BRIEF DESCRIPTION OF THE DRAWINGS

FIG. 2A is a side perspective view of a nasal insert made in accordance with the present invention;

FIG. 2B is a side perspective view of a nasal insert and applicator;

FIG. 3 is a front view of a nasal insert made in accordance with the present invention;

FIG. 7A is a cross section of another design of a nasal insert and applicator made in accordance with the present invention;

FIG. 7B is a side perspective view of a nasal insert and applicator made in accordance with the present invention;

FIG. 8A is a side perspective view of a nasal insert showing a rectangular-shaped nasal insert made in accordance with the present invention;

FIG. 8B is a rear perspective view of an L-shaped tail of the nasal insert of FIG. 8A made in accordance with the present invention;

DETAILED DESCRIPTION

Figure 1:
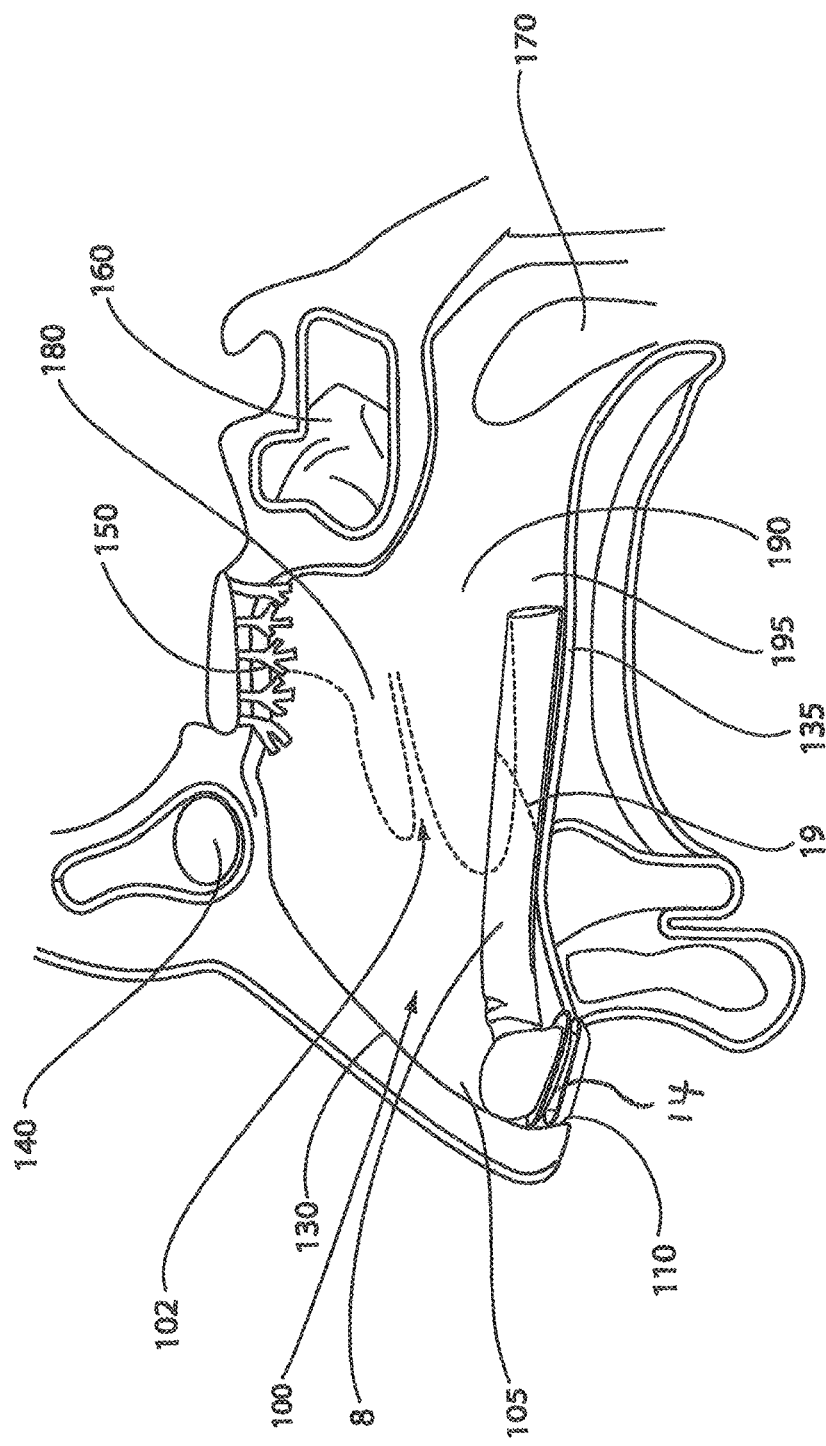
FIG. 1 is a cross section of a nasal passageway having a nasal insert made in accordance with the present invention.

Provided herein are methods for use of odor prevention apparatuses and other apparatuses for: treating and/or preventing diabetes, addiction rehabilitation, alteration of food preferences, treating overweight/obesity/morbid obesity, weight management, improving metabolic parameters, reducing/treating/affecting blood pressure, hypertension, and metabolic disorders, and for the treatment/management of allergies.

These and other features and characteristics of the present invention, as well as the methods of operation and functions of the related elements of structures, and the combination of parts and economies of manufacture will become more apparent upon consideration of the following description with reference to the accompanying drawings, all of which form a part of this specification, wherein like reference numerals designate corresponding parts in the various figures.

All examples and embodiments are meant to be clarifications and are not meant to be limiting to the specific example. Also when referring to "smelling", the term is to be understood broadly. That is, "smelling" in most cases refers to the broader scope of any inputs received by the olfactory organ and region and sometimes to the nasal cavity in general, and is not meant to be limited to odorants-related inputs only.

For purposes of the description hereinafter, the terms "upper", "lower", "right", "left", "vertical", "horizontal", "top", "bottom", "lateral", "longitudinal" and derivatives thereof, shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

An exemplary nasal insert that may be used to achieve the methods described herein is described for example in U.S. Pat. Nos. 8,517,026 and 8,839,790, and as described below. U.S. Pat. Nos. 8,517,026 and 8,839,790 are incorporated herein by reference.

Figure 4:
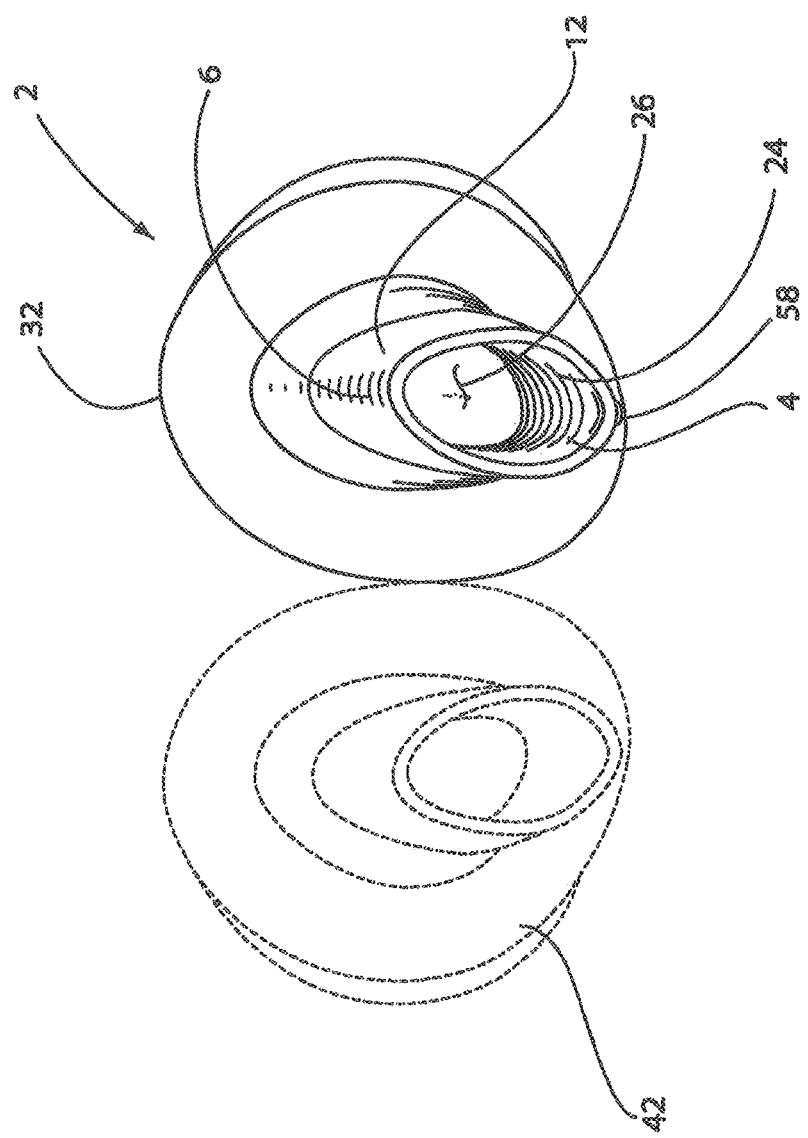
FIG. 4 is a rear view of a nasal insert made in accordance with the present invention.

With reference to FIGS. 2-4, an embodiment of a nasal insert, generally indicated as 2, of the present invention is shown. Further embodiments of a nasal insert are discussed in detail below. Nasal insert 2 is used to prevent odor or to significantly reduce odor particles from reaching the olfactory region in the roof of the nasal cavity, thereby stopping or decreasing smells and flavors. The nasal insert 2, includes a compressible body 8 having an inner surface 4 and an outer surface 6. The inner surface 4 of nasal insert body 8 defines an air passageway 26. The inner surface 4 forming air passageway 26 is rigid and yet flexible, enabling compression and expansion of air passageway 26, while always remembering and aspiring to return to its original shape to maintain an open air passageway. In an alternative embodiment, the inner surface 4 may partially or fully extend into the air passageway 26, such that the airflow through the air passageway 26 is partially or fully obstructed. The nasal insert body 8 will assume the shape of the nasal cavity, which may be different from its original shape, for example (not-limiting), outside of the nose the nasal insert body 8 may be oval, and while in the nose the nasal insert body 8 may be more bean-like or a smooth "L" shape or other suitable shape, the exact shape is not meant to be limiting as other shapes may suit for the required purposes. Also, because the nose conchas may be periodically expanding and shrinking as the user breathes, the nasal insert body 8 and, accordingly, the air passageway 26, are flexible enough to change their shape accordingly. Nasal insert body 8 will be rigid enough not to collapse and will maintain an open airway. The ability of the nasal insert body 8 to compress and expand also minimizes the pressure against the nasal mucosa, providing comfort. As shown in FIG. 3, with like numbers for like parts, the air passageway 26 begins at the upstream opening 22 and continuously extends through the nasal insert body 8 to the downstream opening 24, as shown in FIG. 4. Air passageway 26 of this example extends throughout the entire length of the nasal insert body 8.

The nasal insert body 8 of this non-limiting example further includes an enlarged bulbous-shaped head 14. The shape of the head 14 is non-limiting, as other shapes can also be used, such as for example (not-limiting), a pear, oval, funnel, curved, straight, triangular, rectangular, or rounded head. The nasal insert body 8 may be flexible to adapt to the specific shape of the nasal cavity. The nasal insert body 8 further extends to the end 13 of the nasal insert body 8 and is a substantially slightly curved cylinder having a substantially oval shape. In addition, this extending part can include a tapered tail. The nasal insert body 8 may be flexible to adapt to the specific shape of the nasal cavity allowing a maximal cross section area for air passageway and minimizing pressure over the nasal internal mucosa through the periodical expansion and reduction of the conchas. The shape and size of the nasal insert body 8 or of the area marked as 12 or 10 and of the tail are non-limiting and can vary as other shapes and sizes can be used having similar effects including round, bean, "L" shape, convex, straight, rectangular, curved, tapered, bulbous, or others. Further, The nasal insert body 8 can also have a slanted tail 18 or a bulbous shaped tail 37 similar to the head 14 as shown in FIG. 2B, forming a large bulbous tail for gently leaning against the nasal septum of the nasal cavity 100.

In this example when the nasal insert body 8 is inserted into the nasal cavity 100 as shown in FIG. 1, the nasal insert body 8 can be positioned inside the nasal vestibule 105 of the nasal cavity 100, so that the nasal insert body rests fully, and/or partially against a portion of the nasal cavities, forming a seal between the nasal insert body 8 and the nasal walls, and allowing air to pass through air passageway 26 while blocking air from passing around it. The air passageway 26 may be created solely by the inner surface of the device or by a combination of the device and the nasal cavity organs. For example (non-limiting) by a combination of the inner surface of the nasal device body 8 and the nasal floor serving as a part of the air passageway. By moving through air passageway 26 the air is conducted to the posterior nasal cavity bypassing the olfactory area 150 located in the uppermost part of the nasal cavity. Nasal insert body 8 can also have a shortened tail 19 (shown in phantom), in which case air is still bypassing the olfactory region 150 because it is directed past. Thus, air passageway 26 of the nasal insert body 8 prevents air from reaching an olfactory region 150, either by bypassing the olfactory area 150 or by directing the air to bypass the olfactory area. The sense of smell originates in the nasal passageway. Odor particles stimulate the olfactory region 150 of the human nose. Nasal cavity 100, as shown in FIG. 1, includes a nostril 110, an upper nasal wall 130, a frontal sinus 140, and an olfactory region 150. The olfactory region 150 is covered by bipolar sensory neurons leaving the nose through the cribriform plate in the nasal roof synapsing in the olfactory bulb at the base of the frontal lobe of the brain. It is estimated that in the olfactory region 150, there are around six million sensory cells bilaterally. The olfactory senses reach the olfactory cortex in the rhinocephalon (not shown). Olfaction requires nasal air flow, which is part of respiration. The nasal cavities 100 further include nasal sinus 160 and nasopharynx 170. Also shown are the nasal conchas 180, 190. The inferior meatus 195 is located between the inferior concha 190 and the nasal floor 135. During normal respiration, most of inhaled air runs through the inferior and middle meatuses 195, 102 and only 10-15% of the inhaled air flows through the olfactory region 150 in the upper part of the nasal cavity 100, where odor is sensed. The specific route in which air goes into the nasal cavity 100 will determine which part of the air will come in contact with olfaction cells of the olfactory region 150. The air passageway 26 directs air to bypass the olfactory region 150 of the nasal cavity 100. By bypassing the olfactory region 150, odorous particulates are prevented from reaching that olfactory region.

In this example, to insert the nasal insert body 8 into the nasal cavity 100, the user can first compress the insert body 8 by squeezing it between the user's fingers. In addition, an applicator 44, shown in phantom in FIG. 2B and in cross section in FIG. 7A, can hold, squeeze and assist navigating the nasal insert body 8 and aid in preventing it from folding. The user can also just push the nasal insert body 8 into the nostril 110 and the nasal cavity 100 without compressing the nasal insert body at all.

Next, the user can then push the nasal insert body 8 into the nostril 110 and into the nasal cavity 100 to the inferior meatus, meaning between the inferior turbinate and the nasal floor, the area marked as 12 being placed first inside the nostril 110. As shown in FIG. 1, when the nasal insert body 8 is inside the nasal cavity 100, the bulbous head 14 is positioned to form a seal of the nasal vestibule inside the nasal cavity 100. A seal is produced between the head 14 and the nasal vestibule in the nasal cavity 100, forcing air to move in and out only through the air passageway 26 that bypasses the olfactory region 150 or directs the air to bypass the olfactory region 150. The seal that is formed in the nasal vestibule is not meant to be limiting as it may be formed in other locations at the nasal cavity, for example, at the nasal valve, and serve the same function. Also, the positioning at the inferior meatus is the preferred positioning, but other locations may be used, for example, the middle meatus. The seal formed between the head 14 and the nasal cavity, or elsewhere between the nasal insert body and the nasal cavity, also enables the formation of an air lock inside the nasal cavity 100. By forming an air lock inside the nasal cavity 100, stagnant air blocks new air from entering and, therefore, air is stopped or reduced from circulating inside the nasal cavity 100. Exhaled air from the rear of the nasal cavity is blocked or delayed from entering by the stagnant air remaining in the nasal cavity. Air circulation is stopped or significantly restricted when the air lock is formed. Thus, when an air lock is formed, it either prevents or significantly decreases odor from reaching the olfactory region 150. In addition, in case of a reduced, but yet existing circulation, the air lock delays the arrival of odor to the olfactory area.

In the preferred embodiment of the present invention, the user preferably inserts one nasal insert 2 into each nostril. In an alternative embodiment, the user may insert the nasal insert 2 into only one nostril. In such an alternative embodiment, the user benefits from the herein described advantages of the present invention, while retaining the ability to smell. The nostril(s) having a nasal insert 2 inserted therein will have, for a period of time, an increased secretion of nasal mucus as well as a partial blockage of the nostril, while the nostril without the nasal insert 2 will not. The user might, therefore, experience the symptoms commonly associated with a mild cold which, in turn, may assist in overcoming certain periods of addiction rehabilitation, and may assist in initiating processes of altering food choices and other aspects of different treatments. The device can be combined if necessary and if relevant with medications such as for example (not limiting) sedatives or benzodiazepine medications, or other relevant medications to ease with the withdrawal symptoms.

In addition to the above-described effects, the present invention also has the effect of blocking part of the nasal cavity and also increasing the secretion (and/or creation or generation) of mucus in the nasal cavity. The presence of the nasal insert body 8 inside the nasal cavity 100 causes such a phenomenon, thereby making the user feel as if he/she has a mild cold. This phenomenon and also the general use of the device daily may provide significant aid in different addictions' withdrawal symptoms to assist in the initial most physiologically difficult (and sometimes mental also) stage of rehabilitation, (it may also aid in other treatments). For instance, some people tend to eat less sweets while having a runny nose. Another example is from alcoholics people: it has been found that many people who drink alcohol report having nasal/sinusitis congestion that leads them to significantly reduce alcohol consumption or to quit drinking alcohol all together. Also they sense less the smell and flavor of the drink. By increasing the secretion of mucus in the nasal cavity, or by blocking part of the nasal cavity, the nasal insert body 8 creates a similar feeling of nasal congestion/runny nose/mild cold/sickness etc. that may lead to the desired effects for different treatments. For example (all examples are non-limiting): assist in alcohol or other addiction rehabilitation, assist in reduced sweet consumption, assist in rehabilitation from sweet foods/from fattening food/from fatty food or foods in general, from drugs (for example non limited: cocaine, heroin, grass, some medications). Another example is that in some cases the use of drug while having the sensation of runny nose (sniffing drugs or others) may lead to sensation of sickness or disgust or unpleasant in general. In simulating the symptoms of a mild cold, the present invention significantly reduces or entirely eliminates the user's impulse or general desire to consume many addiction related items, and also assists in treating other situations. The user remains healthy in all other respects and has no other symptoms of illness. In addition, the fact that the nasal insert is in the nasal cavity may create a situation where the respiration through the nose is a bit slower than usual. As a result, addictive people who are inclined to exhale through their nose for having the full experience (for example—with drugs addiction—smoked or sniffed or other) will experience discomfort in maintaining this practice. This discomfort associated with the user experience, further aids in helping the user suppress or eliminate the urge to consume the addictive "ingredient" and quit or significantly reduce its consumption. This discomfort also helps in treating/managing diabetes, obesity, blood pressure issues, hypertension, metabolic disorders, helps in promoting the alteration of food choices, in addiction rehabilitation, improvement of metabolic parameters, and allergies. It is hereby clarified, that the above mentioned effects, and the use of the nasal insert can provide a significant aid also beyond the initial adaptation period and beyond the initial withdrawal symptoms, by using the device.

In addition to the above-described effects, the present invention also may have the effect of enlarging the nasal natural air passageway. The nasal valve is the narrowest air passageway of the upper respiratory system and it generates a large part of the overall natural nasal resistance to air flow. The nasal insert of this invention, in the relevant measure for such application, may force a larger cross section for air flow in the nasal valve area and contribute to easier breath in general as well as to reduction or elimination of snoring or of obstructive sleep apnea. In other words, the nasal insert passageway 26 cross section area or effective diameter over the complete passageway length is larger than the cross sectional area or effective diameter of the nasal valve when the nasal insert 2 is not placed within the nasal cavity. It may also assist athletes, students or any other person who needs increased air consumption and oxygen for a specific need, or in general.

The nasal insert body 8 can be formed of one or more materials, and is primarily a soft, flexible, and in some cases, spongy body 8. The outer surface 6 of the nasal insert body 8 can serve the important purposes of absorbing mucus and facilitating the run-off of mucus. In addition the outer surface 6, or part of it, can be used for forming a seal between the nasal cavity 100 and the nasal insert 2 and for sealing the nasal insert itself, or to support backward drainage of the mucus. In the first case, when the outer surface 6 is used to absorb mucus, materials that are primarily absorbent can be used to form the outer surface 6 or part of it. Absorbent materials that can be used include, for example, cotton, hydro-gels, Merocell®, polyethylene glycol, types of polyurethane or polyvinyl chloride, any type of suitable foam or any other suitable materials or combination of materials. The type of material is not meant to be limiting. A sealant material can also be used on the outer surface 6 of nasal insert 2 to seal the nasal insert 2. The sealant material can block odors and also facilitate mucus to run-off away from first end 11 toward a second end 13 of the nasal insert body 8 and into the nasal cavity 100. Materials suitable to form a strong seal can include silicon, Tygon®, any other plastic or combinations thereof, or any other suitable materials. In the case of forming a seal between the nasal cavity and the nasal insert, both absorbent or non-absorbent materials can be used, for example, cotton, hydro-gels, Merocell®, polyethylene glycol, silicon, any type of polyurethane, polyvinyl chloride, Tygon®, and other suitable materials. The outer surface 6 can be compressed or altered for smoother insertion, gaining a larger size after being placed in the nasal cavity. The inner surface 4, which forms the air passageway 26, can be made of a more rigid material that is also flexible and elastic in order to enable the air passageway 26 to expand and remember its original shape after it has been compressed or altered in some way. The material of the inner surface 4 may be selected to enable insertion of the insert without folding in cases when the applicator is not used. Examples of suitable materials include silicon, Tygon®, types of plastic or any combinations or suitable material. Between the inner surface 4 and the outer surface 6, any number of additional layers can be included to form nasal insert body 8. Each layer of nasal insert body 8 materials can include spongy material, sealant material, absorbent material, antibacterial material, alternative odor, anti-pollutions, or medicine, including but not limited to, hydro-gels, silicone, Tygon®, cotton, Merocell®, silicon, polyurethanes, polyvinylchloride, dimethylpolysiloxan, silicic acid, azodiacarbonamide, reticulated foam, polyethers, polyesters, polysiloxanes, polycarbonate, polyolefins, polybutyrates, polyethylene teraphtalate (PET), Polymides, polyethylene glycol, activated carbon, biodegradable material, anti-microbial agents, plastic materials, silver, bamboo, antimony, aluminum, metal materials, polymers, wood, resins, carbon based materials, carbon nanotubes (CNT), esters, also can be used for achieving different effects such as rigidity, or manipulation of different signals or other, may be of different metals, magnetics, optics and others as suitable. The particular type of material used for the layers of the nasal insert body 8 is not meant to be limiting.

Alternatively, air passageway 26 can be filled or partially filled with a porous material to absorb odors, or for other uses, air can be allowed to pass through, and the porous material can trap or neutralize odorous particles. In yet another alternative of the preferred embodiment, the air passageway 26 can be filled with a material that completely or partially obstructs the airflow through the air passageway, thereby compelling the user to increasingly breathe through the mouth. The inner surface 4 and the outer surface 6, as well as any layer between them, can be partial layers or combinations of partial layers and full layers and/or full layers only or any other combination. On the other hand, they can all be made of the same material and/or be one layer, as long as the structure and material support the characteristics of softness, rigidity, flexibility, and others as defined above and hereinafter. In lieu of a passageway, the nasal insert can be made entirely of a porous material. In an embodiment where the air passageway is at least partially obstructed, respiration through the nose is less comfortable and slower than usual. The rigidity and the softness of the inner and outer surface can be the same.

In some embodiments the outer surface 6 can include a sealant material formed only on the head 14 of the nasal insert body 8, the nasal insert body 8 or part of it can be made of absorbent material, with a sealing layer throughout the inner surface 4. The sealing layer of inner surface 4 can limit odor and other particles/substances/materials/signals etc. from penetrating the nasal insert body 8 and reaching the olfactory region 150, while the absorbent outer surface 6 reduces mucus and the sealant head 14 blocks air from flowing around the device and directs it. The sealing layer and the absorbent layer of the nasal insert body 8 or of part of it can be the same layer and material. Alternatively, the nasal insert body 8 can be made of only one material, such as silicon, when the rigidity, softness, flexibility, resilience and other characteristics may be achieved by different thickness, stiffness, resilience, shape, grooves and other manageable parameters.

The nasal insert 2 can also be used to deliver odors or other materials or signals etc. To deliver odor, the nasal insert body 8 can be made of natural materials or artificial materials, such as esters, which have inherent odor, or where odor can be added to the insert material. Alternatively, the materials of one or both of the inner and/or outer surfaces 4, 6 or any other layer of nasal insert body 8 can be impregnated with odorant particles or coated in order to deliver odor. For example, any surface of the nasal insert body 8 may be impregnated with any flavor commonly associated with tobacco or tobacco-like substances. Also, odor can be applied to the relevant element by an external tool such as an applicator or by immersing the device in an odorant material prior to insertion or by other relevant means.

In addition, the nasal insert 2 can provide medication. In such a case, medicine can be coated on one or both of the inner and outer surfaces 4, 6 or on another layer of the nasal insert 2, or can be applied to it through an external applicator. Alternatively, the materials of one or both of the inner and outer surfaces 4, 6 or any other layer of nasal insert body 8 can be impregnated with medicine or coated in order to deliver medicine. Also, antibacterial materials such as nanoscale silver or silver ion or bamboo or medicine can be used when making the composition of the nasal insert body 8, or coated thereon or added in any other relevant manner to the device at any stage of use as will be relevant for the specific application.

With reference to FIGS. 2A and 2B, nasal insert body 8 can include a flexible sealing member 30 in order to create a tight seal between the nasal insert body 8 and the nasal cavity 100. Sealing member 30 can be an outward extending leaf from head 14 of the nasal insert body 8 of the nasal insert 2. The sealing member 30 can be a convex shaped leaf extending outward from the outer surface 6 of the head 14 of the nasal insert body 8. The flexible yet rigid properties of sealing member 30 are adaptable to form a tight seal between the nasal insert body 8 and the nasal cavity 100 when the nasal insert body 8 is placed into the nasal cavity 100. The sealing member 30 may have spring characteristics and also is positionable to provide a corresponding match to the internal contour of the nasal cavity 100. The sealing member 30 can seal the nasal vestibule 105 and direct the inhaled air through the air passageway 26 of nasal insert 2. The sealing member 30 can provide an absolute seal and assure all nasally inhaled air will enter the air passageway 26 through the nasal insert 2. The sealing member 30 can also form an air lock after the nasal insert 2 is inserted into the nostril 110. The sealing member 30 can also be located in a different place on the nasal insert body and can have a different shape. The specific location and shape are not meant to be limiting as many can serve the purpose.

Multiple sealing members can be attached to the nasal insert body 8. As shown in FIGS. 2A and 2B, a second sealing member 32 can be placed on the head 14. The second sealing member 32 can be adjacent to the first sealing member 30, extending outward from the outer surface 6 of nasal insert body 8. The second sealing member 32 combines with the first sealing member 30 to create better sealing and to better form an air lock after the nasal insert 2 is placed in the nostril 110. A third sealing member 34 (shown in phantom) can extend from the outer surface 6 of the nasal insert body 8 or of the area marked as 12. A fourth sealing member 36 (shown in phantom) can extend along the nasal insert body 8 or the area marked 12 or any other part of the nasal insert body 8. Additionally, as shown in FIG. 2B, nasal insert body 8 can have a bulbous tail 37 (shown in phantom) having an optional sealing member 38 thereon or different sealing members. The number and placement of sealing members is not meant to be limiting, as different combinations can be combined to create a desired airflow to block or prevent or reduce or delay odor or other substances/signals etc. from reaching the olfactory region, and also from the nasal mucosa as relevant for the specific application.

A sealing member can also be formed of layered material on the nasal insert body 8. For example (non-limiting), the head 14 can have sealing material attached on its surface to define a sealing member of material. The sealing material can be shaped to provide characteristics of the sealing members. On the other hand, it can be made with no additional layer or specific sealant member by suitable shape of the nasal insert body 8. In addition, any of the sealing members discussed can alternatively be partial sealing members as there is no requirement to completely surround the nasal insert body 8. The air lock can be formed in the upper nasal cavity.

Figure 5:
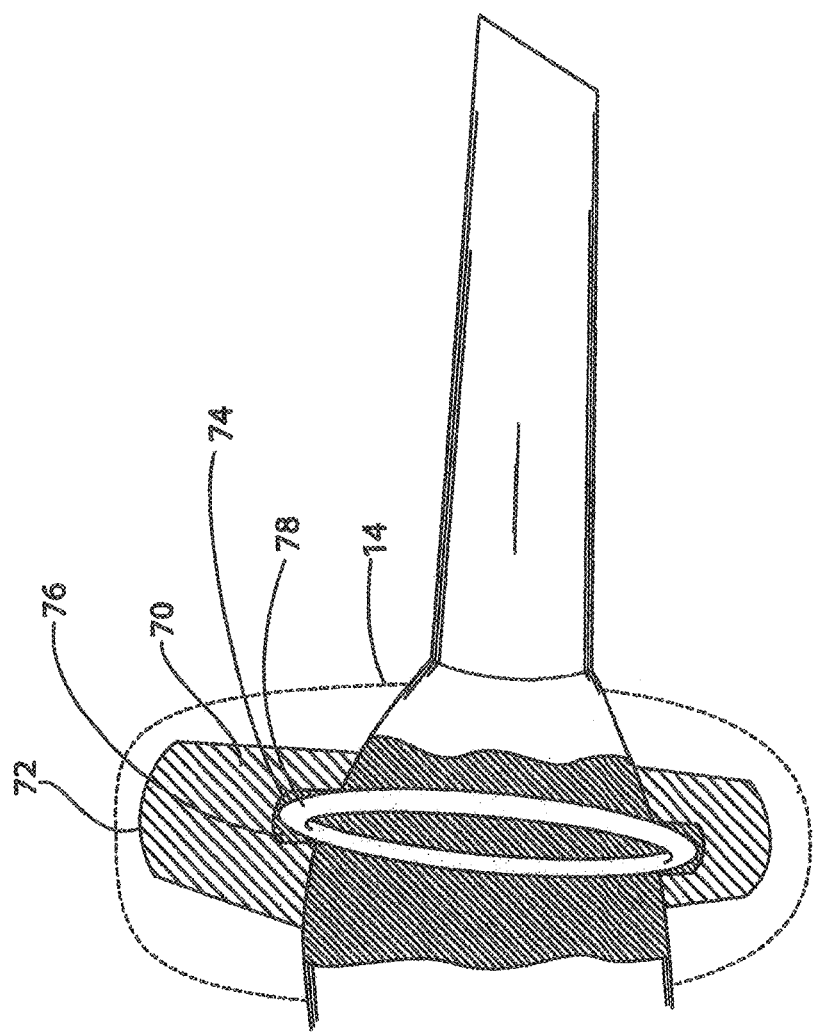
FIG. 5 is a side cross section of a nasal insert in accordance with the present invention.

With reference to FIG. 5, nasal insert body 8 is shown having an alternative sealing member 70. Sealing member 70 extends from head 14 and includes an inner surface 74 and an outer surface 72 forming a sealing member extending outward similarly to that of sealing member 30; however, an inner surface 74 of sealing member 70 forms a groove 76 that may receive a ring member 78, or may alternatively receive a spring member (not shown), or remain empty. When a ring member 78 is inserted in groove 76, the sealing member 70 is stretched and strengthened and can form a tight seal between the sealing member 70 and the nasal cavity 100. The ring member 78 can be replaced when it becomes loose or if the nasal insert body 8 is to be removed. The outer surface 72 can be made from a different material than the inner surface 74 or of the nasal insert head 14. The material can be absorbent or non-absorbent. The cavity formed by the inner surface 74 is also a grip, enabling the material of the outer surface 72 to be mechanically connected to the internal surface 74 and to the nasal insert head 14 or body 8 in general. The outer surface may fully or partially surround the head and may also form different shapes (shown in phantom). The method and materials of sealing, sealing members and their connectivity to the nasal insert portions is not meant to be limiting, as many different alternatives may be applied to perform the sealing. For example, instead of having a bulge as a grip, a niche, pin or some adhesive material can be used (not shown), and other methods and materials of sealing are possible. Also, all of this mechanism can be located elsewhere on the nasal insert body 8.

Referring back to FIGS. 2A and 2B, a nasal insert body 8 may further include a flexible joint 40 defined by grooves 40' and 40" formed in the nasal insert body 8 and shown between the first portion 10 and second portion 12 or as part of a device having only one portion, or as a joint of other portions of a device comprises several portions (using the example and the description of having first portion second portion and alike is not meant to be limiting, but meant to ease in explaining the drawings and sometimes to serve as an example). The flexible joint 40 is formed by a groove or series of grooves defined through all or part of the layers comprising nasal insert body 8. The groove or series of grooves may be located between the first and second portions 10, 12 of the nasal insert body 8 or in other locations on the nasal insert body 8 or between other portions if exist or as part of single portion device. The flexible joint 40 provides increased flexibility and can minimize the effect of movements of one nasal insert portion in regard to the other nasal insert portion to provide higher comfort. The increased flexibility can further minimize pressure against the nasal mucosa; the flexible joint 40 provides flexibility for the second portion 12 or other portion/s to bend with relation to the area marked 10 or to other relevant portions or add greater flexibility to a single portion device or within a single portion(s). Flexible joint 40 provides flexibility when navigating and inserting the nasal insert 2 into the nasal cavity 100. Still further, facial expressions which move the nose can be buffered in their effect on the nasal insert body 8 as the nasal insert 2 can flex at the flexible joint 40 to accommodate the movements. The flexible joint 40 is optional as embodiments with different joints or without high flexibility joints at all may serve as well.

FIG. 3 shows a right and left nasal insert 2, 42 (shown in phantom). When inserted into the nasal cavity, the nasal inserts 2, 42 can fit and be oriented for the left and right nasal cavities, respectively.

Figure 6A:
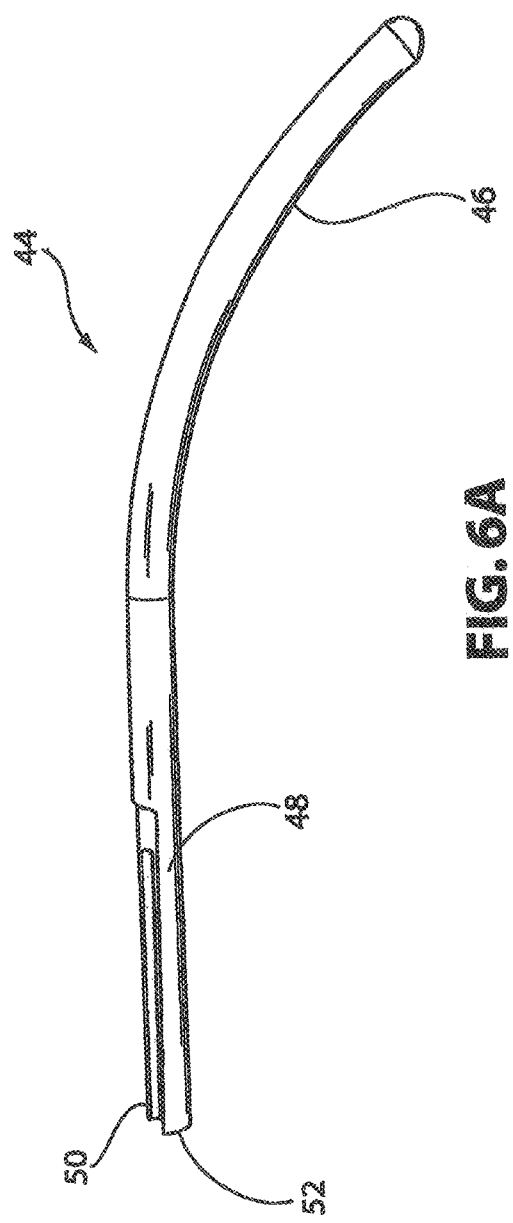
FIG. 6A is a side perspective view of an applicator made in accordance with the present invention.
Figure 6B:
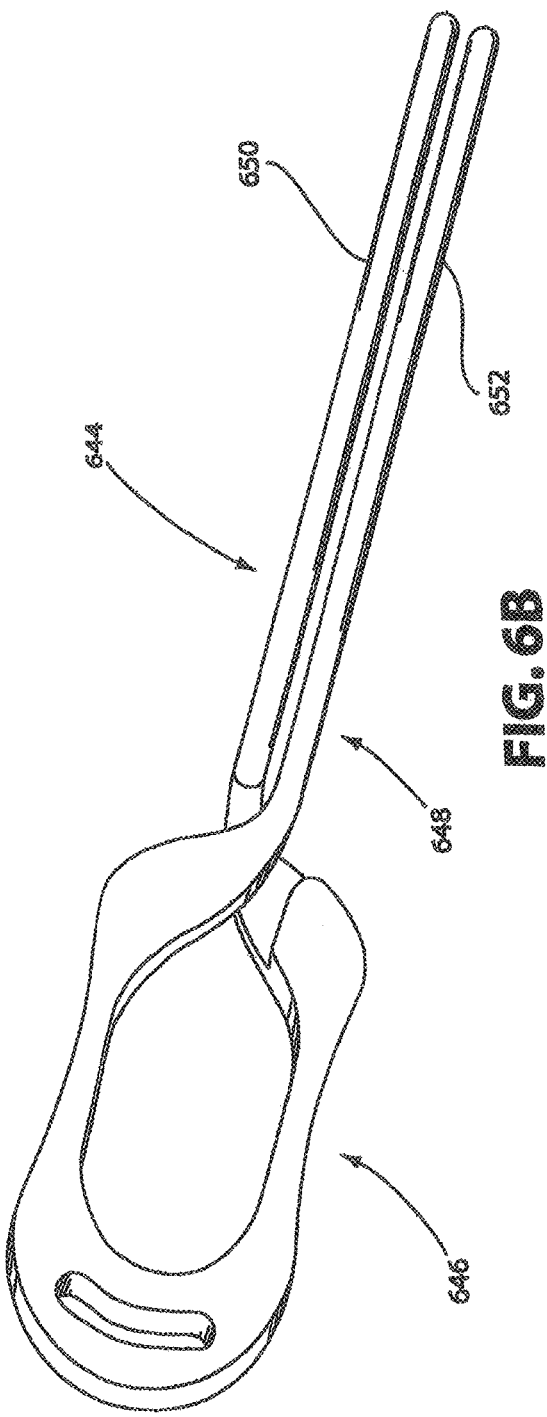
FIG. 6B is a side perspective view of an applicator that is made in accordance with the present invention.

With reference to FIGS. 6A, 6B and 7A, an applicator body 44 includes a holding region 46, a gripping mechanism 48 that may be comprised of forks or scissor-like arms, or other suitable mechanism 50, 52 for gripping and/or squeezing the nasal insert body or for conducting other relevant activities, such as applying an odorous material or medicine. The applicator 44 can be used to insert a nasal insert, or for various other applications such as, for example, removing the nasal insert, applying an odorous material or medicine, expanding the nasal insert, pumping liquid, air or other material, or positioning a nasal insert. The flexibility of the nasal insert body 8 in general, and along the area marked as 12 in particular, can enable both manually compressing the nasal insert body 8, as well as compression with an applicator 44. In addition, a flexible region 54 may be defined on the nasal insert body 8 enabling collapsing through compression in a determined area and also providing higher comfort.

With reference to FIGS. 6A, 7A and 7B, the applicator 44 may be connected to the nasal insert body 8 by having the forks 50, 52 of applicator body 44 gripping the gripping area of the nasal insert body. When the forks 50, 52 are pressed further onto the flexible region 54 of nasal insert body 8, or to other relevant areas of nasal insert body 8, they create a squeezing action compressing the nasal insert body. Flexible region 54, or the other pressed part of nasal insert body 8, in turn applies frictional resistance against the forks 50, 52, thereby retaining the applicator 44 until it is manually removed. Alternatively, FIG. 6B shows an applicator body 644 having scissor arms 650, 652 that can grip the gripping portion of the nasal insert body 8, or other part, and hold the nasal insert body squeezed using the flexibility and compressibility of the nasal insert shape and materials. The applicator, in general, may further include a stopper (not shown) for preventing insertion of the insert too deep into the nose for safety purposes. In addition, a stopper may also be added to stop the fork/scissor-like arms or other relevant part of an applicator from sliding off of the gripping portion of the nasal inset body 8 when they are connected. The applicator shape and the correlated method of gripping and compressing are not meant to be limiting, as other methods and shapes may be applied. In addition the applicator may further allow reduced rigidity along the nasal insert body 8 in general, and along the air passageway 26 and the area marked 12 in particular, as the applicator will prevent the nasal insert from folding through insertion. Gripping portion, such as 58, and/or flexible area, such as 54, can also be applied to the nasal insert body 8 of the nasal insert body 8, allowing smooth comfortable insertion of the head 14 as well. The use or presence of an applicator is not meant to be limiting as many embodiments that do not use any applicator can serve as well. Also, the presence of a dedicated flexible area is optional as the nasal insert body can flex without it. For example, the nasal inserts shown in FIGS. 2A and 2B have a gripping portion 58, but do not have the flexible area 54. FIG. 7B shows a compressed nasal insert body 8 with an applicator body 44 connected.

Alternatively, the fork/scissor-like arms, or other relevant mechanism, may grip the gripping portion of the nasal insert body 8 and hold the nasal insert body squeezed using the flexibility and compressibility of the nasal insert shape and materials or by causing a collapsing in a different designated flexible area along the nasal insert body 8. A gripping region 58 of the nasal insert body 8 may further act as a guide for insertion. The shape of the gripping portion 58 is not meant to be limiting, as other shapes can be applied for the same purpose, for example, the gripping portion as shown in FIGS. 2A and 2B. When the applicator 44 is connected to the nasal insert 2, the forks 50, 52 may hold the nasal insert in a squeezed position. The use of fork or scissor-like arms or another relevant mechanism for gripping the nasal insert body 8, or for squeezing and expanding it, or for any other use of the applicator is not meant to be limiting as many other mechanisms may perform these functions. The nasal insert body 8 may further include a gripping area. With reference to FIG. 7A, the gripping area 58 will be held by an applicator 44. The applicator 44 may also squeeze the nasal insert body 8, allowing the nasal insert body 8 to pass easily into the nasal cavity 100. The forks 50, 52 are retained on the gripping area of the nasal insert body 8 by a combination of restive pressure and the whole gripping region 58, and will remain in place until the user pulls the applicator 44 out from the nasal insert 2. The applicator shape and the correlated method of gripping and compressing are not meant to be limiting, as other methods and shapes may be applied.

The applicator 44 can navigate the nasal insert 2 into the nasal cavity 100 and can also be used to adjust the nasal insert 2 inside the nasal cavity 100. In addition, the applicator 44 can compress and open the nasal insert 2 when inserting and also removing the nasal insert 2. Nasal inserts can be offered with or without an applicator. Applicator 44 can be made of a rigid and sturdy but yet elastic material such as plastic, metal and rigid silicon. The applicator 44 can be more rigid than the nasal insert 2, thereby allowing the nasal insert 2 to be navigated by the applicator 44. The type of material is non-limiting, as other materials can be used to make the applicator 44.

Additional embodiments are shown in FIGS. 8A, 8B, 9, 10 and 11. FIG. 8A shows an embodiment of a nasal insert 202 having an enlarged rounded rectangular shaped head 214 in arear marked 210 and an L-shaped tail 216 in the area marked 212. The enlarged rounded rectangular shaped head 214 is surrounded with a bulge 220 that can be used as a grip for another layer, or as a sealing member, or as a groove for a spring and can also provide flexibility inside the nasal cavity 100 to expand into the nasal cavity 100, forming a tight seal within. An optional layer 218 can be made of absorbent or non-absorbent material providing better sealing and higher comfort and can fully or partially cover the walls of the head 214. With reference to FIG. 8B, the tail 216 of nasal insert 202 can be formed of an "L" shape and forms an L-shaped air passageway 226 therethrough. The "L" shape suits the internal natural nasal cavity shape.

Figure 9:
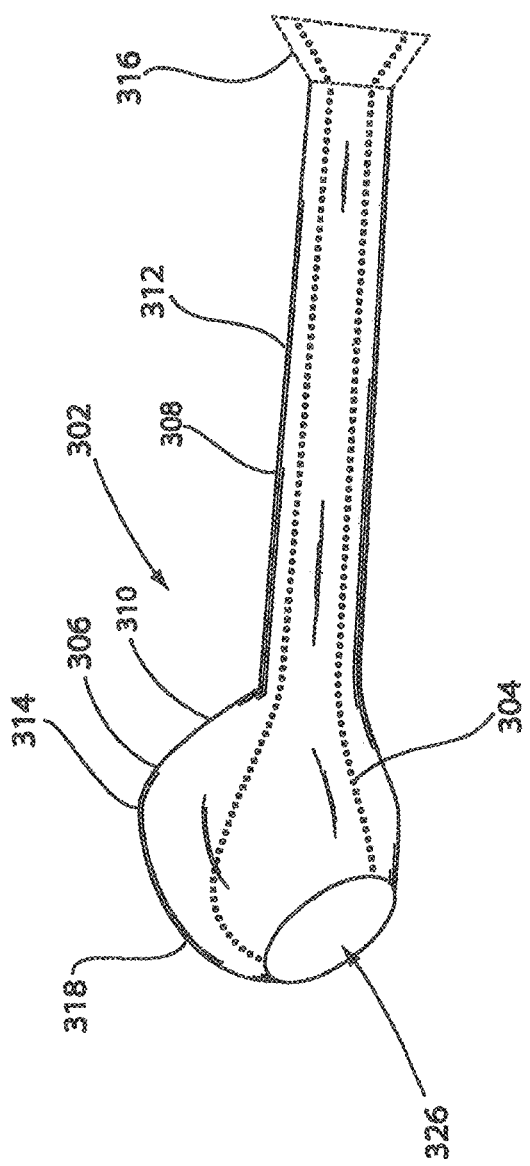
FIG. 9 is a side view of a nasal insert having a bulbous head and a flared second end shown in phantom made in accordance with the present invention.

FIG. 9 shows a flexible nasal insert 302 having a wider bulbous round head 314 and a thinner area marked 312. The air passageway 326 has a wider air passageway in the area marked as 310 and it narrows through the area marked as 312. The outer soft surface can be made of absorbent or non-absorbent compressible or non-compressible material, and the inner surface more rigid but elastic. Also, the inner layer can be made of sealed material preventing odor particles from moving through it, thereby compelling the user to breathe through the mouth. The air passageway 326 enables easier movement of air through the nasal insert 302. The nasal insert 302 can be positioned in the nasal cavity and the head 314 will form a snug fit with nasal vestibule 105 internal walls and block the air from flowing around the head directing it into the air passageway 326. The air passageway 326 may bypass the olfactory area or direct the air to bypass the olfactory area.

Alternatively, the surface 318, or the entire outer surface 306, of the nasal insert 302 can be made of a high density sealing material or an additional layer of high density sealing material can be placed on a first layer of spongy or porous material or the outer surface covering it fully or partially. The high density material can prevent any inhaled or exhaled air from reaching the olfactory region 350 of the nasal cavity 300 and contributes good drainage of the mucus.

Alternatively, air passageway 326 can be fully or partially filled with material, or the whole device can be made of porous material. In this case, the nasal insert body 308 can be fully or partially covered with a sealing layer.

Alternatively, the insert does not seal with the nasal cavity and air can flow around the insert.

With continuing reference to FIG. 9, the length and other characteristics of the nasal insert 302 or of any other possible embodiment of a suitable nasal insert (shown or not shown herein) can be varied by increasing and decreasing the length of the nasal insert body 8 and also area 312 and other areas, as well as other characteristics of the reference device. The nasal insert 302 can also include a tail 316 (shown in phantom). Tail 316 directs the exhaled air to move out more easily through the nasal insert body and directs it into the air passageway and by that assists in preventing it from the olfactory region 150. It also supports the formation of an air lock in a sturdier manner and contributes to preventing or significantly reducing the amount of odor substances, signals etc. from reaching the olfactory area.

Figure 10:
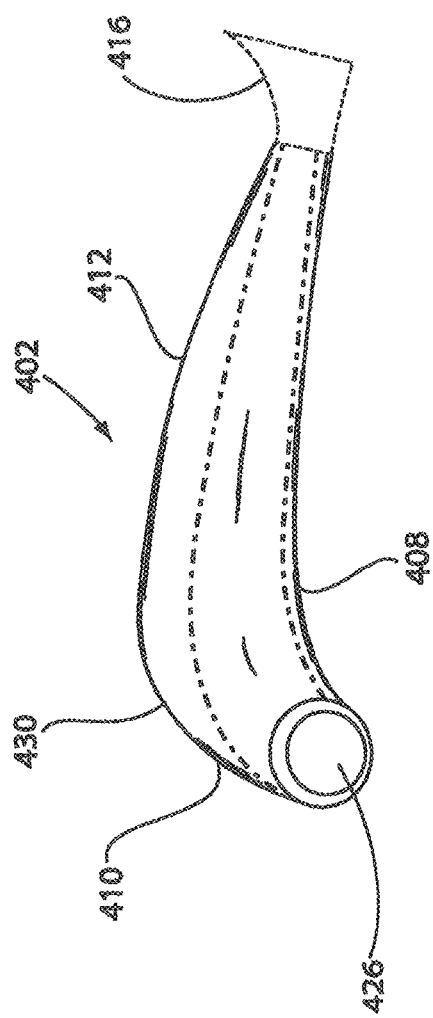
FIG. 10 is a side view of another design of a nasal insert made in accordance with the present invention.

FIG. 10 shows a nasal insert 402 having an alternative convex shape. Nasal insert 402 having an area marked as 410 and a curved body 408 and curved air passageway 426 therethrough. The curve of nasal insert body 408 can fit nasal cavity 100. The nasal insert body 408 and region between area 410 and the area marked as 412 can use layered material to form a sealing member 430 that can press against the nasal cavity 100 forming a tight seal. A tail 416 (shown in phantom) can be included having a wider air passageway in the area marked 412 to aid respiration and direct exhaled air into the air passageway more easily, and to better form the air lock that assists in preventing odor and other substances and/or signals from reaching the olfactory area.

Figure 11:
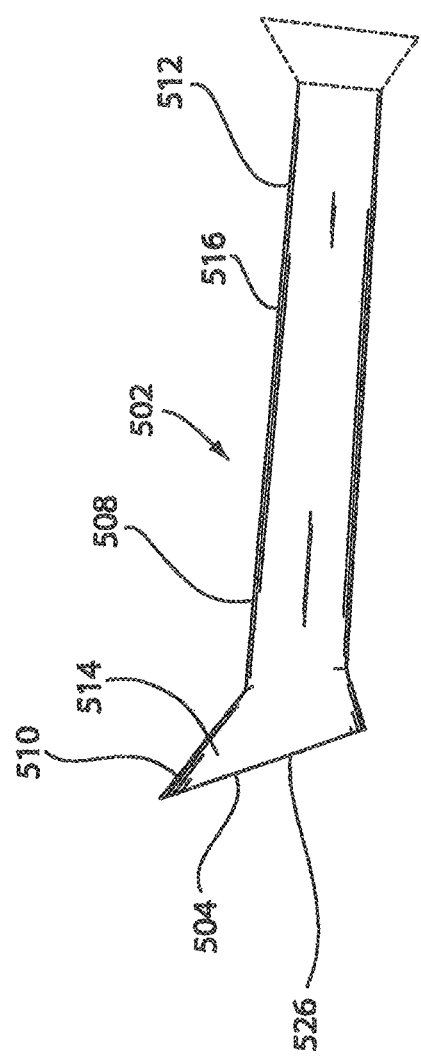
FIG. 11 is a side view showing a nasal insert having a flared head made in accordance with the present invention.

FIG. 11 shows a nasal insert 502 having a nasal insert body 8 having a flared head 514 and a tail 516. The inner surface 504 defines an air passageway 526 through the nasal insert 502. The air passageway 526 can remain constant, decrease or increase in width or can change in shape. The tail 516 can decrease in width or remain constant, or increase from the area marked as 510 to the area marked as 512. The length of the tail can vary and the shape of it as well, such as flared tail, non-flared tail, oblique general length, and the like.

In some instances, the present invention provides a method for reducing or eliminating the urge to consume the addictive ingredient in general by suppressing the body's physiological desire to consume it in many aspects, for example: the desire to consume such ingredient instigated by perceiving smells in general or by specific smells (or other olfactory inputs) which are connected to the user's habits associated with the addictive ingredient or general experience. For example, many alcoholic people may be urged to drink wine after smelling, food, other peoples' wine or other smells. It may also suppress the physical desire to consume the addictive element by physically preventing/reducing different molecules from reaching the olfactory/brain/blood stream/CNS via the nasal cavity and activating the expected reaction to the addictive substance. For example by preventing/reducing the access to olfactory it may also block/reduce the access to receptors located in the olfactory/brain and prevent/diminish the hedonic response or other response created by their activation/excitation, another example is that the device will block/prevent/reduce other signaling channels that are activated via elements in the nasal cavity or by elements that are connected to the nasal cavity in some manner, like the neuronal transmission of signals. Meaning the device may function similarly to antagonists of the receptor(s), or as inhibitors of activation/excitation of the receptor(s), or as inhibitors of the signaling pathways activated in response to activation/excitation of the receptor(s). It may also suppress the physical desire to consume the addictive element by causing the user to have a reaction of sickness and/or disgust while trying to consume it or while being in an environment with people who consume it or even cause repulsion from thinking about consuming it. This physical reaction leads to the outcome that the invention is also enabling addictive people to smoothly overcome, with very little struggling, the challenging period of defeating the physical addiction to the addictive element, when the body is cleaning itself from it. In some embodiments. The present invention also flattens the consumption experience and makes it flavorless. In addition, for some cases, the present invention suppresses/alter consumption and the urge to it by causing the user to feel disgust and sickness while trying to consume it, as if he/she had been ill. While using the invention, the user might feel like he/she is experiencing some symptoms of a mild cold and slight runny nose without actually being ill or without experiencing other illness symptoms such as fever. In addition, the invention may create additional discomfort while actual trying to consume while using it, when used in cases in which exhalation through the nose or consumption through the nose (like sniffing for example) are part of the experience as exhalation may be slower than usual or blocked, and inhalation will also have very different effect with different devices. For example: by using a device that bypasses olfactory and minimizes the contact of air/sniffing ingredient with the nasal lining—the drug/other addictive element will be prevented or significantly reduced from olfactory and brain, and from blood dream, which will prevent/reduce/change the entire experience. Also in that case significant part of the drug may end up in the stomach or outside the nose or in other areas and lead to different phenomenon. For severe addiction situations or other relevant medical or non-medical situations, there might be a benefit in attaching the device permanently—meaning without having the user being able to remove it by himself/herself for a period of time. The invention may also support addictive people, people suffering from diabetes and other illnesses and conditions' efforts to avoid gaining weight while quitting his/her addictive behavior, may also help improve/reduce/treat/affect blood pressure or hypertension, or while receiving a treatment that may lead to weight gain (such as beta blocker medications, steroids and other treatments), as it affects the metabolic cycle and craving of foods in a very strong manner and shall causes the user to eat less and less often, and due to all other related phenomenon in relates to the devices metabolic affect and other related aspects. In addition, in some embodiments this invention may cause a flat and less enjoyable addictive ingredient consumption experience due to weakening smelling. First, a nasal insert 2, as shown in FIG. 2A, is provided having an air passageway 26. The nasal insert 2 is inserted into the nostril 110 and into the nasal cavity 100. The nasal insert 2 can be inserted, as previously described hereinabove, by pressing the nasal insert body 8 between two fingers of the hand, or by using an applicator, or in any other suitable manner, or it can be compressed in the first place. The user can lift the hand with the nasal insert 2 up toward the nose and under the nostril 110. The user then pushes the nasal insert body 8 into the nasal cavity, and one nasal insert can be inserted through each of the right and left nostrils and directed into the nostril 110 with the user's fingers or by using an applicator. Using the fingers or an applicator 44, as shown, for example, in FIG. 2B, the adjustment of the nasal insert 2 can be made. The user can position the nasal insert body 8 to fit snuggly inside the nasal cavity 100. In alternative embodiments, a premolded liquid or body temperature activated insert or an insert premolded with an applicator, can be provided, which can be inserted into the nose and pushed inside the nasal cavity. Once inside, the mucus and bodily fluids or external dropping of liquid or body temperature or other relevant act, such as, for example, manually turning or opening the applicator can activate the premolded nasal insert 2 to decompress inside the nasal cavity 100 and expand into the nasal cavity 100 forming a tight but comfortable fit. The premolded nasal insert 2 can also be activated using an applicator 44 having liquid thereon which can be placed on the nasal insert body 8, or by applying some other act to the nasal insert. A nasal insert that does not require the above process, is applicable as well. For example, a nasal insert, which shape is fixed, can simply be pushed into the nasal cavity to the right position, adapting its flexible body to the nasal internal anatomy (or being suitable at the first place) without the need of changing shape due to body temperature, liquid etc. Once inside the nasal cavity 100, the head 14 of the nasal insert 2 can stretch and form a comfortable fit and also block inhaled air from passing around the nasal insert 2 and thereby directing the inhaled air to pass in through the air passageway 26. Sealing members 30, 32, 34, 36 and 38 of FIGS. 2A and 2B, or others, can also aid in forming a seal and blocking air, thereby directing the air through the nasal insert air passageway and/or forming an air lock in nasal cavity 100. When the user begins breathing after inserting the nasal insert body 8, the inhaled air is directed into the air passageway 26 and through the nasal insert body 8 to the respiratory passages of the user. Exhaled air or air simply coming from inside the body for example (non-limiting) from the mouth, is also directed into the air passageway 26 and out through the head 14 of the nasal insert body 8. This direction of air creates a bypass of olfactory region 150 and in doing so, prevents or significantly reduces or delays or manipulates odors and other substances molecules and/or signals/other inputs from reaching the olfactory region 150. Alternatively, the insert can be configured to direct air/specific inputs to the olfactory region. By preventing the odors and other substances molecules and/or signals from reaching the olfactory region 150, any odor and/or other substance molecule and/or signal that is related to the treatment is also inhibited. Taste and smell are physiologically interdependent and distinct flavors are produced by aromas stimulating olfactory chemo-receptors in the olfactory area. Basic taste is perceived by gustatory papillae in the oral cavity and throat, but this sensation is limited to sweet, bitter, sour and salty.

More complex flavors such as wine or chocolate ones are elaborated by smelling odorous particles (and maybe other inputs/substances) coming in contact with the olfactory area. Therefore, this invention in its preferred embodiment flattens all the odor related experience and makes it less flavorful and less enjoyable by reducing or eliminating one's sense of smell. Also it may prevent from other relevant particles from reaching the olfactory and brain and by that create the desired effect. For example: prevent from nicotine reach the Nicotinic acetylcholine receptors (nAChRs) in the olfactory or brain, or prevent from the tryptophan in chocolate, that is a precursor to serotonin from reaching it and by that may aid in reduction of chocolate craving or ease it or prevent it, or it may aid in the prevention of signals or related molecules resulting in cravings or from sweet things from being transmitted from the tongue or from other sources to olfactory and related areas such as brain areas. In addition, smelling receptors are connected directly to the cortex and brain organs and different smells may lead to the creation of an instinct and sometimes uncontrolled desire to the addictive ingredient/element, which leads to impulsive consumption of the addictive ingredient/element. Similarly, may activate other substances and signals via olfactory. By eliminating or reducing or manipulating one's sense of smell/olfactory region and/or nasal inputs, this invention assists the user to avoid or significantly reduce impulse to consume the addictive ingredient/element. Often, addictive people are urged to consume the addictive ingredient/element simply by associating a particular smell, such as the smell of coffee, food or second-hand smell related to addictive ingredient/element from other users/consumers, with the activity of consuming it. By suppressing other smells and/or other related signals/molecules from reaching the olfactory region 150, the present invention additionally reduces impulse consumption caused by sensing other smells/olfactory inputs and responses. Because the perception of odors/other olfactory inputs in the user's vicinity is substantially reduced or distorted or otherwise manipulated, the user is unable to associate those smells with the addictive element, and is thereby less likely to have a desire to consume it. The reduction/manipulation of smell/other olfactory related or nasal related inputs and responses also may results in a flat flavorless, and generally less enjoyable or specifically unpleasant, experience once the user consume the addictive substance or to have and/or establish an automatic unpleasant/repulsive conditioned reaction to the addictive element or to related things. The invention and methods of blocking/reducing or manipulating of molecules/substances/things in relation to olfactory/brain/blood stream inputs and reactions, according to the specific embodiment used, may, therefore, cause the user to be less inclined to consume it or to generally consume it less or to lead him to a state in which he will not want to consume it at all. Even when the user has already started consuming the addictive substance, he/she may not finish the whole course due to the use of the invention, and will reduce or quit using it as well.

Furthermore, the reduction in actual consumption of the addictive substance and in the desire to consume it is additionally achieved through the increased secretion of mucus in the nasal cavity or from the creation of the symptoms similar to a mild cold. The desire to consume the addictive substance can also arise from seeing or smelling other people who consumed it or associating it with a particular activity. For example, an alcoholics may have an urge to drink alcohol when socializing with other people who drink, or by talking on the telephone or any other habitual activity. The increased secretion (and/or creation or generation) of mucus in the nasal cavity, as well as the partial blockage of the nasal cavity, make the consumption of some of the addictive substances uncomfortable and even repulsive for the user, and, therefore, causes the user to reduce or totally quit using it. This phenomenon also reduces or even eliminates the user's desire and urge to consume the addictive element in general. Continuous daily use of the nasal insert 2 leads to the elimination of the urge to consume addictive materials triggered by associating it with a particular activity, and enables the user to have a period of time to establish a new routine, or even the same routine that will not be associated with consuming the addictive substances. The use of the nasal insert in the first and most difficult period of addiction rehabilitation efforts will assist the user in going through this period much more easily and to establish a way of life without the addictive element.

One of the most difficult barriers to overcome while attempting to rehabilitate from addiction is the addiction to the very specific ingredient/s that in the addictive element that causes the body to become dependent on it—for example the ingredient "alcohol" from the wine or the nicotine of a cigarette. The present invention can be helpful in assisting the addiction rehabilitation process in this aspect as well. Generally, the presence of addictive ingredient in the addicted person's blood system or brain is eliminated after a period of not consuming it. This period and the few weeks after it are often the most difficult for most addicts attempting to quit because of the sudden withdrawal of the addictive ingredient from the blood system/body/brain. Many addicts who have been unsuccessful in rehabilitating attribute their inability to quit to this initial period. The nasal insert 2 also assists in the aspect of recovering from the addiction by making the consumption of it uncomfortable and unpleasant. This repulsion leads to the elimination of the addictive ingredient from the body without the necessity to depend on will power or to struggle against the physiological need for the addictive ingredient. Such transition is less difficult for the addict person because he/she does not experience the urge for the addict ingredient due to the repulsive reaction/ the runny nose sensation that caused by the present invention, and also due to the fact that it physically blocks the access of the addictive element to the relevant receptors/ sensors in the olfactory/brain/CNS that generate the related response—for example—pleasure/relaxation/dopamine release etc. The physical blockage is due to the device (as explained in the specification) and may also be enhanced by the "runny nose" simulation caused by it. Furthermore, the present invention may be used in conjunction with other known addiction rehabilitation aids, such as medications, and other means. When continuously used according to instructions for several weeks, or for a different period of time, and according to the relevant instructions, which is suitable for this purpose, the nasal insert 2 contributes to the total elimination of the addictive ingredient from the user's body, and to acclimation of the user's body to living without the need for of the addictive ingredient. The nasal insert 2 thereby smoothly and completely eliminates the user's dependence on the drug. The present invention may further comprise written instructions describing how the nasal insert 2 is to be used. The instructions may comprise information on how the nasal insert 2 is to be used in overcoming addiction.

To remove the nasal insert 2, the user can push air out sharply while wiping the nose, by sneezing very strongly, or snorting outward through the nasal cavity 100, causing the nasal insert 2 to fall forward through a nostril 110 from where it can be pulled completely out of a nasal cavity 100. It can also be removed by pushing it out through the nose by gently squeezing the lower part of the nose from outside or by inserting a finger into the nasal vestibule and pulling it out. Further, the nasal insert 2 can be pulled out using the applicator 44. Still further, threads can be attached to the nasal insert body 8 for pulling the nasal insert 2 out of the nasal cavity 100. The method of removal is not meant to be limiting, as many methods will work. Alternative inserts of varying shapes and sizes, as described hereinabove, can be removed in a similar method.

Once the nasal insert body 8 has been used, the user can either clean the nasal insert body 8 and use it again, or can dispose of the nasal insert body 8, depending on the specific material and embodiment, and of other parameters, such as medical instructions of use. One indication that the nasal insert body 8 should be replaced is mucosal saturation on the nasal insert body 8 in case of absorbent material. The nasal insert can be used continuously for a period of time, subject to the relevant limitations, such as materials, medical, supporting addiction rehabilitation instructions, treating/preventing diabetes, altering food choices, treating allergies, preventing weight gain, reducing/treating/affecting blood pressure, hypertension, metabolic disorders, and others. Instructions can be provided defining a period of time that the nasal insert body 8 can be used, for example, a period of several hours before removing to allow the nasal mucosa to rest, or for other reasons. It may also include recommendations and instructions regarding using one or two nasal inserts each time, depending on the desired effect or on other considerations. Alternatively, the nasal insert body 8 can be used only when the user is close to relevant odors/substances/signals or when the user is going to be in a situation that may lead him/her to consume addictive substances, or unwanted foods (sweet or others), or in an area which is with particles causing allergies etc. and he/she would like to avoid it or while the user is sleeping, when the user wishes to avoid or reduce snoring or obstructive sleep apnea, or it can be used while concentrating and studying for a test, etc. The specific occasion and method of use is dependent upon the desired effect, as well as of medical and material parameters, and on other relevant considerations. The nasal insert body 8 can be made in a long lasting format which is reusable, or, alternatively, it can be made in disposable format allowing one or only a few uses before disposing. In an alternative disposable model, biodegradable materials can be used to make the nasal insert body 8. When re-using the same nasal insert body 8, it is recommended that it is cleaned before the re-use.

When the nasal insert body 8 is inserted inside the nostril 110, the nasal insert 2 can be worn without or almost without visual detection from the outside of the nose. Alternatively, the nasal insert 2 can include decorative elements or attachments, such as nose rings and jewelry (not shown), or the nasal insert 2 can be colored and extend beyond the nostril up to the outer side of the nose and/or down towards the mouth or towards the septum and the middle of the nose or other. The direction or specific shape or method are not meant to be limiting as many alternatives may serve. In yet a further embodiment of the present invention, the nasal insert 2 can be a nasal cover and be worn outside the nasal cavity. In this embodiment, the nasal insert 2 is preferably secured to the exterior of the nose and it either partially or fully blocks the passage of air into the nasal cavity. In an embodiment where the air passageway is at least partially obstructed, respiration through the nose will take place at a much reduced rate. As a result, users who are inclined to exhale the through the nose while consuming an addictive substance or other un-wanted substance will experience discomfort in maintaining this practice. This discomfort further aids in helping suppress or eliminate the urge to consume un-wanted substances and to less enjoy it in general. The user may apply the nasal insert externally on the nose by a friction fit or adhesive means, or by tying it to the ears or by many other methods. The specific method is not meant to be limiting as many methods may be applied.

As described before, in addition to all the above, the nasal insert 2 of this invention can be used for reducing and preventing snoring. The nasal area of the respiratory mucosa is particularly sensitive to changes in the blood flow and when congested, it produces a partial or total blockage in the air passages. When a person is in a supine position, for example, when sleeping, the nasal congestion usually produces a partial blockage of the nasal airway. To overcome this blockage, an increase of negative pressure is required to maintain nasal respiration. The increase of negative pressure in the nose, together with muscle relaxation at sleep, will produce vibrations of the soft palate, which is the most common mechanism that causes snoring. By introducing the device into the nasal air passages, an open airway is achieved at the nasal level. Therefore, used during sleep, the device will reduce or eliminate the snoring produced when sleeping in a supine position by maintaining open air passages at the nasal level. In this case, the method of use would be wearing the device in one nasal cavity, or in both nasal cavities, just before sleeping in order to have it while sleeping and taking it out upon waking. In many cases, the use in one nasal cavity will be enough, but in order to achieve a stronger impact, the use in both nasal cavities would be preferred.

In addition, the nasal insert 2 of this invention may be used for reducing and/or preventing obstructive sleep apnea. The same mechanism which increases negative pressure in order to maintain respiration when lying down is responsible for the obstructive sleep apnea in most people suffering from this symptom. The obstructive sleep apnea is caused by collapse of the pharyngeal walls into the airway. This is produced by the combination of increased negative pressure in the air passages during respiration, while the person is in a supine position, and the relaxation of the pharyngeal muscles during sleep. The collapse of the pharyngeal walls will produce a partial or total blockage of air passages at the level of the oropharynx. By maintaining an open nasal passage, the nasal insert reduces the negative respiratory pressure, which eliminates the main cause of air passage collapse at the pharyngeal level. Hence, the nasal insert will reduce the severity or eliminate obstructive sleep apnea. Also, the present invention is a method of use of the nasal insert 2 which can be inserted into one nasal cavity, or in both nasal cavities, just before sleeping in order to have it while sleeping and then taking the nasal insert out upon waking. In many cases, the use of the nasal insert 2 in one nasal cavity will be enough, but in order to achieve stronger impact, the use of nasal inserts 2 in both nasal cavities would be preferred.

In addition to the above-described effects, the present invention also may have the effect of enlarging the nasal natural air passageway. The nasal valve is the narrowest air passageway of the upper respiratory system and it generates a large part of the overall natural nasal resistance to air flow. The nasal insert of this invention, in the relevant measure for such application, may force a larger cross section for air flow in the nasal valve area and contribute to easier breath in general as well as to reduction or elimination of snoring or of obstructive sleep apnea. In other words, the nasal insert passageway 26 cross-sectional area or effective diameter over the complete passageway length is larger than the cross-sectional area or effective diameter of the nasal valve when the nasal insert 2 is not placed within the nasal cavity. It may also assist athletes, students or any other person who needs increased air consumption and oxygen for a specific need or in general. It is understood, that the blockage/reduction/manipulation abilities of the device in regards to the olfactory/part of nasal lining/CNS etc. contributing to reduction in actual consumption of the addictive substance and in the desire to consume, can also be achieved by blocking molecules or hormones or signals from reaching receptors present in the nasal cavity, or cell surface receptors or other receptors/hormones/neurons/nerves/channels/cells/etc. that are accessible via the nasal cavity and by that interfere with their activity or manipulate it. For instance, by blocking receptors, the receptors are unable to interact with or bind to its activating agent, such as an agonist or hormone etc. and the device acts as antagonist or inhibitor for such acts and signals. In addition the device can prevents/reduce the reach of molecules/signals etc. or otherwise manipulate them.

Provided herein are methods and apparatuses, for treating and/or preventing diabetes and/or reducing the risk for developing diabetes, and/or for help living well with diabetes, for alteration of food choices, for addiction rehabilitation or relief, for treating overweight/obesity/morbid obesity, and/or for weight management, helping achieving weight loss goals, treating hypertension/blood pressure and cardiovascular related problems and reducing risk for it, for treating/preventing/reducing the risk for/help living well with allergies, or for any other relevant medical or non-medical treatment or use that can be done using the above device for odor prevention/preventing smelling/decreasing smelling, for olfactory manipulation, for treatment delivery or prevention etc. as described herein and for any other relevant medical or non-medical treatment or use that derives from it.

Addiction Rehabilitation: Olfactory is the only sense that is physically directly connected to the limbic areas in the brain without being relayed to the cortex first. Smell is known to produce reflex and immediate reactions and to have an impact on craving and on memories and is related to reward and addiction. Therefore, craving and relapses can be caused by smells and maybe other substance (any substance) that reach olfactory or reach the limbic area via olfactory (for example: of foods, of alcohol, of drugs, hormones, pheromones, and any other) and interfere with, and impose substantial obstacles to addiction rehabilitation. It is therefore reasonable to assume that decreasing or preventing or manipulating smelling (and generally olfactory related inputs and acts) may result and may assist in a relief from the relevant addiction, and may ease the "rehabilitation". Such addictions may be of any type, for example (but not limited to), food addiction, sugar/sweet addiction, carbohydrate addiction, alcohol addiction, cocaine, heroin and other drugs and medications addiction, nicotine addiction, cigarettes, addiction, sex addiction, computer (games, or other related) addiction, Internet/social network addiction, chocolate addiction and any other. Also another support to the above addiction relief/rehabilitation capabilities, is our findings from our clinical study point to the same direction: reduced consumption of sugar and reduced consumption of alcohol. Sweet and alcohol are both related to the same addiction and reward mechanism: in our clinical trial conducted with an odor prevention/decreasing device that was made out of silicon for this embodiment and provided blockage/reduction/inhabitation of other substances/signals from olfactory region, and a control group that did not use the device-participants in the study arm reported consuming significantly less sugar, less artificial sweeteners and less sweet beverages relatively to the control, there was also significantly reduction in alcohol consumption for one of the study arm's subgroups (relatively to the corresponding subgroup at the control arm). By preventing, decreasing, weakening, and/or otherwise manipulating smelling (and olfactory related activity) it is possible to treat or contribute to treating addictions or at least ease the persistence of a person in a relevant rehabilitation program. The addiction rehabilitation capabilities is also one of the contributors to some other treatments. For example: rehabilitation from food addiction may contribute to or result in weight loss/fat loss. Another example would be: rehabilitation from addiction to sweet may result in reduced sugar and sweet food and beverages intake including artificial sweeteners, and may contribute to or result in prevention or in treatment for diabetes, rehabilitation from alcohol or drug and may result in stop drinking, and so on.

Specifically for smoking quitting, it is known that nicotine receptors are physically located in the olfactory organ and are modulated (weakens) smelling once excited. It is our belief that this is the reason why smokers have reduced smelling capacity and this might be the cause for them being relatively lean. Many smokers do not quit, or they tend to return to smoking after quitting, due to the weight gain associated with smoking quitting. It is believed that this weight gain is associated with the fact that once a smoker cease smoking he/she starts to smell better. Using the device may provide a relief from the weight gain issue in smoking cessation, since it prevents/weakens smelling (similar in that to the situation caused by nicotine) and by that it may contribute to increased motivation in smoking quitting and to higher rates of success. Also, the device may block the access to these nicotine receptors in the olfactory and brain or may be used for providing medications that work with such receptors in the olfactory and brain to assist in smoking cessation. Regarding working with medication, current existing medications for smoking cessation have side effects of stomach pain, gas, vomiting, nausea, indigestion and others. By adapting such medications to be delivered using the nasal device most such problems will be reduced as will not go directly through the digestive system.

Also, for addiction rehabilitation including smoking cessation, the use of any type of smelling blunting or smelling decreasing of other odors, by any means for the purpose of smoking cessation and addiction rehabilitation of drugs, may be used. Such as using the device in addition to covering gels or odors to block olfactory sensors, or to be affecting olfactory and brain related.

Preventing, treating or assisting in diabetes: The mechanism for diabetes treatment/care, might be as follows: the olfactory area in the nose is physically connected to the hypothalamus in the brain, and it physically comprises receptors of metabolic related hormones, such as, Leptin, Ghrelin, GLP1, Insulin Adiponectin and others. The levels of hormones in the brain and plasma are changing in response to enormous amount of parameters. Once smelling in the nose is inhibited it may shut down or interfere with the regular metabolic cycle as well as other bodily cycles, in a very comprehensive way.

Also, it is known that olfactory cells exist not only in the nose but also in many internal organs, for example in the kidneys in the gut in the heart, and in the blood. These olfactory internal cells are assumed to be functioning as sensors managing "input/output" bodily decisions and other activities. Based on the above, it is our belief that olfactory cells in the nose may serve as the main bio-chemical interface and sensor of the brain and hypothalamus with the environment, including with foods' odors: environmental and in the mouth, that are reaching the nose, and including other environmental and bodily internal inputs. Once smelling/sensing in the nose is inhibited or otherwise olfactory mechanisms are being manipulated it may shut down or interfere with the regular metabolic cycle in a very acute manner, since it blocks the hypothalamus' sensors from the relayed environmental and from some of the internal chemical related inputs metabolic and non-metabolic (food, sex-pheromones, alcohol and many others). In this aspect, the hypothalamus (and brain in general) may then remain with other internal food/metabolic/sugar/addiction/hormonal/ other related signals, coming from internal olfactory cells or via other channels to dominate the related functionality (metabolic cycle and many other mechanisms). Meaning, that preventing/decreasing smelling/olfactory inputs or manipulating it and/or the respective reactions, may lead to a comprehensive change in several regular mechanisms such as: cycle of hunger and satiation, cycle of sugar level management, sexual attraction and fertility related management, alcohol and drugs and others. In other words, the role of the odor preventing nasal device may also be used to manipulate the levels of hormones and other signals in the brain. This ability of the device is currently almost impossible to do by other means. As explained, preventing/ blunting/decreasing/manipulating smelling and/or olfactory related inputs in general may lead to an acute change in the regular cycles of the body—for example: of hunger and satiation, of craving and others. In the area of diabetes care this may contribute in several manners: 1. Alteration of food choices towards a healthier diet. I have observed this in our clinical trial as well as from other scientific evidence; 2. Change of levels of related hormones in the plasma, in the brain and in other organs of the body. For example, insulin, GLP1, leptin and others. In the clinical trial conducted with odor/olfactory preventing/decreasing device, the study group had a significant reduction in insulin and in the Homa Insulin while the control group did not (and the difference between groups showed a trend). In addition, GLP1, smelling and diabetes are known to have tight connection, and other related hormones as well. Also, GLP1/GLP1 Receptor is specifically connected to secretion and synthesis/creation of insulin and to neuro transmission of sweet signal. By blocking and/or by reducing the access to GLP1 receptor in the olfactory/brain it is possible to manipulate and/or affect sweet consumption and/or insulin sensitivity and insulin secretion and synthesis. For example (not limiting) it may lead to blockage/reduction of the transmission of GLP1 molecules from the mouth to olfactory (that are secreted there in taste buds in response to sweet foods) and by that prevent/inhibit transmission of sweet signal to specific areas in the brain. Or it can be manipulated to increase sensitivity of the GLP1 receptors and by that contribute to increased insulin sensitivity. Furthermore, there is evidence that alteration in smelling leads to different and healthier food choices, such as less sweet, less fried foods more vegetables and others.

It is believed that inhibiting/blocking/reducing smelling/olfactory may enhance the protective effect that the body is naturally trying to produce in many cases by reducing smelling) capabilities of people suffering from diabetes, obesity and others. These people sometimes tend to have reduced smelling capacity, although many times they tend to have increased sensitivity particularly to food odors/inputs. This invention and related methods may enhance the body's natural intention and aid in providing more effective and comprehensive odor and other substances/signals/inputs prevention/reduction/inhabitation/manipulation to olfactory as well as other olfactory related manipulations, in order to protect the body and assist curing.

The following description provides methods for treating and/or preventing diabetes (which is in addition to the described above and in other paragraphs of the specifications):

1. Wearing the device and preventing/decreasing smelling for different uses: the intended use of treating diabetes, prevention of diabetes or assisting in it and/or in living well with diabetes, and also wearing the device and preventing/decreasing smelling for alteration of different hormonal aspects. In this regard a sealing member, as described in detail above, can also be formed of layered material on the nasal insert body. By preventing and/or decreasing smelling and/or other olfactory related inputs, treating and/or prevention of diabetes, achieving fat loss and weight loss is possible. Weight loss and/or fat loss is related to treating and preventing diabetes and also to treating overweight/obesity/morbid obesity, and for preventing weight gain caused by and/or for supporting weight loss and/or fat loss during processes or treatments that may lead or contribute to "weight gaining" or to difficulties in weight loss. for example (not-limited): smoking quitting, addiction rehabilitation, resolve of nasal/sinusitis congest, using related anti depression medications, taking steroid based treatment, β-blockers based treatments, some of insulin based treatments and many others. Overall, wearing the device can promote individuals to make less fattening food choices, less sweet food choices, less fatty food choices, and in general healthier food choices. Wearing the device to improve reduce/treat/affect blood pressure, hypertension, and/or metabolic disorders. Wearing the device to improve metabolic parameters, such as: Homa Insulin Resistance, Insulin, GLP1, Leptin and others. Or to affect other hormonal aspects or other aspects for these or for other uses. Such prevention/blockage/reduction form olfactory may relate as explained to environmental inputs and to internal inputs for example from mouth/throat/lungs/exhalation to olfactory. Another manner of the method of use would be using the device to prevent/decrease the reach of environmental odors/particles/substances/inputs to the olfactory but to enable/encourage/promote the reach of odors/particles/substances/molecules/signals/inputs created by eaten foods through the process of chewing/swallowing or otherwise coming via the throat/pharynx/lungs or via blood stream into nasal mucosa or otherwise reaching to olfactory in the nose internally from the body. In other words, for example (non-limiting), directing inhaled air to bypass olfactory area, or preventing smelling/olfactory inputs of inhaled air in other manner, and enabling the odors/signals/substances/etc coming through the mouth and going up by the process of swallowing in the pharynx to reach olfactory and to enhance satiation/or otherwise affect. This can be extended to enabling general inputs to nose olfactory coming from internal organs via for example esophagus/trachea etc. This can be achieved in several manners, for example, but not limited to, by one or some of the following: 1. using an odor preventive nasal device embodiment with a bit shorter air passageway. In other words, a device that goes beyond the nasal valve and directs air to bypass olfactory, while also enabling more circulation of air created by the sharp movement of the pharynx and soft palate during chewing/swallowing; 2. using an embodiment of odor preventing device or other device that does not include the deeper remote flange and enables it as well, 3. the use of a different suitable device to achieve the required effect.

2. Wearing the device for providing alternative odor/or for creating relevant alteration in odors' (and flavors) perception for treating and/or prevention of diabetes and/or for alteration of food preferences or for other uses such as addiction rehabilitation or others. For example: to create non-food related attention, to encourage or arouse some other sensation, and/or to create unpleasant odor sensation this can be done for example (non-limiting) by using the device with ingredient of odor and/or by using a material for the device or any relevant part of it that enables transmission of specific odors or particles and blocks others (based on single or on several parameters for example not limited to: molecular weight). Additional use of odor may be done for contributing to a situation similar to smell disorder of the type of smell distortion or phantom. This can be created in several manners, for example (not limited): 1. by simply adding smells, 2. having added smell/odor and also using a device embodiment that allows circulation of odors upcoming from the pharynx/mouth during eating—the combination of the food odors and the odor provided by the device will lead to distorted eating experience and by that will contribute to reduced eating, to weight loss, to fat loss and to alteration of eating habits and food choices (see herein below), 3. using a substance that partially interferes with the perception of smells or creates some deviation of it. Mainly (but not necessarily) towards unpleasant smelling/flavor sensation. It can be done by blocking specific type of sensors at olfactory, using material that is getting attached to odor molecules and changes their perception or in many other manners, 4. using a device embodiment that decrease smelling but not preventing them totally, and then having odor added to the device, in a nature of such odors will create a bias/unpleasant/phantom or will interfere with the regular odors' perception that will lead to several treatments weight loss (as part of diabetes treatment or as a stand-alone treatment), fat mass loss (as part of diabetes treatment or as a stand-alone treatment), alteration of food choices, improvement/reducing/treating/affecting of blood pressure or hypertension, improvement of metabolic and other parameters and any other relevant treatment, etc. 5. Or combine in the device molecules that react with specific smell/other characteristics inputs (for example sweet smell, or specific hormone) and manipulate it to be unpleasant, and may lead to conditioned reaction of un-pleasant/repulsive response to specific smells/foods/inputs etc. This may lead to similar results as of above. And many other methods can be implemented. These methods may be achieved by the creation and/or positioning of a seal, and also as a result of the material that may be used (see above discussion pertaining to seals, sealing members, and materials for seals/sealing members) as well as with other means and variations of the device.

3. Wearing the device to increase bodily energy expenditure and/or increase bodily fat burn and/or affect the sympathetic and/or the para-sympathetic nervous system and or to reduce bodily weight equilibrium point: wearing the device and affecting metabolic cycle of hanger satiation is affecting also the general energy balance and energy expenditure of the body. Affecting the environmental (and part of the internal) bio-chemical sensor of the body (the nose and smelling/sniffing/getting inputs from throat/mouth etc.) is expected to affect the influence of other bodily parameters (for example fat tissues, gastric, heart and others) regarding the energy expenditure as well as regarding bodily fat burn. By enhancing the effect of other bodily signals which signals the brain that a person is satiated and has enough reserves of energy in his/her body, bodily energy expenditure can be increased, and bodily energy reserves can be better utilized, and better be reduced which can then lead to weight loss/fat loss etc. For example (not limiting): change of heart rate, change of oxygen consumption, change in body temperature, sweating, also affecting amount/percentage/composition of the bodily natural disposal/emptying, increase/change thermogenesis, and lipolysis, fat burn, fat deposition and fat management in general, other parameters. Also by doing that the bodily weight of equilibrium/set-point of the body can be changed, and it can be reduced, which can then enable long lasting weight loss and to assist people in avoiding the "yo-yo" situations of losing weight and then gaining it (sometimes with extra-due to higher bodily weight equilibrium/"set point" or due to other reasons), and then lose weight again, gain weight again and so on.

4. To use relevant drug(s) or other ingredient for treating diabetes and administrating it via the nasal by using the device, for example: to treat or manipulate GLP1 receptors or hormone generation, to deliver insulin to deliver Leptin, and any other medical, hormonal, biological, gen or other relevant act or treatment. Each treatment may be aimed to all or to part of the following destinations: olfactory, brain, blood stream, throat or trachea/bronchitis/lower respiratory system/lungs, as well as to any other relevant destination accessible directly or indirectly via the nasal cavity. Each treatment may include one or several elements: for example: insulin and GLP1 analog and each treatment may be directed to one or to several bodily destinations for example in a treatment including Insulin and GLP1 analog part or all maybe directed to the same or to different destinations. For example (not limiting): a treatment which combines odor and insulin may be directing both to the olfactory area and to brain or may be directing the odor to olfactory/brain and the insulin to the bloodstream. In-case of directing both to olfactory/brain—the odor and Insulin treatment may be located on the upper side of the nasal insert body, or at a sealing member that is in proximity to olfaction (on the direction to olfactory area), and also in that case the nasal insert may be positioned at the superior or upper meatuses. On the other hand, in case of directing odor to the olfactory/brain and insulin to the bloodstream: the odor maybe located at the uppermost part of the nasal device/sealing member etc., as close as possible to olfactory area, while the insulin can be located on other parts that come in direct contact with nasal mucus, but are remote or blocked from olfactory. For example, on the nasal device body where it touches the lowest concha or the lateral part at the inferior meatus. In this case the nasal device or part of it containing the insulin may be located in the inferior meatus. Other implementations are of course valid.

4. To manipulate GLP1 receptors or hormone, or other receptors or hormone or other olfactory or brain function or organ, by exposing them by using the device to high concentration of oxygen or to high pressure of oxygen, and by that enhancing them or affecting their function for many treatment including diabetes related treatments, alteration of food choices, reduction of craving to sweet foods and beverages, improvement of blood pressure, improvement of hypertension, improvement of metabolic and other parameters (for example: cognitive, immune system, and others) etc.

In addition, the use of the device enables efficient treatment administration via the nasal cavity, due to the fact that it minimizes the air circulation within the nasal cavity, since air movement is directed to move through the air passageway. This enables a medication/odor or other treatment that are located on the device (or transferred via it) to be absorbed and delivered to the required area without being almost immediately "cleaned" from the nasal cavity by the air flow.

In addition, whenever a treatment should be given to the brain, the most efficient manner to do it may be by using the device for implementation via nasal roof/olfactory area. The transmission of a treatment via this channel bypasses the Brain Blood Barrier (BBB), which is what prevents the majority of treatments done via bloodstream (by injections for example) from reaching the brain.

Provided herein are methods for weight loss/treating overweight individuals/obesity/morbid obesity and alike and for weight management which are in addition to the related methods that are listed above for this and for diabetes related and food choices alteration related.

As indicated, provided herein are methods for preventing weight gain, or methods for enabling weight loss or weight management. Food odors are proven to increase hunger to the cued food and to similar foods, and lead to consumption of foods and to eating larger portions of foods. It seems that people and mammals suffering from obesity have higher sensitivity to food odors resulting in actual hunger and increased food consumption. On the other hand the exposure to flavors, which are generated by the odors of eaten foods and are reaching olfactory during the swallowing process, seems to have different affect over different people: some people when they don't sense these flavors of foods simply eat much less during meals since it is a flat and un-flavored experience (or due to other reason). On the other hand, some people don't get satiated when they don't sense these flavors and therefore they eat more, probably looking for this sensory indication coming through odors during eating and assisting in creating the sensation of satiation (or due to other reason). In order to support this second type of people the method of use of the device for them would be as follows: wearing the device during awaking time (or during other relevant time) in order to block/decrease smelling in general, and taking the product out during meals in order to sense the flavors of the meal and get satiated, and then right after the meal wear the device again until the next meal. Another option would be to use a device that enables the flavors of swallowing but preventing environmental odors (as described above). In this case they may stay with the device also during meals or they can choose to take it out at meals.

Also it is known that a significant part of the hunger and satiation and of the whole metabolic cycle is managed by the brain. As stated above, olfactory has a central role in that by being so tightly connected to it and by serving as the bio-chemical sensor of the brain. Also it provides a channel for drugs administration to brain.

In addition, it had become apparent that prolonged exposure to tastes and flavors during meal promote satiation (long duration of exposure to flavor, rather than exposure to same amount of food during very short time. For example, eating 2 kg of grapes (long exposure) in comparison to drinking a shake made of 2 kg grapes (short exposure). In some research studies, it seems that in general the smelling capabilities are increased once there is hunger and decreased once satiated. On the other hand, in other research studies it has been reported that after eating the ability of smell identification is increased. We believe that this phenomenon is aimed to enable our body to better detect the type of food that is now required; after already eating and satisfying basic needs. In other words, the increased identification capability after eating will enable the detection and consumption of different foods than the ones eaten already in order to support additional needs of the body. Such additional need may be for example, a need for specific minerals, vitamins, fat, sugar or other ingredients that probably were less rich in the meal so far and are required. This together with the fact that the exposure to environmental smells of foods leads in general to a hunger feeling towards that food, thereby increasing the chances of having after meal snacks or desserts that are unnecessary, may be an additional obstacle to weight loss. In order to avoid this, another method can be implemented: after meal the user should use a device containing additional odor (he/she can replace the existing device to a new one with odor, or "dump" it in an odor solution aimed for the purpose etc. or he/she add odor element to it that will be provided, or use other way to have odor—these examples are not meant to be limiting as meant others can be implemented to achieve it). This way it will harden the identification or the sense of environmental odors even more and in addition will keep the smelling sensors occupied by something else by interfering with the natural higher identification/search of different foods that sometimes occur after meal (and of course can be leveraged to other situations).

Also the device can be used for preventing weight gain caused by and/or for supporting weight loss through processes or treatments that may lead or contribute to "weight gaining" or to difficulties in weight loss/weight management. For example (not-limited): smoking quitting, addiction rehabilitation, resolve of nasal/sinusitis congest, using related anti depression medications, taking steroid based treatment, β-blockers based treatments, some of insulin based treatments and many other.

Another method leading to weight loss/to increased satiation is to provide specific hormones such as for example Leptin or other relevant hormones by the device and increasing the leptin level in the brain, or providing medication/any substance inhibiting the generation of Ghrelin or other relevant hormones or providing any other anti-obesity promoting treatment by using the unique capabilities of the nasal insert.

Another method would be, as was elaborated in the sections of preventing and treating diabetes, to create "distorted" smelling and eating experience, and to create change in food choices to support weight loss (for example, but not limited to, food choices towards less sweet, less fatty, less fattening, less calorie's condensed direction, or otherwise healthy foods). Also use of the device can provide methods for improving metabolic parameters such as (but not limited to) insulin related parameters, sugar levels, lipids, decreasing the risk for cardiovascular problems, reducing/preventing high blood pressure, hypertension, reducing fat mass, increasing internal fat burn, increase thermogenesis, promote lipolysis, and, as discussed in detail above, diabetes related problems, etc. Further, methods enabled by the use of the device also include, methods for improving blood pressure, blood parameters, and/or metabolic parameters.

Additional methods of treating/helping overweight individuals/obesity/morbid obesity or for weight management or for prevention of weight gain include, but are not limited to the following: use of the device to manipulate smelling or hormonal mechanism or other mechanism to lead to different food choices that may result in weight loss, in healthier eating habits and in improved metabolic and non-metabolic parameters. For example, less sweet food choices (this may include less sugar, and/or less artificial sweeteners, and/or less cakes and pastries, less sweet beverages etc.), less fatty foods (for example: less fried food, less fat meat, less fat cheese etc.), or choosing foods that have a less carbohydrate content, and less fattening foods, and over all healthier food choices etc. It is important to note that different people react differently to foods. For example a food/diet type that will cause one person to become lean may cause weight gain to a different person. The change in food preferences due to the device may also be a result of enabling higher focus on internal bodily signals rather than external ones or food/eating related ones, as was explained in other sections of this present specification. Also, wearing the device to improve metabolic and non-metabolic parameters, such as, improving insulin, glp1, glucose, lipids, etc. or improved sleeping (if the device is used while sleeping). Improvement of all these metabolic and non-metabolic parameters may all result in weight loss as well as in treating obesity/overweight/morbid obese and alike from additional aspects. This can be achieved by several means and methods, for example (non-limiting): by preventing/decreasing smelling, by specifically manipulating receptors/hormones of specific hormone/s such as GLP1, by providing GLP1 analog based drug, by creating a distorted smelling experience as elaborated above in other sections of this patent application or by enabling the reach of only specific type of practices/any substances to olfactory (for example: not limiting-specific smells, or hormones), by improved sleeping experience etc.

A method for fat loss (for reduction of fat mass): by using the nasal device for decreasing/weakening/inhibiting/blocking/manipulating odors/smells/signals/particles/molecules/etc. to olfactory or by using other nasal device in order to reduce bodily fat mass, and/or in order to reduce fat mass without affecting the heart muscle mass and/or other essential bodily mass and/or fat free mass in general: this is much more specific than weight loss as it specifically relate to the fat mass: one of the main problems with many diets/weight loss processes, is that they lead to reduction of fat free mass (for example: muscle mass) and by that create a negative affect over health.

By "Manipulating" or "manipulation" means changing, and/or managing and/or acting, and/or interfering and/or being involved in and/or influencing, in any manner, to produce a required effect. The manipulation could be of the any substance or of an organ in the nasal cavity or beyond it. For example (non-limiting) by: 1. altering or acting over the any substance, by for example (non-limiting): changing its course of flow, changing something in its components including for example (non-limiting) adding something to it, filtering something etc, changing/affecting the manner it is perceived by the relevant organ (for example non limiting)

adding to the natural flow a component that affect the perception of odors to produce a distorted smelling disorder effect in the brain, etc. 2. Changing, influencing or acting over a part of the nasal cavity or beyond it. For example (non-limiting): blocking type/types of receptors (in any manner) in the olfactory organ, or delivering an odor to it, or preventing a molecule from it etc.

"Any substance" refers to, but is not limited to, odors, smells, signals, triggers, particles, treatments, molecules, air, or anything that may activate or trigger something in the nasal cavity, or beyond it. "Signal(s)" refers to, but is not limited to, electric stimulants, irritants, neuro-chemical stimulants, radiation. In addition, it is clarified that "any substance" may refer to a specific item or generally, to single or to several or to all elements.

Also it is known that in many cases the "yo-yo" phenomenon of losing weight and then re-gaining weight and many time with extra weight (meaning reaching higher weight than of the before the initiation of the weight loss process weight) leads eventually not only to weight gain but also specifically to change in body structure towards more fatty body. Meaning that the fat mass in general and the fat percentage of bodily mass increase relatively to the "before the weight loss" process. Also, in general the loss of muscle mass or other fat free mass may harm metabolism and other functions of the body, and also reduce the calories expenditure of the body. This method consists of using the odors/molecule/signals/etc. prevention/decreasing/inhibiting//manipulating etc. nasal device, or other nasal device to lead specifically to fat loss—meaning reduction fat mass—generally in the body and/or in specific organs of the body, reduction of bodily fat mass and the percentage of the fat in general body mass. Also this method includes such fat reduction process that occur without the loss of muscle and/or other bodily fat free mass. This may be a result of increased bodily fat burn, or by having the nasal device leading to healthier food choices, less fattening foods or by any other mechanism created by the use of the nasal device. The generation of fat loss is not limited specific nasal device as other olfactory manipulating and nasal devices may be efficient for it. Even so that it is now known that decreasing smelling capability may have a general protective effect over body against obesity and related diseases.

Using the device for improved smelling capability would be achieved by having a device that directs air to the olfactory area. Meaning it will increase the reach of air carried odors that are reaching the olfactory and by the will increase the intensity of smells. This can be used for various purposes for example (not limited): for directing drug to olfactory, to direct odors to specific regions to treat the medical and non-medical situations elaborated in this patent application.

Another method would be adding a relevant medication to the odor prevention nasal insert. For example (non-limiting): a smoking cessation medication, for example, but not limited to Chantix; or diabetes relevant hormones, such as, Insulin or GLP1 or other treatments.

Another method would be to add odor(s) to the nasal device. Such odor may have the role of blunting other environmental/internal odors.

Another method would be using a device for improved smelling, by directing air to olfactory.

Also provided herein are methods for preventing and/or treating allergies. More people than ever before suffer from nasal allergies. Research studies indicate that as many as one out of every four people have seasonal and year-round nasal allergies. Experts say nasal allergies are easily the most common chronic respiratory illness. By using the device most (or even all) of the nasal lining can be bypassed and by that there will be a minimal contact between air and nasal lining. The device described for reference herein may be used as is or modified so that it is able to provide full protection to nasal mucosa from contacting the antigens or the problematic substance, or in a manner such that the device is able to direct the air flow and the air stream is most likely to continue fast in the same direction towards the trachea having minimal contact with nasal mucosa and being avoided from the very most of it. Additionally, a filter can be added to the device preventing many allergy causing particles from being inhaled. Additionally, the device can be used for providing treatment both to nasal lining and to the respiratory an immune systems. Also it can be used for providing full blockage or air and particles/molecules/bacteria/signals/other inputs etc. to the nasal cavity by blocking the access to it; as many allergies are originated by the contact of the antigen with the nasal mucosa and by preventing that by occurring the prevention of allergy symptoms may be achieved, or at least contribute to the ease and relief of those allergy symptoms.

Also provided herein is a method of treating/preventing diabetes, addiction rehabilitation, alteration of food preferences, treating overweight/obesity/morbid obesity, treating children and teenagers that are overweight/obesity/morbid obesity, weight management, improvement of blood parameters and metabolic parameters and other bodily parameters, reducing the risk for and/or treatment of cardiovascular issues, blood pressure, hypertension and other metabolic disorder issues, and additionally methods for treating/managing allergies by blocking/reducing/inhibiting molecule(s) and/or substances or signals from reaching and/or activating functions related to the olfactory organ or located near the olfactory region or connected to the olfactory region or on or near or connected to the nasal mucosa. For example, blocking access to receptors located in the olfactory organ or elsewhere in a place that is accessible via the nose (for example, not limiting, in the brain, in the mucosa/in the blood stream, in fat tissues, in liver, in pancreas, in the CNS etc.), and preventing/reducing/inhibiting/otherwise manipulating the excitation (or stated differently the activation of the receptor(s), or the activation of other process such as secretion or synthesis of hormones, transmission of signals and the related results etc.). In one instance, for example, blocking the reach of GLP-1 hormone or analog or agonist, to the GLP-1 receptor in the olfactory and/or in the brain (that is accessible via the nose). Or, in another aspect, blocking the hormone itself, or blocking the transmission of a neural signal, or manipulating any element in the olfactory or that is connected to the olfactory region. This may include blocking the reach of the molecule/hormone via inhalation and/or exhalation, or swallowing, or eating, or any other manner such molecule/hormone may reach the receptors via the nose or may lead to activation/signal transfer etc. Such prevention of activation/excitation for example, may prevent a related effect or may cause other required phenomenon as relevant for the treatment. For example (not-limiting): the blockage of the access of GLP-1 hormone/analog/agonist and alike to the GLP-1 receptor in the olfactory may prevent the transformation of sweet signal to the brain. Such blockage may interfere with the reward response of pleasure to sweet signal. By preventing the activation/excitation of the GLP-1 receptor the sweet-reward circle is reduced and/or is ceased and the wish to consume sweet is diminished. Similarly other effects may be achieved for different purposes. Another non limiting example would be: using the device to prevent/reduce the excitation of insulin receptors in the olfactory area or to manipulate or to encourage the secretion/synthesis of insulin in the brain/CNS/olfactory organ, via intranasal inputs such as inhalation, exhalation, swallowing, eating, etc. This may be leveraged, for example, (non-limiting) for maintaining high insulin level in the brain (as insulin level in the brain tends to be sometimes relatively low after meal and relatively high once fasting—while in the plasma it's the other way around)). Such high insulin level in the brain, may for example aid in different states. Another example would be the prevention of the excitation of Nicotine receptors in or around the olfactory, (and in other embodiments also in the brain). In other aspects, provided herein are methods for blocking/reducing and otherwise manipulating the activation or excitation of receptors associated with various addition related disorders.

The physical and mechanical blockage/prevention of materials/particles/molecules/hormones/odors/air/signals and alike from the olfactory and from (at least part of) the nasal lining that the device is capable of providing, may serve as a non-chemical, non-biological antagonist/blockage/protector/inhibitor for receptors/sensors/nerves/electric/neuron and other elements, and by that manipulate different bodily/brain processes. In other words, in some aspects, the positioning of the device (not comprising a medicament) itself blocks/prevents/manipulate receptors/signals/hormones/odors in or around the olfactory region and beyond it. Such blockage/inhabitation or other manipulations can be enhanced by or combined with adding relevant ingredient to the device (or transformed from external source via it) to be delivered in addition to its natural drug free act, and/or also by combining elements in the device to lead to more precise blockage/transmission, for example (not limiting)—adding micro fibers of metal in order to enable transmission of electric signals but prevent/reduce molecules/air transmission, or use a material that enables transmission of molecular weight but prevent higher molecular weight etc. Also different materials can be used in the device body itself (in addition to the above for achieving the required).

This mechanical/physical and flow related prevention/reduction may also be leveraged for prevention or reduction of the severity of allergies by blocking/reducing the access of antigen molecules to the nasal mucosa, or to other bodily related organs and by that prevent and/or diminish the production of antibodies by the immune system which cause the allergic reaction. In addition other substances can be added to the nasal device to enhance its activity and act. For example, (non-limiting) adding anti-histamines to it, or adding some infection relief or other relief substance, or add some filter or glue to "catch"/prevent/neutralize/manipulate the passing of or reducing the passing of antigen particles.

Additionally provided herein are methods for treating various medical or non-medical issues. The device described herein is for reference and may be modified in various manners in order to fit and achieve the required treatment. The reference device may also be modified to leverage its characteristics, in order to treat various ailments. Furthermore, by wearing the nasal insert in some of the possible embodiments, the air entering the nose from the outside environment or from inside (the mouth/throat/trachea/etc.) is directed through the device, and therefore the air circulation within the nasal cavity is reduced leading to more effective drug/odor delivery achieved by the device. Alternatively, a significant reduction in the intensity of odors/particles/substances etc. reaching the olfactory region of the user can occur. This affects the efficiency and efficacy of the drug/treatment delivery. Therefore, the apparatuses and methods of the present invention enable efficient drug delivery or other treatment, and/or additionally permit manipulation such that the therapeutic agents may reach the relevant target.

Preferably the nasal insert length is as shown but the length, the direction, the location of the insert can vary to direct air towards or away from the olfactory region, or to direct air to other regions in the nasal cavity. Also, the nasal insert may or may not include a set of seals to seal air through the nostril, to direct, to prevent air or any substance from an area etc. In other words, many characteristics of the insert can vary as the nasal insert can be different or modified/adapted in any suitable manner in order to achieve the intended therapeutic effect. Drugs or active ingredients may be provided or included with the insert via a coating, impregnation, connected through external means, etc.

Provided herein are methods of using a nasal insert device according to a specific therapeutic regimen, wherein the therapeutic regimen may include dosage regimen(s) and/or other instructions. Dosage regimens may be adjusted to provide the optimum desired response (e.g., a therapeutic or prophylactic response). For example (non-limiting), the nasal insert may need to be work over a period of 10, 15, 20, 30, 45, 60, 90, or 120 minutes, every 2 through 12 hours daily, or every other day, etc., and may need to be proportionally reduced or increased as indicated by the exigencies of the therapeutic situation. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

The set therapeutic regimen will achieve the intended therapeutic or wellness effect and may need adjustments depending on the ailment or condition or wellness aspect being treated or improved or desired to be achieved and the individual. A "therapeutically effective amount" refers to an amount effective, at dosages and for periods of time necessary, to achieve the desired therapeutic result/wellness/other (therapeutic effect). As described herein the therapeutic effect is achieved by inserting the nasal insert, with or without medicament or odor or any substance, and directing and/or bypassing and/or preventing/reducing/manipulating air/any substance to and/or from specific regions in the nasal cavity or beyond it.

A method of using a nasal insert as described herein for treating of diabetes, prevention of diabetes, reducing the risk for developing diabetes, help living well with diabetes, preventing weight gaining, for weight management, treating allergies, alteration of food choices, addiction rehabilitation, improving blood pressure parameters, preventing or reducing the risk for developing blood pressure related problems, help living well with blood pressure problems, reducing consumption of and/or craving to sweet foods, reducing consumption of and/or craving to sugar, reducing consumption of and/or craving to artificial sweeteners, reducing consumption of and/or craving to sweet beverages, reducing consumption of and/or craving to fattening/unhealthy/sweet/fatty foods, reducing consumption of and/or craving to carbohydrate foods, reducing consumption of and/or craving to baked and pastry based foods, enhancing consumption of and/or craving to healthy foods, altering eating habits towards a healthier diet.

An additional method for using the device of U.S. Pat. No. 8,517,026 (or any other nasal suitable insert) to result in weight loss is as follows: providing a nasal insert, said nasal insert including a body for insertion into a nasal cavity, said nasal insert body defining an air passageway, and having an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body creates a partial or full bypass of the olfactory region or directs the inhaled air and/or other substance to bypass the olfactory region thereby delaying, blocking, or reducing the amount of odors and/or other particles or any substance reaching the olfactory region by inhalation, and wherein said nasal insert body configured to enable the reach of food or other odors or particles or inputs coming from the throat area and/or from inside the body to the olfactory area and wherein the combination prevention/decrease of environmental odors/particles/signals/bacteria/any substance/etc. while enabling the reach of odors/particles/signals/bacteria/etc. of eaten foods/ingredients/other particles coming from the area of the throat and/or from other internal organs, leads to weight loss and/or prevents weight gain, and or to change in food preferences, or to the above mentioned therapeutic effects.

EXAMPLES

Example 1: Alteration of Serum Insulin and Preference for Sweets in Humans by a Device that Inhibits Smell The sense of smell is intimately involved in glucose/insulin metabolism, appetite, satiety, and energy expenditure. Smells can initiate eating (eg popcorn at a movie theater). Changes in smell alters food selection and vice versa. There have been no studies in humans on the effects of intentionally reducing the ability to smell on glucose and insulin metabolism. In this pilot study, the hypothesis that reducing the ability to smell would improve metabolic dysfunction was tested.

The association of diabetes mellitus (DM) with olfaction has been focused on the decrease in olfaction due to diabetes. The etiology of this decrease is not clear, and while the presence of diabetic neuropathy is more often associated with loss of smell, other factors such as severity of diabetes, complications, and/or the time since onset are involved. Insulin and other hormones have complex interactions with olfaction. The olfactory epithelium and bulb have the highest concentrations of insulin and insulin receptors in the CNS. Depending on conditions, intravenous insulin and/or intranasal insulin can increase or decrease olfactory ability and food intake. In humans with decreased smell due to infection, intranasal insulin improved smell. A high fat diet decreases smell and blocks the improvement with intranasal insulin, suggesting that it causes CNS insulin resistance. One potential mechanism of these effects is the voltage-gated potassium channel Kv1.3, which is regulated by insulin, highly expressed in the olfactory bulb, and polymorphisms are related to olfactory ability. Gut hormones including ghrelin, leptin, PYY, and glucagon-like-peptide-1 (GLP1) are produced in the olfactory epithelium and/or bulb or have receptors there, and these affect smell and food intake. Leptin is synthesized in the olfactory epithelium and may inhibit CNS reactivity to food cues. Leptin and orexin infused into the CSF decrease and increase olfaction, respectively. Endocannabinoids promote food intake by increasing odor detection in mice and humans. Of interest for diabetes, GLP1 is specifically involved in sweet taste transmission in rodents and a GLP1 agonist reduced sweet intake in rats. Although most of the studies of GLP1 and other gut hormones were in rodents, humans after gastric bypass surgery have dramatically increased satiety-related gut hormones, a decreased preference for sweet foods, an enhanced sense of smell, and marked improvements in insulin/glucose metabolism.

The relationship of olfaction to insulin dynamics and food selection led us to test a new nasal insert device that reduces smell (Beck Medical, Givat-Ada, Israel) to determine the effects on food intake and glucose and insulin levels.

METHODS: A total of 376 subjects were screened and 156 subjects entered the protocol from two research sites in Israel: Hasharon Hospital, Rabin Medical Center, Petach-Tikva and Emek Medical Center, Afula. The inclusion criteria were a body mass index (BMI) of 30-45 and ages 18-65 years. Subjects in the control group placed two drops of normal saline into their nose daily and device subjects wore it for 5-12 hours during the day. The soft silicone nasal devices were inserted bilaterally and directed air into the posterior nasopharynx, bypassing the olfactory epithelium. Smell tests at baseline and at 12 weeks study end used increasing concentrations of n-butanol to confirm that the device decreased smell. Insulin, glucose, and lipids assays at baseline and study end were analyzed in the hospital laboratory. A dietitian prescribed a 500 kcal reducing diet, saw subjects biweekly for dietary follow up, and administered Aschenbrenner's Questionnaire for Dietary Behaviors and Changes in Food Intake at study end. The study and consent form were approved by Ethics Committees at each site RESULTS: The nasal device was generally well tolerated. There were no serious adverse events and 72% of subjects rated the device comfortable or very comfortable. The control's saline drops had no effect on ability to smell at baseline or after 12 weeks. At 12 weeks 65 completers had smell retested; 28 controls and 37 in the nasal device group. BMI loss was not different: device—2.4±3.3 kg/m$^2$; control—2.1±3.4 kg/m$^2$ (see Table 1 below). Insulin levels did not change significantly in controls (11.03 to 11.43 µU/ml, p-NS), whereas with the nasal device insulin decreased from 12.33 to 10.82 µU/ml, (p<0.02).

There was a significant improvement in HOMA-IR with the nasal device (2.91 to 2.41,p<0.02), but no change in the control group. As compared to the control group, subjects with the nasal device had significantly less preference for sweets: sugar (p=0.015), sweetened beverages (p=0.001), and artificial sweeteners (p=0.02) (see Table 2 below).

DISCUSSION: Despite the well-known associations of olfaction, food intake, and insulin secretion, there are no studies in the literature that have attempted to assess the effects of intentionally reducing the sense of smell on these variables in humans. In this pilot study, the nasal device reduced smell and significantly altered fasting serum insulin and HOMA-IR as compared to the control subjects who lost similar amounts of weight. Also, the device significantly decreased the reported intakes of sugar, sugary beverages, and artificial sweeteners. This suggests that the general preference for sweet taste was diminished.

This proof of concept study did not attempt to identify mechanisms of how the device might produce these favorable effects, and it leaves us with more questions than answers. It can be speculated that the prior data in the literature regarding the association of olfaction with insulin and GLP1 suggests that the nasal device enhances insulin sensitivity directly and/or by altering GLP1 secretion or receptor sensitivity. GLP1 is involved in the transmission of smell in the olfactory mucosa and bulb, and it also enhances insulin sensitivity. After gastric bypass in humans, GLP1 increases dramatically and there is alteration in olfaction and enhanced insulin sensitivity, a pattern similar to what was found in this study. In rats, production of hyposmia by genetic manipulation results in the same pattern. Future studies will evaluate GLP1 and other gut hormones, plus other hormones that have been shown to be associated with olfaction such as leptin and the endocannabinoids. CNS imaging studies also may help identify the pathways through which this device acts.

These findings may have clinical relevance for the treatment of individuals with Type 2 diabetes or prediabetes. The intervention is well tolerated by the large majority of subjects and there were no serious adverse events identified. The fact that serum insulin and HOMA IR improved in the device group but there were no BMI differences from control suggests that the mechanisms of action may be alterations in the CNS. Also, the reduction in preference for sweets may help patients of all types adhere to a diabetes diet more easily. It appears that the device could be added to any current regimen for diabetes.

a meal has been eaten recently. The literature shows a more nuanced picture. Overweight and obese humans and animals tend to have a reduced sense of smell compared to lean individuals. However, obese individuals exposed to pleasant smelling food odors eat more of a test meal than do lean individuals and restrained eaters eat more when exposed to food odors. When mice were fed a high-fat diet their sense of smell decreased and this decrease persisted even when they were returned to a normal chow diet. Obese humans rated the smell of chocolate as more pleasant, had a reduced threshold to smell chocolate, and measures of olfaction were positively associated with body mass index. Both lean and overweight individuals had an increased hunger rating after seeing and smelling pizza for 60 seconds, but overweight individuals had increased salivation and an increased desire to eat both pizza and other tasty foods as compared to lean.

The effects of olfaction on appetite and food intake generally are consistent in adults and children. However, the association of body weight, BMI, and percent body fat with olfaction across the life cycle is less clear. Underweight adults, whether normal or with anorexia, have an enhanced

TABLE 1

Values for completers: baseline, end of study, and change from baseline

| | Nasal Device | | | Control | | | Device | Control | Dev/Con |
|---|---|---|---|---|---|---|---|---|---|
| | Time 0 | Time 8 | p | Time 0 | Time 8 | p | Change | Change | p |
| Weight (kg) | 102.4 ± 13.7 | 95.5 ± 12.4 | 0.001 | 103.0 ± 13.2 | 97.1 ± 12.5 | 0.001 | 6.8 ± 4.4 | 5.9 ± 3.7 | NS |
| BMI (kg/m$^2$) | 36.0 ± 3.4 | 33.6 ± 3.3 | 0.001 | 36.3 ± 3.7 | 34.2 ± 3.4 | 0.001 | 2.4 ± 1.4 | 2.1 ± 1.3 | NS |
| Insulin µU/ml | 12.3 ± 7.6 | 10.8 ± 7.3 | 0.02 | 11.0 ± 4.4 | 11.4 ± 5.4 | NS | −1.5 ± 3.5 | 0.4 ± 5.0 | 0.08 |
| HOMA-IR* | 2.91 ± 1.87 | 2.41 ± 1.66 | 0.01 | 2.74 ± 1.24 | 2.74 ± 1.35 | NS | −0.51 ± .95 | 0 ± 1.35 | NS |

± Standard deviation;
BMI—body mass index;
HOMA-IR—Homeostatic model assessment-insulin resistance
*HOMA IR—Glucose*Insulin/405

TABLE 2

Changes in diet preferences from baseline to end of study

| Type of Food/Beverage | Amount Eaten | Device | Control | p Value |
|---|---|---|---|---|
| Sugar | More | 0% | 0% | 0.015 |
| | Less | 48% | 19% | |
| | Same | 52% | 81% | |
| Artificial sweeteners | More | 18% | 7% | 0.020 |
| | Less | 24% | 4% | |
| | Same | 58% | 89% | |
| Sweetened beverage | More | 0% | 0% | 0.001 |
| | Less | 70% | 26% | |
| | Same | 30% | 74% | |

Example 2: Weight Loss and Alterations in Dietary Preferences Due to Reduction of Smell by a Novel Nasal Device Vary with Age The role of olfaction in regulating appetite, food intake, and body weight has been studied extensively, but is so complex that we have only begun to understand this system. There is a general assumption that the smell of food leads to increased food intake and is a significant factor in causing obesity. For example, upon entering a movie theater the smell of popcorn stimulates a strong desire to eat it even if sense of smell. In adults, as body weight rises, ability to smell decreases. However, this may not be true for children. Obese children had a lower odor detection threshold than lean children. Olfaction sensitivity rises from age 20 to 40 yr and decreases after the age of 50. Specifically, there is a decrease in the ability to smell many food odors in elderly individuals, but ability to smell some types of chemical odors and fruits is better preserved.

There are few data on the effects of reduced smell on food intake and obesity, and almost all studies have been in animals. Drosophila melanogaster (fruit flies) initially increase food intake when exposed to food odors, but with continual exposure, they reduce food intake. Riera knocked out olfactory neurons in mice, resulting in decreased smell. They noted a slight decrease in food intake on chow, but a larger decrease on high fat diet. They found a significant reduction in body weight and fat mass with no change in lean mass and a significant increase in energy expenditure. This was accompanied by a reduced serum insulin, increased insulin sensitivity, and improved glucose tolerance. No studies were found of deliberately reducing smell in humans and assessing body weight or food intake. However, multiple studies show that after obesity surgery smell and taste are altered and there is a correlation of weight loss and alteration of smell and/or taste. Individuals who suffer smell loss after trauma, tumors, or other factors tend to have a reduction in food intake and loss of body weight.

The mechanisms of changes in weight due to olfaction are complex. Olfactory neurons in the nasal cavity connect to the olfactory bulb which is a direct extension of the brain, illustrating the importance of smell during evolution. Multiple hormones and transcription factors are involved in smell, food intake, body weight, and energy expenditure including leptin, insulin, ghrelin, glucagon-like peptide-1 (GLP-1), insulin-like growth factor-1 (IGF1), orexin, neuropeptide Y, endocannabinoids, and cholecystokinin. Of particular interest are receptors for several gut hormones in the nasal olfactory epithelium, olfactory bulb, and in other brain areas that connect to the olfactory system.

Ghrelin, which increases food intake, increased sniffing behavior in both rats and humans. Sniffing increases the amount of odor molecules reaching the olfactory epithelium and increases ability to smell odors. One study compared individuals with anorexia nervosa and with obesity. Anorectics had increased olfactory sensitivity while obese individuals had a decreased sensitivity. They found that ghrelin levels were significantly decreased in obese subjects and were related to smell impairment. Another study demonstrated that compromised phasic ghrelin suppression is associated with increased olfactory perception and decreased satiety response to odors. Leptin, a hormone increased in obesity, is intimately tied with olfaction. One study demonstrated the presence of several isoforms of leptin receptors in the nasal epithelium of rodents and showed that leptin is actually synthesized locally in the olfactory mucosa. Evaluation of lean and obese Zucker rats showed that the obese rats had greater food seeking behavior when exposed to both novel and familiar olfactory cues, but this behavior in rodents returns to normal with leptin injections. Leptin appears to inhibit the brain's reactivity to food cues and may be involved in the production of obesity. Another study infused leptin and orexin into the cerebral spinal space and found that orexin increased, and leptin decreased, olfactory sensitivity. They concluded that orexin and leptin modulate the olfactory performance in a similar way as do physiological induced fasting and satiation and appear to be important factors in the interdependency of olfaction and food intake. The endocannabinoids promote food intake by increasing odor detection in mice and this system is over-active in human obesity. Concentrations of the endocannabinoid, 2-arachidonoylglycerol (2-AG) and endocannabinoid related compounds 2-linoleoylglycerol (2-LG), and 2-oleoylglycerol (2-OG) were increased in obese individuals whereas these and other endocannabinoids were lower in underweight people. They found that smell was increased in the underweight and decreased in the obese individuals. There are numerous insulin receptors in the olfactory bulb and either intravenous or intranasal insulin administration reduces olfaction in normal humans. Paradoxically, in individuals with an impaired sense of smell, intranasal insulin enhances sensitivity, intensity, and discrimination. Riera found that IGF1 receptors in olfactory sensory neurons are critical in olfaction. Loss of IGF1 receptors in olfactory sensory neurons improves olfaction and increases adiposity and insulin resistance. GLP-1 appears critical for smell and taste and GLP-1 receptors are present in the olfactory bulb and olfactory cortex of rats. GLP-1 is associated with weight loss, decreased food intake, altered dietary preferences, and improvements in insulin resistance and glucose tolerance, and is greatly increased after gastric bypass surgery for obesity. Diacetyl, a volatile compound used to enhance flavor and palatability in food, suppresses GLP-1 in enteroendocrine cells and may be associated with increased food intake. Finally, one study reported that bitter and sweet receptors are present in the upper respiratory epithelium and these receptors stimulate (bitter receptors) or inhibit (sweet receptors) secretion of an antimicrobial protein that may be important in glucose metabolism by altering the bacterial flora of the nose.

The purpose of this pilot study was to test the hypotheses that a newly developed nasal insert would reduce the ability to smell, reduce body weight, alter food preferences, and improve metabolic dysfunction.

Methods:

Device: A soft silicone nasal insert similar to that shown in FIGS. 2A and 2B, was obtained for this study (Beck Medical, Givat-Ada, Israel). The device is inserted into the nostrils bilaterally and directs air into the posterior nasopharynx, bypassing the nasal olfactory epithelium, and decreasing the sense of smell. During the trial the device was worn for 5-12 hours during the day and removed at night. Data were collected for time the device was worn by questionnaire at each visit.

Control: To control for the nasal device, an intervention directed to the nose that did not alter olfaction was needed. Subjects in the control group were directed to place two drops of a solution (normal saline) into their nose daily. Efforts were made to try to prevent subjects from the two different groups from talking to each other during office visits. In one case of two subjects (spouses) living in the same household, the randomization process allotted them to two different groups, so both were assigned to the device group.

Subjects and Research Design: This was a randomized, single blinded, placebo-controlled trial. The aims of the study were to assess the capability of the nasal device to reduce smell, to determine the capability of the device to assist in weight loss and improve metabolic function, and to determine if use of the device altered dietary habits and intake of the various nutrients. The subjects were from two research sites in Israel: Hasharon Hospital, Rabin Medical Center, Petach-Tikva and Emek Medical Center, Afula. The inclusion criteria were a body mass index (BMI)≥30, ages 18 to 65 years, and meeting the run in period criteria. Exclusion criteria included medical reasons, pregnancy, anatomical or functional problems of the nose or nasopharynx, participation in a weight reduction program during the last three months, and sensitivity to silicone.

Figure 12:
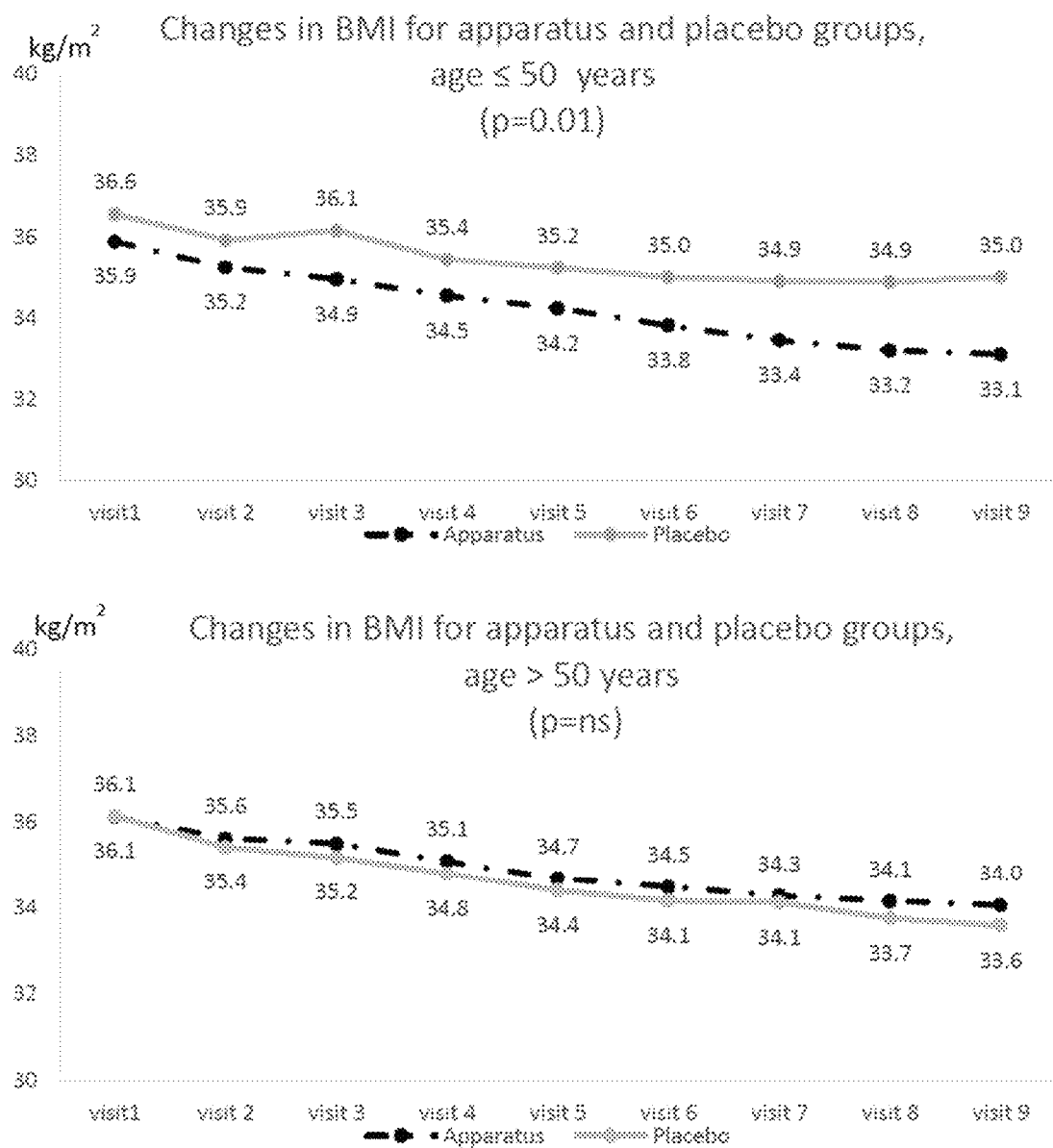
FIG. 12 shows a timeline and study interventions at each time for users using an exemplary nasal insert made in accordance with the present invention.

The timeline and study interventions at each time are shown in FIG. 12.

A total of 65 individuals completed the entire protocol, 37 at the device group and 28 in control group, and had visits with the investigator and the dietitian occurring every two weeks for 12 weeks. At the final visit, the subjects again had blood drawn, a repeat smell test with and without the device and/or control drops, and filled out an eating habits questionnaire.

Dietary intervention protocol: At the initial dietitian visit a diet history was obtained and analyzed by the dietitian. From this history a diet that was relevant for the subject was prescribed, taking into account the subject's likes and dislikes and customary food choices. A balanced diet calculated to produce a reduction of 500 kcal per day from the subject's usual intake was prescribed. The dietitian provided subjects with a "food and usage diary," an ongoing diet record and a record of the use of the device or control saline drops. Subjects were then seen every two weeks by the dietitian who evaluated the food diaries, usage records, and gave encouragement to continue and to comply with the regimen.

Assessment of olfactory ability (smell test): Pure n-butanol was diluted with water into seven dilutions from 4% to 0.0625% for the smell tests and a 3 alternative, forced choice paradigm was used. A study examiner presented three bottles in random order, two bottles containing only water and the third bottle containing a dilution of n-butanol. Each bottle was held 2 cm from the subject's nose for 3 seconds. The lowest concentration of n-butanol was presented first and at each concentration at which the subject could not identify the n-butanol, the next higher concentration was presented until the subject correctly identified that one bottle held the chemical. The test was then repeated an additional three times to ensure that this was the olfactory threshold. If the subject did not identify the smell correctly, the next higher concentration was presented and so on until the subject had recognized correctly the same concentration level for 4 straight trials. After completion of the baseline smell test, subjects waited quietly for 20 minutes, then experimental subjects had the nasal device inserted and control subjects had two drops of saline inserted into each nostril. The smell tests were then repeated.

Laboratory tests: Blood was drawn at baseline and at the final visit. Fasting low density lipoprotein (LDL), high density lipoprotein (HDL), total cholesterol, triglycerides, glucose, and insulin were performed in the Hasharon Hospital laboratory. Insulin resistance was calculated by HOMA (50).

Statistical Analyses: Treatment effects of the nasal device vs control were conducted using three way repeated measures ANOVA. The independent factors in the analysis were group×time×age (2×2×2). The age of participants was included in order to be tested as an intervening factor. Since the research design was within and between comparison (the same participant before vs. after difference) and treatment (study vs. control), the ANOVA used was repeated measure analysis. Two types of effects were the main areas of interest: interaction of group×treatment (time: before/after) and interaction of group×treatment×age (<50; ≥50). In analyses for which significant or nearly significant effects were found, additional t-test comparisons were conducted in order to clarify the source of the differences. In addition, calculations for each measure were followed by 2-way analysis of covariance (ANOVA) of Group×time Age and time 0 as a covariate for time 9, with the aim of validating the differences that were found in previous analysis. The differences for weight variables were tested for percentage of weight reduction relative to time 0 weight, using two-way (group×age) ANOVA. Baseline characteristics between the groups were compared using a Chi square test for categorical variables and t-tests for continuous variables. The alpha level used as a criteria was 0.05. All analyses used SPSS software, version 24 (IBM SPSS Statistics for Windows, Version 24.0. Armonk, N.Y.: IBM Corp. Released 2015).

Results:

Olfaction: In general, subjects tolerated the nasal device well throughout the study. In subjects age 50 or below, 85% rated the device comfortable or very comfortable. In subjects above the age of 50, 65% rated the device comfortable or very comfortable. The nasal device significantly decreased subjects' ability to smell n-butanol at baseline and time 8 ($p<0.001$), whereas there was no difference for the control saline drops. There were no significant differences by age in the scores of the subjects above and below 50 years at either time point.

Body weight: The initial hypothesis regarding body weight was that the nasal device would produce greater weight loss than the control saline drops. For the whole population there were significant differences in body weight and BMI from baseline to end of study for both the nasal device and the control group ($p<0.001$), but there were no statistically significant differences in body weight change between groups (Table 1). Thus, the hypothesis for our primary outcome, weight loss, was not confirmed in the total population (although use of a larger group of participants or longer period trial or additional device models may had changed this result).

Because the literature review had revealed that people above age 50 normally have a decrease in smell, a secondary analysis was conducted by age above or below 50 years, testing for interaction effects of group×age×treatment. As seen in Table 1, in subjects age 50 or below there was a significant difference in weight loss, % weight loss, and BMI in the nasal device group versus control. Weights in the device group dropped by 7.7%±4.2% vs 4.1%±2.9% ($p<0.02$) in the control group (the overall significance level for interaction effect $p<0.01$). BMI of the age≤50 groups device decreased by 2.9±1.8 vs 1.6±1.3 in the controls ($p<0.05$). In subjects above age 50, there were no significant differences between device and control groups.

Dietary Intake: For the total population, subjects in both groups reported an improvement in eating habits from baseline to the end of the 12 wk weight loss protocol as measured by the Aschenbrenner et al questionnaire. As compared to the control group, subjects with the nasal device ate significantly less sugar ($p<0.02$), sweetened beverages ($p<0.001$, and artificial sweeteners ($p<0.02$)(Table 2A). When the groups were separated by age, it was found that the majority of these favorable changes with the nasal device were confined to subjects age 50 or below. In subjects≤50 there were highly significant decreases in intake of sugar, sweetened beverages, and alcoholic beverages (all $p<0.001$), and in artificial sweeteners ($p=0.03$) (Table 2B). There were no significant differences for any of these variables between the nasal device and the control groups in subjects above age 50.

Laboratory Assays: With the nasal device in the total population, there were significant improvements in serum insulin ($p<0.02$) and HOMA-IR ($p<0.01$) over time that were not present in the control group, when device was compared to control.

Blood Pressure: for all ages: only device group showed significant improvement in blood pressure parameters—both systolic and diastolic, while control did not improve significantly any of it: Systolic: Device group reduced from an average of 134 mmHg at the beginning of the study to an average of 126 mmHg at the end p=0.002 (37 participants). Control group reduced from 129.4 mmHg at the beginning of the study to 126.4 mmHg at the end, p=0.34 (25 participants); Diastolic: Device group reduced from an average of 83.7 mmHg at the beginning of the study to an average of 79.9 mmHg at the end p=0.037 (37 participants). Control group reduced from 81.6 mmHg at the beginning of the study to 79.7 mmHg at the end, p=0.314 (25 participants).

For participants age≤50 years from device group reduced significantly both their Systolic and Diastolic blood pressure from beginning to end of the trial, while control group did not. Systolic: age≤50 device: Average blood pressure reduction of 13.3 mmHg in Systolic from 135.6 to 122.3 (p=0.001 beginning to end within device young). The systolic BP reduction with in control young was 4.2 from 126.7 to 122.5 and is p=ns. The difference in reduction in systolic BP between device and control young (p=0.09 ns). Diastolic: age<50 device: reduced an average of 9.5 in the Diastolic, from 87.5 to 78.0 (p=0.002) within young device group from beginning to end. The difference within young control from beginning to end from 82.4 to 80.6 is p=ns. The difference in reduction in Diastolic BP between device and control young is 9.5 vs. 1.77(p=0.03).

Safety: No serious adverse events occurred during the trial.

Discussion:

Despite the well-known association of olfaction, food intake, and obesity, no human studies in the literature that have assessed the effects of deliberately reducing the sense of smell on weight loss in obesity have been identified. Studies in mice show that knocking out the olfactory apparatus causes weight loss, and blocking IGF1 receptors in olfactory sensory neurons improves olfaction but causes adipose tissue gain. Multiple studies have shown that loss of olfaction in humans due to disease or trauma causes weight loss. This pilot study was the first attempt to deliberately reduce smell in humans and to determine the effectiveness of a removable nasal device on body weight and metabolic variables. Our hypothesis was that the nasal device would direct the airstream through the nasopharynx, bypassing a portion of the nasal olfactory apparatus, and this would reduce the sense of smell and produce weight loss and improvement in metabolic variables. Our hypothesis was not confirmed for weight loss in the total population, but when subjects were evaluated by age in a secondary analysis, those age 50 and below had a significant reduction in body weight and BMI with the device. Those benefits were not seen in subjects over age 50. It was hypothesized that the decreased sense of smell reported in the literature after age 50 might affect the ability of the device to reduce body weight. In our assessment of smell using n-butanol, there was no different in subjects above and below the age of 50, but it is postulated that this chemical smell might be perceived differently than food odors. Several studies have shown that there is a decrease in the ability to smell many food odors in elderly individuals, but ability to smell some types of chemical odors and fruits is better preserved. In future studies, food odors will be used to determine if the device reduces smell better in younger vs older individuals.

Also of potential clinical relevance was the alteration in dietary preference for sweets with the nasal device. There were highly significant differences in reported intake of sugar, sweetened beverages, and artificial sweeteners for the whole population and in those ≤50 a highly significant decrease in alcohol intake as well. The effects on the total population were predominantly explained by the highly significant improvements in the younger group. These results in two separate sets of variables give credibility to the hypothesis that younger individuals may respond to the nasal device better than older, and that the reduction in sense of smell in older individuals may be the reason they did not respond with weight loss or dietary improvement.

The differences in serum glucose, insulin, and HOMA-IR between device and control subjects did not reach significance. There were trends suggesting that the device group had improvements in insulin and HOMA-IR and using the data from this trial a power analysis revealed that 50 subjects would be necessary to achieve sufficient power to show a difference in HOMA-IR. Within the ≤50 group, 91% of subjects in the device group had an improvement in HOMA-IR vs 42% in the ≤50 control group. In the >50 group the figures were 63% in the device group and 50% in the control group having an improvement in HOMA-IR over time. These percentages, while provocative, were not significant.

The mechanisms of the improvements in body weight and insulin/glucose dynamics were not studied in this pilot experiment. In future studies, it is planned to focus on mechanisms and to look at hormones known to be present in the nasal epithelium, particularly gut hormones, since multiple such hormones and their receptors have been identified in the olfactory epithelium and olfactory bulb and play a role in ability to smell, food intake, and even energy expenditure. Conversely, levels of gut hormones in the blood and in the nasal olfactory apparatus have been shown to be significant significantly influenced by smell and food odors. It also will be of interest to evaluate alterations in CNS functioning assessed by imaging techniques. Brain imaging has been shown to be significantly influenced by smell and food odors.

This initial pilot study had a number of limitations, including the use of n-butanol rather than food odors to assess olfaction, the limited number of subjects who completed the entire protocol, and the availability of only two nasal device sizes which may have limited the reduction in smell in some subjects. Anecdotal studies with a wider range of device sizes in a small number of individuals suggested that better fitting nasal devices were able to achieve better reductions in smell. Future studies will use a wider range of device sizes.

The differences in weight loss of subjects above and below the age of 50 with the nasal device suggest that future studies should be directed first to younger individuals where greater physiologic changes may be seen and thus it may be easier to determine the mechanisms by which the device produces weight loss and metabolic improvements. Older subjects should be studied, but our initial results suggest the nasal device may have limited usefulness in this age group.

The highly significant reduction in intake of sweets and the trends in improvement in insulin levels and HOMA-IR suggest that future studies in subjects with both overweight/obesity and/or diabetes are indicated. The mechanisms of weight loss in this study were presumed to be due to decreases in food intake or reductions in sweets intake, but this could not be determined with simple food diaries. Future studies may include acute studies to assess food intake, using doubly labeled water to assess energy expenditure, and studies to assess substrate utilization. Also, the known associations of gut hormones with olfaction and the similarities of our findings to changes in body weight and sweet preferences after gastric bypass suggests that evaluation of gut hormones is indicated in future studies.

Values in Table 3 are for all variables are presented for age groups and total population and by change from baseline to Visit 8 (12 weeks) for each variable. Abbreviations: BMI—body mass index, HOMA-IR—homeostasis model assessment: insulin resistance, LDL—low density cholesterol, HDL—high density cholesterol.

In conclusion, a novel nasal device that causes a reduction in the sense of smell holds significant promise to cause weight loss at least in younger subjects, alter dietary preferences that result in a lower intake of sweet foods, and perhaps to improve insulin and glucose metabolism.

TABLE 3

WEIGHT AND LABORATORY VALUES AT BASELINE AND END OF STUDY
FOR TOTAL POPULATION AND IN AGE GROUPS

| | | Nasal Device | | 0-8 p | Control | | 0-8 | 0-8 | 0-8 | Interaction | |
|---|---|---|---|---|---|---|---|---|---|---|---|
| | Age | Time 0 | Time 8 | value t-test | Time 0 | Time 8 | p_value t-test | Device Change | Control Change | Group X treatment | Group X treatment X age |
| Weight (kg) | ≤50 | 106.0 ± 11.3 | 97.7 ± 9.2 | <0.001 | 101.6 ± 13.4 | 97.3 ± 12.4 | <0.001 | −8.3 ± 5.3 | −4.3 ± 3.3 | | .005 |
| | >50 | 99.6 ± 15.0 | 93.9 ± 14.4 | <0.001 | 104.3 ± 13.4 | 96.9 ± 12.9 | 0.001 | −5.7 ± 3.2 | −7.3 ± 3.6 | | |
| | All | 102.4 ± 13.7 | 95.5 ± 12.4 | 0.001 | 103.0 ± 13.2 | 97.1 ± 12.5 | 0.001 | −6.8 ± 4.4 | −5.9 ± 3.7 | NS | |
| BMI (kg/m²) | ≤50 | 35.9 ± 2.7 | 33.1 ± 2.8 | <0.001 | 36.5 ± 4.4 | 35.0 ± 3.8 | <0.001 | −2.8 ± 1.6 | −1.5 ± 1.3 | | .01 |
| | >50 | 36.1 ± 3.8 | 34.0 ± 3.7 | <0.001 | 36.1 ± 3.2 | 33.6 ± 3.0 | <0.001 | −2.1 ± 1.1 | −2.6 ± 1.2 | | |
| | All | 36.0 ± 3.4 | 33.6 ± 3.3 | 0.001 | 36.3 ± 3.7 | 34.2 ± 3.4 | 0.001 | −2.4 ± 1.4 | −2.1 ± 1.3 | NS | |
| Change in % Body Weight | ≤50 | — | — | — | — | — | — | −7.7 ± 4.2 | −4.1 ± 2.9 | | 0.007 *Group X Age |
| | >50 | — | — | — | — | — | — | −5.7 ± 3.1 | −7.0 ± 3.5 | | |
| | All | — | — | — | — | — | — | −6.6 ± 3.7 | −5.7 ± 3.5 | | |
| Insulin (μU/ml) | ≤50 | 14.4 ± 9.8 | 12.7 ± 9.9 | 0.11 | 10.7 ± 4.4 | 12.6 ± 6.6 | ns | −1.7 ± 3.8 | 2.0 ± 6.0 | | NS |
| | >50 | 10.9 ± 5.5 | 9.6 ± 4.7 | 0.08 | 11.3 ± 4.5 | 10.5 ± 4.4 | ns | −1.3 ± 3.3 | −0.9 ± 3.6 | | |
| | All | 12.3 ± 7.6 | 10.8 ± 7.3 | 0.02 | 11.0 ± 4.4 | 11.4 ± 5.4 | NS | −1.5 ± 3.5 | 0.4 ± 5.0 | NS | |
| HOMA-IR* | ≤50 | 3.6 ± 2.4 | 3.1 ± 2.4 | 0.046 | 2.6 ± 1.2 | 2.9 ± 1.6 | NS | −0.57 ± 0.8 | 0.38 ± 1.43 | | NS |
| | >50 | 2.4 ± 1.3 | 2.0 ± 0.8 | 0.096 | 2.9 ± 1.3 | 2.6 ± 1.2 | NS | −0.46 ± 1.04 | −0.33 ± 1.24 | | |
| | All | 2.91 ± 1.87 | 2.41 ± 1.66 | 0.01 | 2.74 ± 1.24 | 2.74 ± 1.35 | NS | −0.51 ± .95 | 0 ± 1.35 | NS | |

TABLE 4

INTAKE OF SELECTED NUTRIENTS
IN DEVICE AND CONTROL GROUPS

A: Intake of selected nutrients in the total population

| Type of Food/Beverage | Amount Eaten | Device | Control | p Value |
|---|---|---|---|---|
| Sugar | More | 0% | 0% | 0.015 |
| | Less | 48% | 19% | |
| | Same | 52% | 81% | |
| Artificial sweeteners | More | 18% | 7% | 0.020 |
| | Less | 24% | 4% | |
| | Same | 58% | 89% | |
| Sweetened beverage | More | 0% | 0% | 0.001 |
| | Less | 70% | 26% | |
| | Same | 30% | 74% | |

B: Intake of selected nutrients by age group

| Type of Food/Beverage | Amount Eaten | Age ≤ 50 | | | Age > 50 | | |
|---|---|---|---|---|---|---|---|
| | | Device | Control | P Value | Device | Control | P Value |
| Sugar | More | 0% | 0% | <0.001 | 0% | 0% | NS |
| | Less | 77% | 8% | | 30% | 29% | |
| | Same | 23% | 92% | | 70% | 71% | |
| Artificial sweeteners | More | 23% | 8% | 0.03 | 15% | 7% | NS |
| | Less | 31% | 0% | | 20% | 7% | |
| | Same | 46% | 92% | | 65% | 86% | |
| Sweetened beverage | More | 0% | 0% | <0.001 | 0% | 0% | NS |
| | Less | 92% | 15% | | 55% | 36% | |
| | Same | 8% | 85% | | 45% | 64% | |
| Alcoholic beverage | More | 0% | 0% | <0.001 | 0% | 0% | NS |
| | Less | 23% | 8% | | 20% | 27% | |
| | Same | 77% | 92% | | 80% | 73% | |

In view of the foregoing the present invention is:

Provided herein is a method for treating and/or preventing diabetes according to a therapeutic regimen, comprising the steps of: providing a nasal insert, said nasal insert including a body for insertion into a nasal cavity, said nasal insert body defining an air passageway, and having an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body is configured to create a bypass of the olfactory region or directs the air and/or other substance to bypass the olfactory region thereby delaying, blocking, or reducing the amount of odors and/or other particles reaching the olfactory region and/or redirecting air to other regions of the nasal cavity or is configured to direct air towards the olfactory region; and wherein the redirecting of the air and the blocking or reducing of odors alters metabolic processes thereby producing a therapeutic effect.

Additionally, provided herein is a method for addiction rehabilitation according to a therapeutic regimen, comprising the steps of: providing a nasal insert, said nasal insert including a body for insertion into a nasal cavity, said nasal insert body comprising an inner surface defining an air passageway, and an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body is configured to create a bypass of the olfactory region or directs the air and/or other substance to bypass the olfactory region thereby delaying, blocking, or reducing the amount of odors and/or other particles reaching the olfactory region and/or redirecting air to other regions of the nasal cavity or is configured to direct air towards the olfactory region; and wherein the redirecting of the air and the blocking or reducing of odors produces a therapeutic effect.

In another aspect, provided herein is a method for alteration of food preferences according to a therapeutic regimen, comprising the steps of: providing a nasal insert, said nasal insert including a body for insertion into a nasal cavity, said nasal insert body comprising an inner surface defining an air passageway, and an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body is configured to create a bypass of the olfactory region or directs the air and/or other substance to bypass the olfactory region thereby delaying, blocking, or reducing the amount of odors and/or other particles reaching the olfactory region and/or redirecting air to other regions of the nasal cavity or is configured to direct air towards the olfactory region; and wherein the redirecting of the air and the blocking or reducing of odors alters metabolic processes thereby promoting healthier food choices and producing a therapeutic effect.

Also provided herein is a method for treating overweight/obesity/morbid obesity according to a therapeutic regimen, comprising the steps of: providing a nasal insert, said nasal insert including a body for insertion into a nasal cavity, said nasal insert body comprising an inner surface defining an air passageway, and an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body is configured to create a bypass of the olfactory region or directs the air and/or other substance to bypass the olfactory region thereby delaying, blocking, or reducing the amount of odors and/or other particles reaching the olfactory region and/or redirecting air to other regions of the nasal cavity or is configured to direct air towards the olfactory region; and wherein the redirecting of the air and the blocking or reducing of odors alters metabolic processes thereby reducing the urge to eat and producing a therapeutic effect.

Also provided is a method for preventing or treating allergies, comprising the steps of: providing a nasal insert, said nasal insert including a body for insertion into a nasal cavity, said nasal insert body comprising an inner surface defining an air passageway, and an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body is configured to create a bypass of the olfactory region or directs the air and/or other substance to bypass the olfactory region thereby delaying, blocking, or reducing the amount of odors and/or other particles reaching the olfactory region and/or redirecting air to other regions of the nasal cavity or is configured to direct air towards the olfactory region; and wherein the nasal insert body prevents particles causing allergic reaction from reaching unwanted areas in the nasal cavity.

Further provided herein is a method for treating and/or preventing over-weight/obesity/morbid obesity according to a therapeutic regimen, comprising the steps of: providing a nasal insert, said nasal insert including a body for insertion into a nasal cavity, said nasal insert body defining an air passageway, and having an outer surface, said outer surface configured to form a seal between said nasal insert body and the nasal cavity; inserting said nasal insert body into the nasal cavity such that the nasal insert body rests against a portion of the nasal cavity wherein the nasal insert body is configured to create a bypass of the olfactory region or directs the air and/or other substance to bypass the olfactory region thereby delaying, blocking, or reducing the amount of odors and/or other particles reaching the olfactory region and/or redirecting air to other regions of the nasal cavity or is configured to direct air towards the olfactory region; and wherein the redirecting of the air and/or other substances alters food choices, and/or reduces eating, and/or increases bodily energy expenditure, and/or enhances or changes an effect on bodily metabolic pathways, and/or directs specific odors/particles to olfactory/brain, and/or enhances an effect of specific particles or odors over the olfactory and brain, and/or alters metabolic processes thereby producing a therapeutic effect.

Also provided herein is a method for preventing weight gain or for supporting weight loss according to a therapeutic regimen, comprising the steps of: providing a nasal insert, said nasal insert including a body for insertion into a nasal cavity, said nasal insert body comprising an inner surface defining an air passageway, and an outer surface, said outer surface configured to form a seal between said nasal insert body and the nasal cavity; inserting said nasal insert body into the nasal cavity such that the nasal insert body rests against a portion of the nasal cavity wherein the nasal insert body is configured to create a bypass of the olfactory region or directs the air and/or other substance to bypass the olfactory region thereby delaying, blocking, or reducing the amount of odors and/or other particles reaching the olfactory region and/or redirecting air to other regions of the nasal cavity or is configured to direct air towards the olfactory region; and wherein the redirecting of the air and the blocking or reducing of odors alters metabolic processes thereby reducing the urge to eat and producing a therapeutic effect.

Also provided is a method for addiction rehabilitation comprising the steps of: providing a nasal insert, said nasal insert including a nasal insert body for insertion into a nasal cavity, said nasal insert body comprising an inner surface or material, and an outer surface or material, said nasal insert body being adapted to fit inside a nasal cavity; inserting said nasal insert body into the nasal cavity such that the nasal insert body rests against a portion of the nasal cavity, creating a partial or full blockage of the nasal cavity; and wearing the nasal insert body for an amount of time, wherein the wearing of the nasal insert body creates a feeling of a mild cold and/or light runny nose, and/or a feeling of sickness or a feeling of disgust and/or less enjoyable or less comfortable experience while attempting to consume an addictive substance, resulting in a reduction or elimination of a user's craving to consume the addictive substance and/or in reduction or elimination of the amount of consumption of the addictive substance.

Also provided herein is a method for treating diabetes, for alteration of food preferences, for treating allergies, for treating overweight/obesity/morbid obesity according to a therapeutic regimen, comprising the steps of: providing a nasal insert, said nasal insert including a nasal insert body for insertion into a nasal cavity, said nasal insert body comprising an inner surface or material, and an outer surface or material, said nasal insert body being adapted to fit inside a nasal cavity; inserting said nasal insert body into the nasal cavity such that the nasal insert body rests against a portion of the nasal cavity, creating a partial or full blockage of the nasal cavity; and wearing the nasal insert body for an amount of time wherein wearing of the nasal insert body creates a feeling of a mild cold and/or light runny nose, and/or a feeling of sickness or a feeling of disgust and/or less enjoyable or less comfortable experience resulting in a the relevant improvement.

Provided herein is a method of using a nasal insert as described herein for treating of diabetes, prevention of diabetes, preventing weight gaining, treating allergies, alteration of food choices, addiction rehabilitation, reducing consumption of and/or craving to sweet foods, reducing consumption of and/or craving to sugar, reducing consumption of and/or craving to artificial sweeteners, reducing consumption of and/or craving to sweet beverages, reducing consumption of and/or craving to fatty foods, reducing consumption of and/or craving to carbohydrate foods, reducing consumption of and/or craving to backed and pastry based foods, enhancing consumption of and/or craving to healthy foods, altering eating habits towards a healthier diet.

Also provided is a method for treating weight loss, comprising: providing a nasal insert, said nasal insert including a body for insertion into a nasal cavity, said nasal insert body defining an air passageway, and having an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body creates a partial or full bypass of the olfactory region or directs the inhaled air and/or other substance to bypass the olfactory region thereby delaying, blocking, or reducing the amount of odors and/or other particles reaching the olfactory region by inhalation, and wherein said nasal insert body configured to enable the reach of food or other odors or particles coming from the throat area and/or from inside the body to the olfactory area and wherein the combination prevention/decrease of environmental odors/particles/signals while enabling the reach of odors/particles/signals of eaten foods/ingredients/other particles coming from the area of the throat and/or from other internal organs leads to weight loss and/or prevents weight gain.

Additionally, provided herein is a method for treating and/or preventing diabetes, comprising the steps of: providing a nasal insert, said nasal insert including a body for insertion into a nasal cavity, said nasal insert body defining an air passageway, and having an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body is configured to create a bypass of the olfactory region or directs the air and/or odors, and/or other substance/particles/signals/elements/etc. to bypass the olfactory region thereby delaying, blocking, manipulating or reducing the amount of air and/or odors, and/or other substance/particles/signals/elements/etc. from reaching to, or in relation of the olfactory region and/or redirecting air and/or odors, and/or other substance/particles/signals/elements/etc. to other regions of the nasal cavity or beyond it, or is configured to direct air and/or odors, and/or other substance/particles/signals/elements/etc. towards the olfactory region; and wherein the redirecting of air and/or odors, and/or other substance/particles/signals/elements/etc. and/or the blocking or reducing or manipulation of air and/or odors, and/or other substance/particles/signals/elements/etc. alters metabolic processes thereby producing a therapeutic effect.

Also provided herein is a method for addiction rehabilitation, comprising the steps of: providing a nasal insert, said nasal insert including a body for insertion into a nasal cavity, said nasal insert body comprising an inner surface defining an air passageway, and an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body is configured to create a bypass of the olfactory region or directs the air and/or odor(s), and/or other substance(s)/particle(s)/signal(s)/element(s)/etc. to bypass the olfactory region thereby delaying, blocking, manipulating, or reducing the amount air and/or odor(s), and/or other substance(s)/particle(s)/signal(s)/element(s)/etc. from reaching to or in relation of the olfactory region and/or redirecting air and/or odor(s), and/or other substance(s)/particle(s)/signal(s)/element(s)/etc. to other regions of the nasal cavity or is configured to direct air and/or odor(s), and/or other substance(s)/particle(s)/signal(s)/element(s)/etc. towards the olfactory region; and wherein the redirecting of air and/or odor(s), and/or other substance(s)/particle(s)/signal(s)/element(s)/etc. and/or the blocking or reducing or manipulation of air and/or odor(s), and/or other substance(s)/particle(s)/signal(s)/element(s)/etc. produces a therapeutic effect.

Also provided herein is a method for alteration of food preferences according to a therapeutic regimen, comprising the steps of: providing a nasal insert, said nasal insert including a body for insertion into a nasal cavity, said nasal insert body comprising an inner surface defining an air passageway, and an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body is configured to create a bypass of the olfactory region or directs the air, and/or odor(s), and/or other substance/particle(s)/signal(s)/element(s)/etc. to bypass the olfactory region thereby delaying, blocking, manipulating, or reducing the amount of air and/or odor(s), and/or other substance(s)/particle(s)/signal(s)/element(s)/etc. reaching to or in relation of the olfactory region and/or redirecting air and/or odor(s), and/or other substance(s)/particle(s)/signal(s)/element(s)/etc. to other regions of the nasal cavity or is configured to direct air and/or odor(s), and/or other substance(s)/particle(s)/signal(s)/element(s)/etc. towards the olfactory region; and wherein the redirecting of air and/or odor(s), and/or other substance(s)/particle(s)/signal(s)/element(s)/etc. and/or the blocking or reducing or manipulation of air and/or odor(s), and/or other substance(s)/particle(s)/signal(s)/element(s)/etc. alters metabolic processes thereby promoting healthier food choices and producing a therapeutic effect.

Further provided herein is a method for treating over-weight/obesity/morbid obesity according to a therapeutic regimen, comprising the steps of: providing a nasal insert, said nasal insert including a body for insertion into a nasal cavity, said nasal insert body comprising an inner surface defining an air passageway, and an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body is configured to create a bypass of the olfactory region or directs the air and/or odor(s), and/or other substance(s)/particle(s)/signal(s)/element(s)/etc. to bypass the olfactory region thereby delaying, blocking, or reducing the amount of odors and/or other particles reaching the olfactory region and/or redirecting air to other regions of the nasal cavity or is configured to direct air towards the olfactory region; and wherein the redirecting of air and/or odor(s), and/or other substance(s)/particle(s)/signal(s)/element(s)/etc. and/or the blocking or reducing or manipulation of air and/or odor(s), and/or other substance(s)/particle(s)/signal(s)/element(s)/etc. alters metabolic processes thereby reducing the urge to eat and producing a therapeutic effect.

Also provided herein is a method for preventing or treating allergies, comprising the steps of: providing a nasal insert, said nasal insert including a body for insertion into a nasal cavity, said nasal insert body comprising an inner surface defining an air passageway, and an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body is delaying, blocking, or reducing the amount of odors and/or antigen(s), and/or other particles/substances/signals etc. being in contact with nasal mucosa, and/or redirecting air to other regions of the nasal cavity or beyond the nasal cavity; and wherein the nasal insert body prevents particles causing allergic reaction from reaching unwanted areas in the nasal cavity.

Additionally provided herein is a method for treating and/or preventing over-weight/obesity/morbid obesity according to a therapeutic regimen, comprising the steps of: providing a nasal insert, said nasal insert including a body for insertion into a nasal cavity, said nasal insert body defining an air passageway, and having an outer surface, said outer surface configured to form a seal between said nasal insert body and the nasal cavity; inserting said nasal insert body into the nasal cavity such that the nasal insert body rests against a portion of the nasal cavity wherein the nasal insert body is configured to create a bypass of the olfactory region or directs the air and/or other substance to bypass the olfactory region thereby delaying, blocking, or reducing the amount of odors and/or other particles reaching the olfactory region and/or redirecting air to other regions of the nasal cavity or is configured to direct air towards the olfactory region; and wherein the redirecting of the air and/or other substances alters food choices, and/or reduces eating, and/or increases bodily energy expenditure, and/or enhances or changes an effect on bodily metabolic pathways, and/or directs specific odors/particles to olfactory/brain, and/or enhances an effect of specific particles or odors over the olfactory and brain, and/or alters metabolic processes thereby producing a therapeutic effect.

Further provided herein is a method for preventing weight gain or for supporting weight management and/or weight loss according to a therapeutic regimen, comprising the steps of: providing a nasal insert, said nasal insert including a body for insertion into a nasal cavity, said nasal insert body comprising an inner surface defining an air passageway, and an outer surface, said outer surface configured to form a seal between said nasal insert body and the nasal cavity; inserting said nasal insert body into the nasal cavity such that the nasal insert body rests against a portion of the nasal cavity wherein the nasal insert body is configured to create a bypass of the olfactory region or directs the air and/or other substance to bypass the olfactory region thereby delaying, blocking, or reducing the amount of odors and/or other particles reaching the olfactory region and/or redirecting air to other regions of the nasal cavity or is configured to direct air towards the olfactory region; and wherein the redirecting of the air and the blocking or reducing of odors alters metabolic processes thereby reducing the urge to eat and producing a therapeutic effect.

Additionally provided herein is a method for addiction rehabilitation comprising the steps of: providing a nasal insert, said nasal insert including a nasal insert body for insertion into a nasal cavity, said nasal insert body comprising an inner surface or material, and an outer surface or material, said nasal insert body being adapted to fit inside a nasal cavity; inserting said nasal insert body into the nasal cavity such that the nasal insert body rests against a portion of the nasal cavity, creating a partial or full blockage of the nasal cavity; and wearing the nasal insert body for an amount of time, wherein the wearing of the nasal insert body creates a feeling of a mild cold and/or light runny nose, and/or a feeling of sickness or a feeling of disgust and/or less enjoyable or less comfortable experience while attempting to consume an addictive substance, resulting in a reduction or elimination of a user's craving to consume the addictive substance and/or in reduction or elimination of the amount of consumption of the addictive substance.

Also provided is a method for treating diabetes, for alteration of food preferences, for treating allergies, for treating overweight/obesity/morbid obesity for weight management according to a therapeutic regimen, comprising the steps of: providing a nasal insert, said nasal insert including a nasal insert body for insertion into a nasal cavity, said nasal insert body comprising an inner surface or material, and an outer surface or material, said nasal insert body being adapted to fit inside a nasal cavity; inserting said nasal insert body into the nasal cavity such that the nasal insert body rests against a portion of the nasal cavity, creating a partial or full blockage of the nasal cavity; and wearing the nasal insert body for an amount of time wherein wearing of the nasal insert body creates a feeling of a mild cold and/or light runny nose, and/or a feeling of sickness or a feeling of disgust and/or less enjoyable or less comfortable experience resulting in a the relevant improvement.

Further provided is a method of using a nasal insert as described herein for treating of diabetes, prevention of diabetes, preventing weight gaining, treating allergies, alteration of food choices, addiction rehabilitation, reducing consumption of and/or craving to sweet foods, reducing consumption of and/or craving to sugar, reducing consumption of and/or craving to artificial sweeteners, reducing consumption of and/or craving to sweet beverages, reducing consumption of and/or craving to fatty foods, reducing consumption of and/or craving to carbohydrate foods, reducing consumption of and/or craving to backed and pastry based foods, enhancing consumption of and/or craving to healthy foods, altering eating habits towards a healthier diet.

Additionally provided herein is a method for treating weight loss, comprising: providing a nasal insert, said nasal insert including a body for insertion into a nasal cavity, said nasal insert body defining an air passageway, and having an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body creates a partial or full bypass of the olfactory region or directs the inhaled air and/or other substance to bypass the olfactory region thereby delaying, blocking, or reducing the amount of odors and/or other particles reaching the olfactory region by inhalation, and wherein said nasal insert body configured to enable the reach of food or other odors or particles coming from the throat area and/or from inside the body to the olfactory area and wherein the combination prevention/decrease of environmental odors/particles/signals while enabling the reach of odors/particles/signals of eaten foods/ingredients/other particles coming from the area of the throat and/or from other internal organs leads to weight loss and/or prevents weight gain.

Using any of the above mentioned methods, wherein insertion of the nasal insert into the nasal cavity blocks, prevents, reduces, or delays smelling.

Using any of the above mentioned methods, wherein insertion of the nasal insert into the nasal cavity distorts smelling and/or leads to unpleasant flavors and smells.

Using any of the above mentioned methods, wherein the nasal insert contains or comprises a medicine and/or a hormone and/or oxygen.

Using any of the above mentioned methods, wherein the nasal insert contains or comprises an odor and/or a substance affecting the perception of odor(s) and/or flavors.

Using any of the above mentioned methods, wherein insertion of the nasal insert into the nasal cavity changes the perception of existing environmental smells, thereby interfering with flavors and smells, alteration of food choices, and/or improvement of metabolic parameters leading to weight loss.

Using any of the above mentioned methods, wherein the nasal insert is configured to create a pass and/or to block/prevent/reduce access to the olfactory region and/or to other region and directing air and/or other substances towards the olfactory and/or to another region.

Using any of the above mentioned methods, wherein the nasal insert is configured to be positioned in any of the nasal meatuses.

Using any of the above mentioned methods, wherein use of the nasal insert gives a user a sensation of satiation.

Using any of the above mentioned methods, wherein the nasal insert is worn during meal time.

Using any of the above mentioned methods, wherein the nasal insert is worn during sleeping hours.

Using any of the above mentioned methods, wherein the nasal insert is worn during the day.

Using any of the above mentioned methods, wherein the nasal insert is not worn during meal time.

Using any of the above mentioned methods, wherein the nasal insert is worn for providing a therapeutic substance to a target destination.

Using any of the above mentioned methods, wherein the therapeutic effect includes alteration of food choices.

Using any of the above mentioned methods, wherein the therapeutic effect include reduced consumption of and/or reduction of the craving for: sweet foods, and/or carbohydrate foods, fat foods, sugar, and/or artificial sweeteners, and or sweet foods and beverages, and/or fatty foods, and/or, alcohol.

Using any of the above mentioned methods, wherein the method further includes manipulation of smells that leads to mimicking a situation similar to smell distortion.

Using any of the above mentioned methods, wherein the method is modified to treat, instead of or in addition to weight loss, one or more of the following: treating or preventing diabetes, alteration of food choices, treating or preventing allergies, addiction rehabilitation, affecting metabolic related processes, improving metabolic parameters, addiction rehabilitation, smelling prevention, smelling decreasing, decreasing or preventing the effect of environmental bio-chemical signals through the nose while enabling and/or enhancing the reach of internal bodily/foods/particles signals reach through the nose and/or through other channels.

Using any of the above mentioned methods, wherein the method comprises blocking or preventing or reducing or inhibiting or manipulating a molecule, and/or a hormone, and/or a signal and/or any other substance from reaching and/or activating functions related to the olfactory organ or located near the olfactory region or connected to the olfactory region or to other bodily organs which are connected to olfactory.

Using any of the above mentioned methods, wherein the method is modified to treat, instead of or in addition to weight loss, one or more of the following: treating or preventing diabetes, alteration of food choices, treating or preventing allergies, addiction rehabilitation, affecting metabolic related processes, improving metabolic parameters, addiction rehabilitation, smelling prevention, smelling decreasing, decreasing or preventing the effect of environmental and internal bio-chemical and other signals through the nose while enabling and/or enhancing the effect of other internal bodily inputs.

Using any of the above mentioned methods, wherein the nasal insert in use does not comprise a sealing member and does not create a seal.

Using any of the above mentioned methods, wherein the nasal insert in use does not direct/redirect.

Using any of the above mentioned methods, wherein the nasal insert is configured to create a pass and/or to block/prevent/reduce access to the olfactory region and/or to other region and directing air and/or other substances towards the olfactory and/or to another region.

Using any of the above mentioned methods, wherein the therapeutic effect is one or more of the following: a. reducing fat mass, b. reducing fat mass without reducing muscle mass, c. reducing fat mass without reducing fat free mass, d. increasing bodily fat burn, e. increasing bodily energy expenditure, f. reducing insulin resistance, g. reducing blood lipids, h. improving glucose parameters, and i. altering food choices towards healthier diet.

Further, provided herein is a method for treating or preventing diabetes, comprising the steps of: providing a nasal insert, said nasal insert including a body for insertion into a nasal cavity, said nasal insert body defining an air passageway, and having an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body is configured to either (1) create a bypass of the olfactory region or direct any substance away from the olfactory region thereby delaying, blocking, manipulating or reducing the amount of the any substance from reaching the olfactory, or being in close proximity to the olfactory region, and/or redirecting the any substance to other regions of the nasal cavity or beyond, or (2) wherein the nasal insert is configured to direct the any substance towards the olfactory region; and wherein the redirection of the any substance, and/or the blocking or reducing or manipulation of the any substance alters metabolic processes thereby producing a therapeutic effect.

Additionally provided is a method for treating an overweight, obese, or morbidly obese individual according to a therapeutic regimen, comprising the steps of: providing a nasal insert, said nasal insert including a body for insertion into a nasal cavity, said nasal insert body comprising an inner surface defining an air passageway, and an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body is configured to either (1) create a bypass of the olfactory region or direct any substance away from the olfactory region thereby delaying, blocking, manipulating, or reducing the amount of the any substance from reaching the olfactory region, or being in close proximity to the olfactory region, and/or redirecting the any substance to other regions of the nasal cavity or beyond it, or (2) wherein the nasal insert is configured to direct the any substance towards the olfactory region; and wherein the redirection of the any substance, and/or the blocking or reducing or manipulation of the any substance alters metabolic processes thereby reducing the urge to eat and producing a therapeutic effect.

Using any of the above mentioned methods, wherein insertion of the nasal insert into the nasal cavity blocks, prevents, reduces, or delays smelling.

Using any of the above mentioned methods, wherein insertion of the nasal insert into the nasal cavity distorts smelling and/or leads to unpleasant flavors and smells, or wherein the nasal insert contains or comprises an odor and/or a substance affecting the perception of odor(s) and/or flavors.

Using any of the above mentioned methods, wherein the nasal insert contains or comprises a medicine and/or a hormone and/or oxygen.

Using any of the above mentioned methods, wherein the nasal insert is configured to be positioned in any of the nasal meatuses.

Using any of the above mentioned methods, wherein use of the nasal insert gives a user a sensation of satiation.

Using any of the above mentioned methods, wherein the nasal insert is worn during meal time.

Using any of the above mentioned methods, wherein the nasal insert is worn for providing a therapeutic substance, and wherein the nasal insert is positioned in a user such that the therapeutic substance reaches a target destination, thereby providing the therapeutic effect.

Using any of the above mentioned methods, wherein the wearing of the nasal insert body creates a feeling of a mild cold and/or light runny nose, and/or a feeling of sickness or a feeling of disgust and/or less enjoyable or less comfortable experience resulting in the therapeutic effect.

Using any of the above mentioned methods, wherein the therapeutic effect includes alteration of food choices.

Additionally provided herein is a method for treating or preventing diabetes; or overweight, obese, or morbidly obese individuals; or treatment of addiction, or alteration of food choices; or treating allergies, comprising the steps of: providing a nasal insert, said nasal insert including a body for insertion into a nasal cavity, said nasal insert body defining an air passageway, and having an outer surface, said outer surface configured to form a seal between said nasal insert body and the nasal cavity; inserting said nasal insert body into the nasal cavity such that the nasal insert body rests against a portion of the nasal cavity creating a sealing between said nasal insert body and the nasal cavity; wherein the nasal insert body is configured to either (1) create a bypass of the olfactory region or direct any substance away from the olfactory region thereby delaying, blocking, manipulating or reducing the amount of the any substance from reaching the olfactory, or being in close proximity to the olfactory region, and/or redirecting the any substance to other regions of the nasal cavity or beyond, or (2) wherein the nasal insert is configured to direct the any substance towards the olfactory region; and wherein the redirection of the any substance, and/or the blocking or reducing or manipulation of the any substance alters metabolic processes thereby producing a therapeutic effect.

Using any of the above methods, wherein the method treats allergies and the redirection prevents particles causing the allergies from reaching unwanted areas of the nasal cavity.

Using any of the above methods, wherein said outer surface is configured to form an outer surface to form a seal with the nasal cavity when the nasal insert is inserted into the nasal cavity.

It will be readily appreciated by those skilled in the art that modifications may be made to the invention without departing from the concepts disclosed in the foregoing description. Accordingly, the particular embodiments described in detail herein are illustrative only and are not limiting to the scope of the invention, which is to be given the full breadth of the appended claims and any and all equivalents thereof.

The claimed invention is:

1. A method for treating or preventing diabetes, comprising the steps of:
   providing a nasal insert, said nasal insert including a body for insertion into a nasal cavity, said nasal insert body defining an air passageway, and having an outer surface; and
   inserting said nasal insert body into the nasal cavity of an individual diagnosed with or predisposed to diabetes;
   wherein the nasal insert body is configured to either (1) create a bypass of an olfactory region of the nasal cavity or direct any substance away from the olfactory region thereby delaying, blocking, or reducing an amount of or manipulating the any substance from reaching the olfactory region, or being in close proximity to the olfactory region, and/or to one or more other regions of the nasal cavity or beyond, and/or (2) wherein the nasal insert is configured to direct the any substance towards the olfactory region, and/or towards the one or more other regions of the nasal cavity or beyond and/or to manipulate the any substance in relation to the olfactory region and/or the one or more other regions of the nasal cavity or beyond, and/or (3) wherein the nasal insert is configured to manipulate the olfactory region and/or the one or more other regions of the nasal cavity or beyond;

and wherein the direction of the any substance towards or away from the olfactory region, and/or towards or away form the one or more other regions of the nasal cavity and/or beyond, and/or the blocking or reducing or manipulation of the any substance and/or the olfactory region and/or the one or more other regions of the nasal cavity and/or beyond, alters metabolic processes thereby producing a therapeutic effect.

2. The method of claim 1, wherein insertion of the nasal insert body into the nasal cavity blocks, prevents, reduces, or delays smelling.

3. The method of claim 1, wherein inserting the nasal insert body into the nasal cavity distorts smelling and/or leads to unpleasant and/or different flavors and/or smells, or wherein the nasal insert body contains, comprises, or is capable of transferring to the nasal cavity a substance that affects the individual's perception of odor(s) and/or flavors.

4. The method of claim 1, wherein the nasal insert body is configured to be positioned in one or more nasal meatuses and/or other areas of the nasal cavity and/or is configured to give the individual a sensation of satiation.

5. The method of claim 1, wherein the nasal insert is used for a duration, situation, and/or frequency sufficient to produce the therapeutic effect.

6. The method of claim 1, wherein the nasal insert is worn for providing a therapeutic substance, and wherein the nasal insert is positioned in the nasal cavity of the individual such that the therapeutic substance reaches a target destination, thereby providing the therapeutic effect.

7. The method of claim 1, wherein the nasal insert is worn to create a feeling of a mild cold and/or light runny nose, and/or a feeling of sickness or a feeling of disgust and/or less enjoyable or less comfortable experience resulting in the therapeutic effect.

8. The method of claim 1, wherein said outer surface is configured to form a seal with the nasal cavity.

9. The method of claim 1, further comprising, prior to inserting the nasal insert body into the nasal cavity of the individual, applying a solution to the nasal insert body to cause the nasal insert body to have an odor of a food.

10. The method of claim 1, further comprising providing a diabetes relevant hormone to the individual while the nasal insert body is inserted in the nasal cavity of the individual.

11. The method of claim 10, wherein the nasal insert body comprises the diabetes relevant hormone and/or wherein the diabetes relevant hormone is contained in the nasal insert body, and
wherein the diabetes relevant hormone is absorbed by the individual in the nasal cavity.

12. A method for treating an overweight, obese, or morbidly obese individual or individuals that need to lose weight according to a therapeutic regimen, comprising the steps of:
providing a nasal insert, said nasal insert including a body for insertion into a nasal cavity, said nasal insert body comprising an inner surface defining an air passageway, and an outer surface; and
inserting said nasal insert body into the nasal cavity of the overweight, obese, or morbidly obese individual or to the individuals that need to lose weight;
wherein the nasal insert body is configured to either (1) create a bypass of an olfactory region of the nasal cavity or direct any substance away from the olfactory region thereby delaying, blocking, or reducing an amount of or manipulating the any substance from reaching the olfactory region, or being in close proximity to the olfactory region, and/or to one or more other regions of the nasal cavity or beyond, and/or (2) wherein the nasal insert is configured to direct the any substance towards the olfactory region, and/or towards the one or more other regions of the nasal cavity or beyond and/or to manipulate the any substance in relation to the olfactory region and/or the one or more other regions of the nasal cavity or beyond, and/or (3) wherein the nasal insert is configured to manipulate the olfactory region, and/or the one or more other regions of the nasal cavity or beyond;

and wherein the direction of the any substance towards or away form the olfactory region, and/or towards or away from the one or more other regions of the nasal cavity and/or beyond, and/or the blocking or reducing or manipulation of the any substance and/or the olfactory region and/or the one or more other regions of the nasal cavity and/or beyond, alters metabolic processes thereby producing a therapeutic effect.

13. The method of claim 12, wherein insertion of the nasal insert body into the nasal cavity blocks, prevents, reduces, or delays smelling.

14. The method of claim 2, wherein inserting the nasal insert body into the nasal cavity distorts smelling and/or leads to unpleasant and/or different flavors and/or smells, or wherein the nasal insert body contains, comprises, or is capable of transferring to the nasal cavity a substance that affects the individual's perception of odor(s) and/or flavors.

15. The method of claim 12, wherein the nasal insert body is configured to be positioned in one or more nasal meatuses and/or other areas of the nasal cavity and/or is configured to give the individual a sensation of satiation.

16. The method of claim 12, wherein the nasal insert is used for a duration, situation, and/or frequency sufficient to produce the therapeutic effect.

17. The method of claim 12, wherein the nasal insert is worn for providing a therapeutic substance, and wherein the nasal insert is positioned in the nasal cavity of the individual such that the therapeutic substance reaches a target destination, thereby providing the therapeutic effect.

18. The method of claim 12, wherein the nasal insert is worn to create a feeling of a mild cold and/or light runny nose, and/or a feeling of sickness or a feeling of disgust and/or less enjoyable or less comfortable experience resulting in the therapeutic effect.

19. The method of claim 12, wherein said outer surface is configured to form a seal with the nasal cavity.

20. The method of claim 12, wherein the nasal insert body comprises or contains an anti-obesity therapeutic agent, which is provided to the individual through the nasal cavity, when the nasal insert body is inserted in the nasal cavity.

21. The method of claim 20, wherein the anti-obesity therapeutic agent comprises at least one of Leptin or a hormone that inhibits generation of Ghrelin.

22. A method for treating allergies, high blood pressure, or one or more of the following addictions: food/eating addiction, sugar/sweet addiction, carbohydrate addiction, alcohol addiction, cocaine addiction, heroin addiction, sex addiction, computer game addiction, Internet/social network addiction, chocolate addiction, addiction to non-inhaled drugs, addiction to ingested drugs, addiction to injected drugs, or addiction to drugs by intranasal use, the method comprising the steps of:

providing a nasal insert, said nasal insert including a body for insertion into a nasal cavity, said nasal insert body defining an air passageway, and having an outer surface; and inserting said nasal insert body into the nasal cavity of an individual diagnosed with or suspected of having allergies, high blood pressure, or one or more of the addictions, such that the nasal insert body rests against a portion of the nasal cavity;

wherein the nasal insert body is configured to either (1) create a bypass of an olfactory region of the nasal cavity or direct any substance away from the olfactory region thereby delaying, blocking, or reducing an amount of or manipulating the any substance from reaching the olfactory region, or being in close proximity to the olfactory region, and/or to one or more other regions of the nasal cavity or beyond, and/or (2) wherein the nasal insert is configured to direct the any substance towards the olfactory region, and/or towards the one or more other regions of the nasal cavity or beyond and/or to manipulate the any substance in relation to the olfactory region and/or the one or more other regions of the nasal cavity or beyond, and/or (3) wherein the nasal insert is configured to manipulate the olfactory region, and/or the one or more other regions of the nasal cavity or beyond;

and wherein the direction of the any substance towards or away from the olfactory region, and/or towards or away from the one or more other regions of the nasal cavity and/or beyond, and/or the blocking or reducing or manipulation of the any substance or the olfactory region and/or the one or more other region and/or beyond, alters, reduces, or manipulates processes thereby producing a therapeutic effect.

23. The method of claim 22, wherein the method treats allergies and the direction of the any substance and/or the manipulation prevents particles causing the allergies from reaching unwanted areas of the nasal cavity and/or beyond.

24. The method of claim 22, wherein said outer surface is configured to form a seal with the nasal cavity.

25. The method of claim 22, wherein the nasal insert body is inserted into the nasal cavity of an individual diagnosed with or suspected of having allergies, and wherein the nasal insert body comprises, contains, or is capable of transferring to the nasal cavity an antihistamine, which is provided to the individual through the nasal cavity.

* * * * *

UNITED STATES PATENT AND TRADEMARK OFFICE
CERTIFICATE OF CORRECTION

PATENT NO. : 10,905,579 B2  
APPLICATION NO. : 16/014354  
DATED : February 2, 2021  
INVENTOR(S) : Adva Beck Page 1 of 1

It is certified that error appears in the above-identified patent and that said Letters Patent is hereby corrected as shown below:

In the Claims

Column 67, Line 9, Claim 1, delete "form" and insert -- from --

Column 68, Line 17, Claim 12, delete "form" and insert -- from --

Column 68, Line 27, Claim 14, delete "claim 2," and insert -- claim 12, --

Column 70, Line 9, Claim 22, delete "region" and insert -- regions --

Signed and Sealed this  
Tenth Day of August, 2021

Drew Hirshfeld  
*Performing the Functions and Duties of the*  
*Under Secretary of Commerce for Intellectual Property and*  
*Director of the United States Patent and Trademark Office*